United States Patent
Raymond et al.

(10) Patent No.: US 9,439,984 B2
(45) Date of Patent: Sep. 13, 2016

(54) MACROCYCLES

(71) Applicant: THE REGENTS OF THE UNIVERSITY OF CALIFORNIA, Oakland, CA (US)

(72) Inventors: Kenneth N. Raymond, Berkeley, CA (US); Jide Xu, Richmond, CA (US); Tiffany A. Pham, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/403,401

(22) PCT Filed: Mar. 14, 2013

(86) PCT No.: PCT/US2013/031648
§ 371 (c)(1),
(2) Date: Nov. 24, 2014

(87) PCT Pub. No.: WO2013/187971
PCT Pub. Date: Dec. 19, 2013

(65) Prior Publication Data
US 2015/0157746 A1    Jun. 11, 2015

Related U.S. Application Data

(60) Provisional application No. 61/654,076, filed on May 31, 2012.

(51) Int. Cl.
*A61K 51/04* (2006.01)
*C07D 259/00* (2006.01)
*C07B 59/00* (2006.01)
*C07D 401/14* (2006.01)

(52) U.S. Cl.
CPC .......... *A61K 51/0482* (2013.01); *C07B 59/004* (2013.01); *C07D 259/00* (2013.01); *C07D 401/14* (2013.01)

(58) Field of Classification Search
CPC ....... A61K 51/00; C07D 259/00; C07F 5/00; C07F 7/00
See application file for complete search history.

(56) References Cited

U.S. PATENT DOCUMENTS

| | | |
|---|---|---|
| 5,010,191 A | 4/1991 | Engelstad et al. |
| 5,482,698 A | 1/1996 | Griffiths |
| 5,601,800 A | 2/1997 | Katti et al. |
| 6,846,915 B2 | 1/2005 | Raymond et al. |
| 7,404,912 B2 | 7/2008 | Raymond et al. |

FOREIGN PATENT DOCUMENTS

WO    WO 2008/008797    1/2008

OTHER PUBLICATIONS

Yizhen Sun et al. New Multidentate Ligands. 28. Synthesis and Evaluation of New Macrocyclic Ligands Containing Bidentate Endocyclic Catechol Donor Groups, Inorg. Chem. 1986, 25, 4780-4785.*
Boswell and Brechbiel, "Development of Radioimmunotherapeutic and Diagnostic Antibodies: An Inside-Out View." Nucl. Med. Biol. 34(7): 757-778 (2007).

* cited by examiner

*Primary Examiner* — Michael G Hartley
*Assistant Examiner* — Jagadishwar Samala
(74) *Attorney, Agent, or Firm* — Morgan, Lewis & Bockius LLP; Todd Esker

(57) ABSTRACT

The invention provides macrocycles useful in chelating metal ions, particularly radionuclides, to provide metal ion complexes. The invention also provides methods of using the compounds and complexes of the invention, such as in therapeutic and diagnostic applications.

7 Claims, 8 Drawing Sheets

Solution Thermodynamics: $\beta$'s

Indirect Kinetic Studies

+ L ⟶ ThL + arsenazo III (D)

| Ligand | $k_{2,obs}$ (M$^{-1}$ s$^{-1}$) |
|---|---|
| Φ22moeTAM | 129 |
| 343LiMeTAM | 71 |
| DTPA | 0.61 |
| DOTA | 0.93* |

DTPA

DOTA

Conditions: 5 µM ThD, 50 µM L
pH 7.4, 25 °C, *100 °C

MACROCYCLES

CROSS-REFERENCES TO RELATED APPLICATIONS

This application claims the benefit under 35 U.S.C. §119 (e) of U.S. Provisional Application No. 61/654,076, filed May 31, 2012, the disclosure of which is incorporated herein by reference in its entirety for all purposes.

STATEMENT REGARDING FEDERALLY SPONSORED RESEARCH OR DEVELOPMENT

The invention was made with government support under Contract No. DE-AC02-05CH11231 awarded by the U.S. Department of Energy. The government has certain rights in the invention.

TECHNICAL FIELD

The invention relates to chemical compounds and complexes that can be used in therapeutic and diagnostic applications.

DESCRIPTION OF EMBODIMENTS

Definitions

Figure 1A:
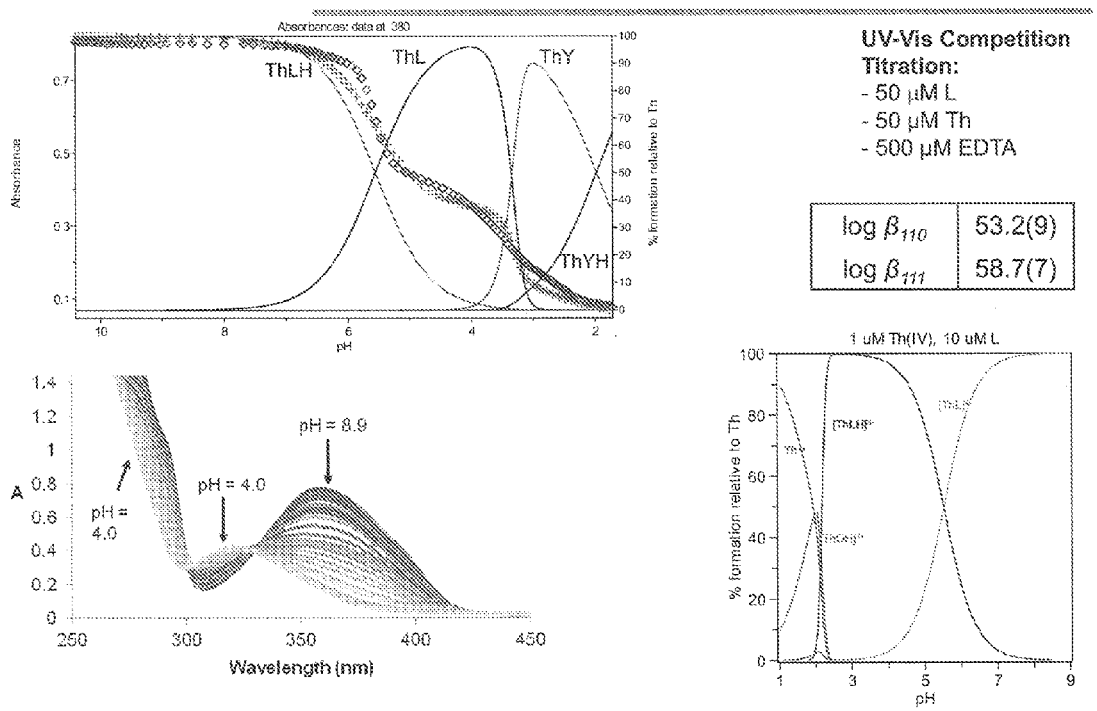
FIGS. 1A and 1B show solution thermodynamics data for the Th(IV)-phi(2,2)moeTAM complex.

Where substituent groups are specified by their conventional chemical formulae, written from left to right, they optionally equally encompass the chemically identical substituents, which would result from writing the structure from right to left, e.g., —CH$_2$O— is intended to also recite —OCH$_2$—.

The term "alkyl", by itself or as part of another substituent, means a straight or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl) methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means an alkyl in which one or more carbons are replaced with one or more heteroatoms selected from the group consisting of O, N, Si and S, (preferably O, N and S), wherein the nitrogen and sulfur atoms may optionally be oxidized and the nitrogen heteroatom may optionally be quaternized. The heteroatoms O, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$) alkyl according to the valence of the heteroatom. Examples of heteroalkyl groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. No more than two heteroatoms may be consecutive, as in, for example, —CH$_2$—NH—OCH$_3$ and —CH$_2$—O—Si(CH$_3$)$_3$, and in some instances, this may place a limit on the number of heteroatom substitutions. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. The designated number of carbons in heteroforms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5C and 1N or 1-4C and 2N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from 0, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The terms "cycloalkyl" and "heterocycloalkyl", by themselves or in combination with other terms, refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic substituent that can be a single ring or optionally multiple rings (preferably 1, 2 or 3 rings) that are fused together or linked covalently. In some embodiments, aryl is a 3, 4, 5, 6, 7 or 8 membered ring, which is optionally fused to one or two other 3, 4, 5, 6, 7 or 8 membered rings. The term "heteroaryl" refers to aryl groups (or rings) that contain 1, 2, 3 or 4 heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. In one embodiment, R', R", R'" and R"" are each independently selected from hydrogen, alkyl (e.g., $C_1$, $C_2$, $C_3$, $C_4$, $C_5$ and $C_6$ alkyl). In one embodiment, R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R'" and R"" are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R'" and R"" are independently selected from hydrogen and alkyl (e.g., $C_1$, $C_2$, $C_3$, $C_4$, $C_5$ and $C_6$ alkyl). In some embodiments, R', R", R'" and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R'" and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. In some embodiments, R is selected from H and ($C_1$-$C_6$)alkyl.

The terms "halo" or "halogen," by themselves or as part of another substituent, unless otherwise stated, mean, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. In some embodiments, halogen refers to an atom selected from F, Cl and Br.

The term "heteroatom" includes oxygen (O), nitrogen (N), sulfur (S) and silicon (Si). In some embodiments, a heteroatom is selected from N and S. In some embodiments, the heteroatom is O.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R'" and R"" group, they are each independently selected.

For groups with solvent exchangeable protons, the ionized form is equally contemplated. For example, —COOH also refers to —COO⁻ and —OH also refers to —O⁻.

Any of the compounds disclosed herein can be made into a pharmaceutically acceptable salt. The term "pharmaceutically acceptable salts" includes salts of compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides any of the compounds disclosed herein in a prodrug form. Prodrugs of the compounds described herein are those compounds that readily undergo chemical changes under physiological conditions to provide the compounds of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The symbol , displayed perpendicular to a bond, indicates the point at which the displayed moiety is attached to the remainder of the molecule.

In some embodiments, the definition of terms used herein is according to IUPAC.

Macrocycles

The invention provides numerous chelators and metal ion complexes thereof. Generally, a chelator comprises a plurality of chelating agents that are linked together by way of two or more scaffold moieties. Chelating moieties bound together by two scaffold moieties such that at least one closed ring is formed can be referred to as closed chelators, macrocycles or macrocyclic chelators.

Based on the well defined background on the kinetic and in vivo properties of the open chain octadentate ligand DTPA and their derivatives, octadentate chelates disclosed herein are an ideal design as an anticancer chelator for thorium, specifically those isotopes that decay via alpha-emission. These are also open chain, linear chelators designed to give faster kinetics with strong binding affinity to the metal. Low toxicity is another essential requirement as well which has been shown by our past work to be influenced by the type of chelating unit, ligand multidenticity, and topology in the ligand design.

There are several factors to be considered in the design for an alpha chelating agent for anticancer therapy. Some of the key issues apart from the kinetics will be the high affinity for the target metal (Th) which at the same time needs to have a low exchange rate for other biologically significant metal ions. So, in our ligand design, the electronic properties of the target metal and ligand are considered and matched. The chelate should also be able to assume the appropriate coordination cavity size and geometry for the desired metal. In this case, Th, an actinide ion, is a "hard" cation and has a large charge-to-radius ratio. Hence, Th prefers "hard" electron donors and negatively charged oxygen donors. A coordination number of 8 or greater is generally preferred by actinide ions as they have a tendency to form stable complexes with ligands of high denticity; however, the selectivity towards the binding of the thorium will be determined by our design of the chelating unit. The effective but nonselective amino-carboxylic acid ligands such as DTPA can deplete essential biological metal ions from patients, thus causing serious health problems. Selecting the correct type of chelating unit, therefore, is an important factor in achieving high selectivity toward the specific metal ion.

A chelator can comprise numerous chelating moieties. Particularly useful chelators contain a number of chelating moieties sufficient to provide, for example, 6, 8 or 10 heteroatoms such as oxygen that coordinate with a metal ion to form a complex. The heteroatoms such as oxygen provide electron density for forming coordinate bonds with a positively charged ion, and such heteroatoms can thus be considered "donors". In some embodiments, the plurality of chelating moieties of a chelator comprises a plurality of oxygen donors and a radionuclide is chelated to the chelator via at least one of the oxygen donors. In some embodiments, a chelator comprises a plurality of oxygen donors and a radionuclide is chelated to the chelator via a plurality or all of the oxygen donors.

Accordingly, in one aspect, the invention provides a macrocycle of formula (M1), (M2), (M3), or (M4):

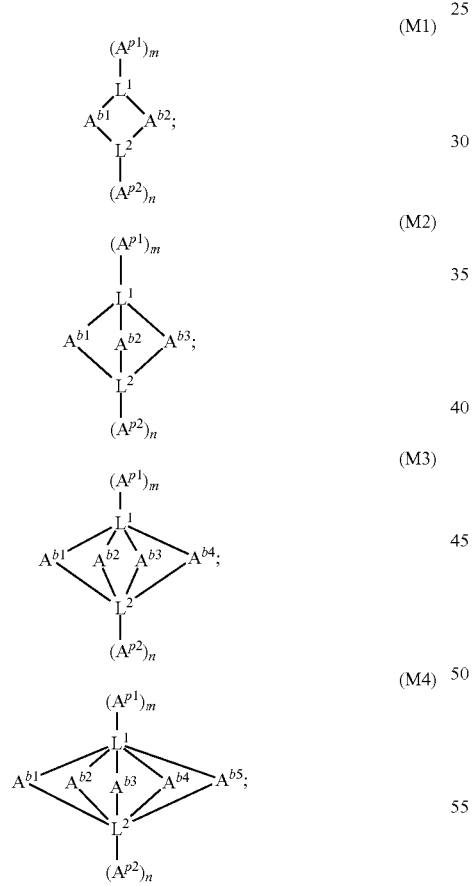

wherein $L^1$ and $L^2$ are independently selected scaffold moieties.
$A^{b1}, A^{b2}, A^{b3}, A^{b4}, A^{b5}$ are independently selected bridging chelating moieties.
Each $A^{p1}$ and $A^{p2}$ is an independently selected pendant chelating moiety.
m is an integer selected from 1, 2, 3, and 4.
n is an integer selected from 0, 1, 2, and 3.

Scaffold moieties, bridging chelating moieties and pendant chelating moiety are as defined herein.

Any of the combinations of $L^1$, $L^2$, $A^{b1}$, $A^{b2}$, $A^{b3}$, $A^{b4}$, $A^{b5}$, $A^{p1}$, $A^{p2}$, m and n are encompassed by this disclosure and specifically provided by the invention.

In some embodiments, the macrocycle comprises a linker. In some embodiments, the linker is attached to a targeting moiety. In some embodiments, the macrocycle comprises a targeting moiety.

Chelating Moieties

Bridging Chelating Moieties $A^{b1}, A^{b2}, A^{b3}, A^{b4}, A^{b5}$ are bridging chelating moieties having the structure:

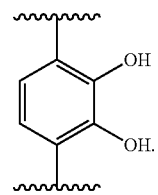 [SMILES: *c1ccc(*)c(O)c1O]

Pendant Chelating Moieties

Each $A^{p1}$ and $A^{p2}$ is a pendant chelating moiety having a structure independently selected from:

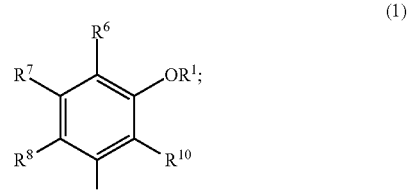
(1)

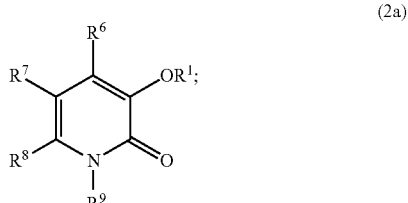
(2a)

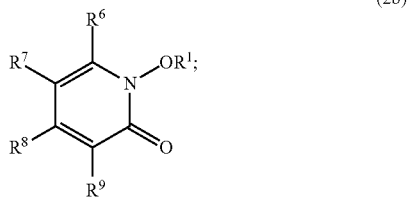
(2b)

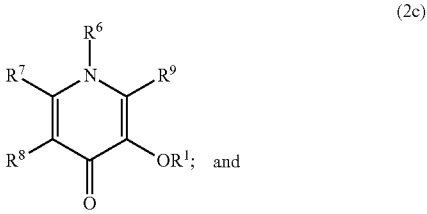
(2c)

and

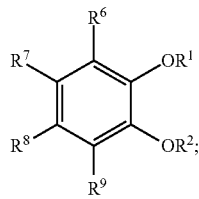

(3)

wherein each $R^6$, $R^7$, $R^8$, $R^9$ and $R^{10}$ in each chelating moiety are independently selected from a bond to $L^1$, a bond to $L^2$, alkanediyl attached to $L^1$, alkanediyl attached to $L^2$, a linker, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, CN, $CF_3$, —$C(O)R^{17}$, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$NR^{17}C(O)R^{18}$, —$NR^{17}SO_2R^{18}$ and —$NO_2$; $R^{17}$ and $R^{18}$ are each independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; $R^{17}$ and $R^{18}$, together with the atoms to which they are attached, are optionally joined to form a 5-, 6- or 7-membered ring; at least two of $R^6$, $R^7$, $R^8$, $R^9$ and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl; $R^1$ and $R^2$ are each independently selected from H and a negative charge; $R^6$ in (2c), one of $R^6$ and $R^9$ in (2a), (2b) and (3) and one of $R^6$ and $R^{10}$ in (1) comprises a bond to $L^1$ or a bond to $L^2$.

In some embodiments, $R^6$ in (2c) is a methylene moiety attached to $L^1$ or $L^2$. In some embodiments, $R^6$ in (2c) is an ethylene moiety attached to $L^1$ or $L^2$.

In some embodiments, one of the pendant chelating moieties comprises a linker. In some embodiments, the linker is attached to a targeting moiety. In some embodiments, one of the pendant chelating moieties comprises a targeting moiety.

In some embodiments, $A^{p1}$ and $A^{p2}$ is a pendant chelating moiety having a structure independently selected from:

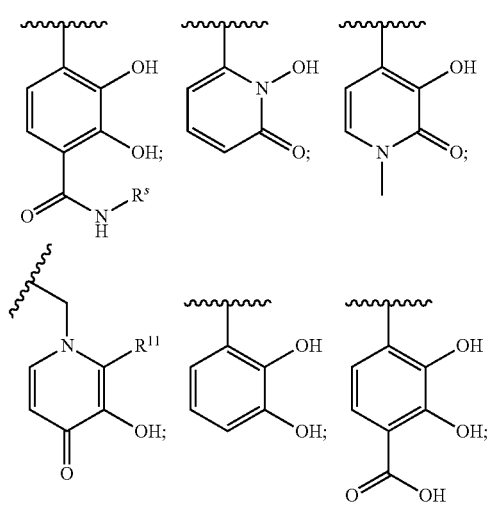

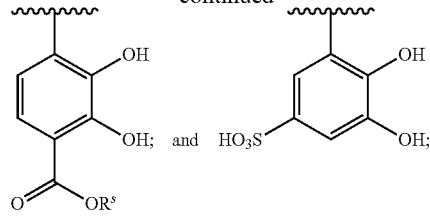

wherein $R^s$ is a member selected from H, substituted or unsubstituted alkyl, and substituted or unsubstituted heteroalkyl; and $R^{11}$ is substituted or unsubstituted alkyl.

In some embodiments, $R^{11}$ is unsubstituted $C_1$, $C_2$, $C_3$, $C_4$, $C_5$, or $C_6$ alkyl. In some embodiments, $R^{11}$ is methyl. In some embodiments $R^{11}$ is ethyl.

Solubilizing Group

Each $A^{p1}$ and $A^{p2}$ optionally comprises a solubilizing group. The solubilizing group improves solubility of the macrocycle and/or a complex formed between the macrocycle and a metal ion in aqueous media.

In some embodiments, the solubilizing group does not interact with the metal when the macrocycle is complexed to a metal. In some embodiments, the solubilizing group does not comprise —$C(O)OH$ or —$C(O)NR^{12}OH$, wherein $R^{12}$ is a member selected from H, unsubstituted $C_1$, $C_2$, $C_3$, $C_4$, $C_5$ or $C_6$ alkyl, and substituted $C_1$, $C_2$, $C_3$, $C_4$, $C_5$ or $C_6$ alkyl.

In some embodiments, $R^s$ comprises a solubilizing group. In some embodiments, $R^s$ is a solubilizing group. In some embodiments, $R^s$ is a member selected from substituted alkyl and substituted or unsubstituted heteroalkyl. In some embodiments, $R^s$ is substituted alkyl. In some embodiments, $R^s$ is substituted $C_2$, $C_3$, or $C_4$ alkyl. In some embodiments, $R^s$ is $C_2$, $C_3$, or $C_4$ alkyl substituted with a member selected from $OR^{s1}$, $SO_3R^{s1}$, and $NR^{s1}R^{s2}$; wherein $R^{s1}$ and $R^{s2}$ are independently selected from H and substituted or unsubstituted alkyl. In some embodiments, $R^{s1}$ is methyl. In some embodiments $R^{s1}$ is H. In some embodiments $R^{s2}$ is methyl. In some embodiments, $R^s$ is a member selected from —$CH_2CH_2OR^{s1}$, —$CH_2CH_2SO_3R^{s1}$, and —$CH_2CH_2NR^{s1}R^{s2}$. In some embodiments, $R^s$ is a member selected from —$CH_2CH_2OCH_3$, —$CH_2CH_2OH$, —$CH_2CH_2SO_3H$, and —$CH_2CH_2N(CH_3)_2$.

Scaffold Moieties

A "scaffold moiety" is any moiety useful for covalently linking two or more chelating moieties in any of the chelators (macrocycles) disclosed herein. In exemplary embodiments, any two scaffold moieties disclosed herein are joined via a plurality of chelating moieties to form a macrocycle. In exemplary embodiments, one or more scaffold moieties of a chelator is substituted with a linker. In one embodiment, a scaffold moiety is selected from substituted or unsubstituted alkyl and substituted or unsubstituted heteroalkyl. In one embodiment, a scaffold moiety is substituted heteroalkyl. In one embodiment, a scaffold moiety is unsubstituted heteroalkyl. In one embodiment, a scaffold moiety is heteroalkyl substituted with a linker. In one embodiment, a scaffold moiety is heteroalkyl substituted with a plurality of linkers. Exemplary scaffold moieties include linear or branched ethers and amines. In some embodiments, the linker is attached to a targeting moiety. In some embodiments, the scaffold moiety comprises a targeting moiety.

Other exemplary scaffold moieties include, but are not limited to:

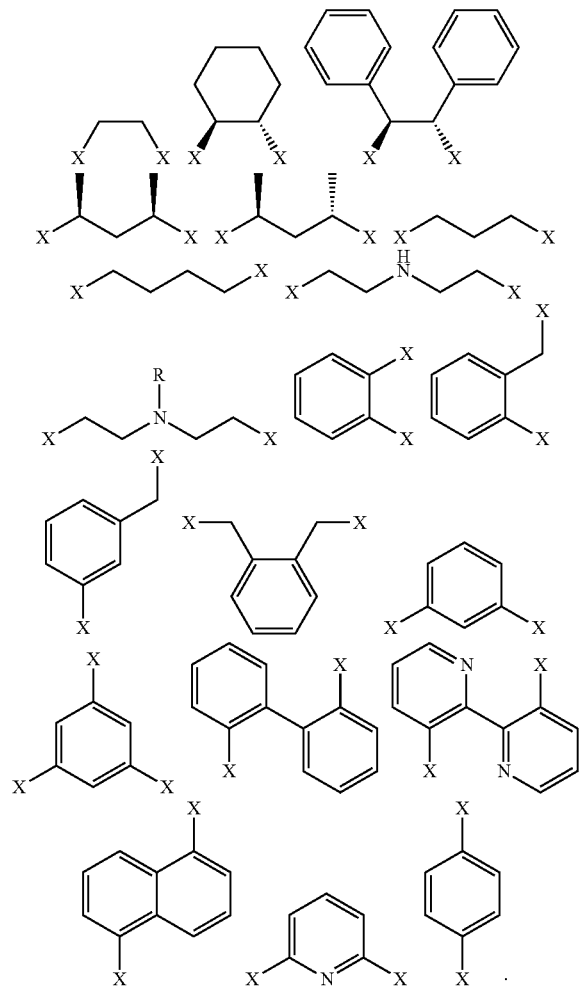

"X" represents a locus of attachment for a chelating moiety, and in exemplary embodiments includes a heteroatom such as nitrogen. Thus, in some embodiments, X is NR'R", wherein R' and R" are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, CN, $CF_3$, —$C(O)R^{17}$, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$NR^{17}C(O)R^{18}$, —$NR^{17}SO_2R^{18}$, —$NO_2$; and $R^{17}$ and $R^{18}$ are each independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; wherein at least one R' or R" comprises a bond to a chelating moiety. The chelating moiety can be attached to a scaffold via any appropriate linker.

In some embodiments, a scaffold moiety is linear. One exemplary scaffold moiety is X—$(CH_2)_3$—X—$(CH_2)_4$—X—$(CH_2)_3$—X, which is preferably substituted (e.g. with a linker) at at least one of the alkyl moieties. That is, one exemplary scaffold moiety is spermine based. Other exemplary scaffold moieties include

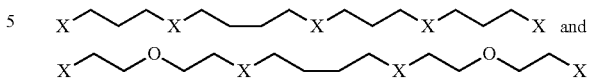

any of which is preferably substituted (e.g. with a linker) at at least one of the alkyl moieties. X is as given in the previous paragraph.

One preferred moiety for at least one of the X moieties is the TAM amide moiety, but those of skill in the art will appreciate that other chelating moieties in any used in any combination. In each of the scaffold structures, an aryl moiety or alkyl moiety can be substituted with one or more "aryl group substituent" or "alkyl group substituent" as defined herein.

A particularly useful scaffold moiety for any chelator described herein has the structure

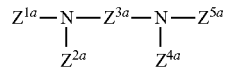

wherein $Z^{1a}$, $Z^{2a}$, $Z^{3a}$, $Z^{4a}$ and $Z^{5a}$ are selected from substituted or unsubstituted alkyl and substituted or unsubstituted heteroalkyl; and $Z^{1a}$, $Z^{2a}$, $Z^{4a}$ and $Z^{5a}$ comprise a bond to one of the chelating moieties.

In some embodiments, $Z^{3a}$ is substituted or unsubstituted ($C_1$, $C_2$, $C_3$, $C_4$, $C_5$ or $C_6$) alkyl. In some embodiments, $Z^{3a}$ is substituted or unsubstituted —$(CH_2)_m(CH_2CH_2O)_n(CH_2)_p$—, wherein m, n and p are integers independently selected from 1, 2, 3, 4, 5 and 6. In some embodiments, $Z^{3a}$ is ethyl. In some embodiments, $Z^{3a}$ is ethyl substituted with =O.

In some embodiments, $Z^{1a}$, $Z^{2a}$, $Z^{4a}$ and $Z^{5a}$ have a structure selected from Z'$R^{20a}$N(H)C(O)Z", Z'$R^{20a}$N(H)C(O)$R^{21a}$Z" and Z'$R^{21a}$Z" wherein Z' is a bond to the second scaffold moiety, Z" is a bond to one of the plurality of chelating moieties, $R^{20a}$ is selected from substituted or unsubstituted alkyl and substituted or unsubstituted heteroalkyl. and $R^{21a}$ is selected from substituted or unsubstituted alkyl and substituted or unsubstituted heteroalkyl. In some embodiments, $R^{20a}$ is selected from substituted or unsubstituted ($C_1$, $C_2$, $C_3$, $C_4$, $C_5$ or $C_6$) alkyl and substituted or unsubstituted ($C_1$, $C_2$, $C_3$, $C_4$, $C_5$ or $C_6$) heteroalkyl. In some embodiments, $R^{20a}$ is selected from substituted or unsubstituted ethyl. In some embodiments, $R^{21a}$ is from substituted or unsubstituted —$(CH_2)_wO$— wherein w is selected from 1, 2, 3, 4, 5 and 6. In exemplary embodiments, w is 1 or 3.

In some embodiments, at least one of $Z^{1a}$, $Z^{2a}$, $Z^{3a}$, $Z^{4a}$ and $Z^{5a}$ is substituted with a linker.

Another particularly useful scaffold moiety for any chelator herein has the structure

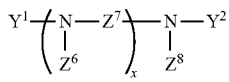

x is selected from 1, 2, 3 and 4. In exemplary embodiments, x is 1. In exemplary embodiments, x is 2. In exemplary embodiments, x is 3. In exemplary embodiments, x is 4.

$Y^1$ and $Y^2$ are each independently selected from H, substituted or unsubstituted alkyl and substituted or unsubstituted heteroalkyl. In exemplary embodiments, $Y^1$ and $Y^2$ are H.

$Z^7$ is selected from substituted or unsubstituted alkyl and substituted or unsubstituted heteroalkyl. In exemplary embodiments, at least one $Z^7$ is substituted with a linker. In some embodiments, each $Z^7$ is independently substituted or unsubstituted ($C_1$, $C_2$, $C_3$, $C_4$, $C_5$ or $C_6$) alkyl. In exemplary embodiments, each $Z^7$ is independently substituted or unsubstituted propyl or butyl. In some embodiments, each $Z^7$ is independently substituted or unsubstituted heteroalkyl.

In exemplary embodiments, each $Z^7$ is independently substituted or unsubstituted $—(CH_2)_m(CH_2CH_2O)_n(CH_2)_p—$, wherein m, n and p are integers independently selected from 1, 2, 3, 4, 5 and 6. In exemplary embodiments, each $Z^7$ is substituted or unsubstituted $—(CH_2)_2O(CH_2)_2—$.

$Z^6$ and $Z^8$ are independently selected from $—C(O)—$, substituted or unsubstituted alkyl, and substituted or unsubstituted heteroalkyl; and each of $Z^6$ and $Z^8$ comprises a bond to one of the chelating moieties.

In exemplary embodiments, $Z^6$ and $Z^8$ are $—C(O)—$.

Another useful scaffold moiety has the structure:

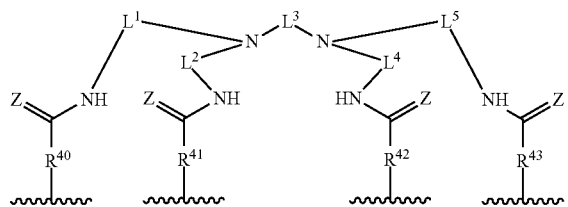

in which each Z is independently selected from O and S. In some embodiments, $L^3$ comprises $—(CH_2CH_2O)_mR^{31}—$ wherein m is an integer selected from 0, 1, 2, 3, 4, 5, 6, 7, 8 and 9. In some embodiments, m is 0. In some embodiments, m is 1. In some embodiments, $L^3$ is $—CH_2CH_2OCH_2CH_2—$. $L^1$, $L^2$, $L^4$, $L^5$ and $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $L^1$, $L^2$, $L^4$, $L^5$ are independently selected substituted or unsubstituted ($C_1$, $C_2$, $C_3$, $C_4$, $C_5$ or $C_6$) alkyl. In some embodiments, $R^{31}$ is substituted or unsubstituted ($C_1$, $C_2$, $C_3$, $C_4$, $C_5$ or $C_6$) alkyl. In exemplary embodiments, $L^1$, $L^2$, $L^4$, $L^5$ are independently selected substituted or unsubstituted ethyl. In some embodiments, $R^{31}$ is substituted or unsubstituted ethyl. In exemplary embodiments, $L^1$, $L^2$, $L^4$, $L^5$ are ethyl, one or more of which is substituted with a linker. In some embodiments, $L^1$ is substituted with a linker. In some embodiments, $L^2$ is substituted with a linker. In some embodiments, $L^3$ is substituted with a linker. In some embodiments, $L^4$ is substituted with a linker. In some embodiments, $L^5$ is substituted with a linker. In some embodiments, $L^1$ is ethyl substituted with a linker. In some embodiments, $L^2$ is ethyl substituted with a linker. In some embodiments, $L^3$ is ethyl substituted with a linker. In some embodiments, $L^4$ is ethyl substituted with a linker. In some embodiments, $L^5$ is ethyl substituted with a linker. In some embodiments, $R^{40}$, $R^{41}$, $R^{42}$ and $R^{43}$ are bonds. In some embodiments, $R^{40}$, $R^{41}$, $R^{42}$ and $R^{43}$ are $—(CH_2)_wO—$, wherein w is selected from 0, 1, 2, 3, 4, 5, 6, 7, 8, 9 and 10. In exemplary embodiments, w is 3.

Another useful scaffold has the structure

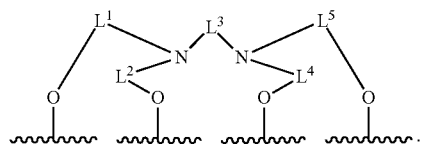

In some embodiments, $L^3$ comprises $—(CH_2CH_2O)_mR^{31}—$ wherein m is an integer selected from 0, 1, 2, 3, 4, 5, 6, 7, 8 and 9. In some embodiments, m is 0. In some embodiments, m is 1. In some embodiments, $L^3$ is $—CH_2CH_2OCH_2CH_2—$. In some embodiments, $L^3$ is $—C(O)C(O)—$. $L^1$, $L^2$, $L^4$, $L^5$ and $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $L^1$, $L^2$, $L^4$, $L^5$ are independently selected substituted or unsubstituted ($C_1$, $C_2$, $C_3$, $C_4$, $C_5$ or $C_6$) alkyl. In some embodiments, $R^{31}$ is substituted or unsubstituted ($C_1$, $C_2$, $C_3$, $C_4$, $C_5$ or $C_6$) alkyl. In exemplary embodiments, $L^1$, $L^2$, $L^4$, $L^5$ are independently selected substituted or unsubstituted ethyl. In exemplary embodiments, $L^1$, $L^2$, $L^4$, $L^5$ are independently selected substituted or unsubstituted propyl. In some embodiments, $R^{31}$ is substituted or unsubstituted ethyl. In exemplary embodiments, $L^1$, $L^2$, $L^4$, $L^5$ are ethyl, one or more of which is substituted with a linker. In some embodiments, $L^1$ is substituted with a linker. In some embodiments, $L^2$ is substituted with a linker. In some embodiments, $L^3$ is substituted with a linker. In some embodiments, $L^4$ is substituted with a linker. In some embodiments, $L^5$ is substituted with a linker. In some embodiments, $L^1$ is propyl substituted with a linker. In some embodiments, $L^2$ is propyl substituted with a linker. In some embodiments, $L^3$ is propyl substituted with a linker. In some embodiments, $L^4$ is propyl substituted with a linker. In some embodiments, $L^5$ is propyl substituted with a linker.

In some embodiments, a scaffold is selected from:

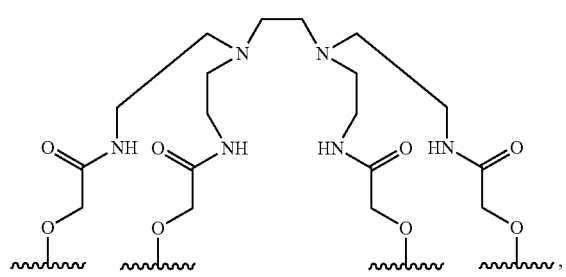

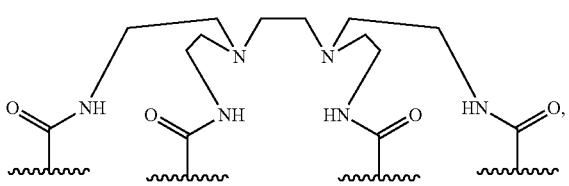

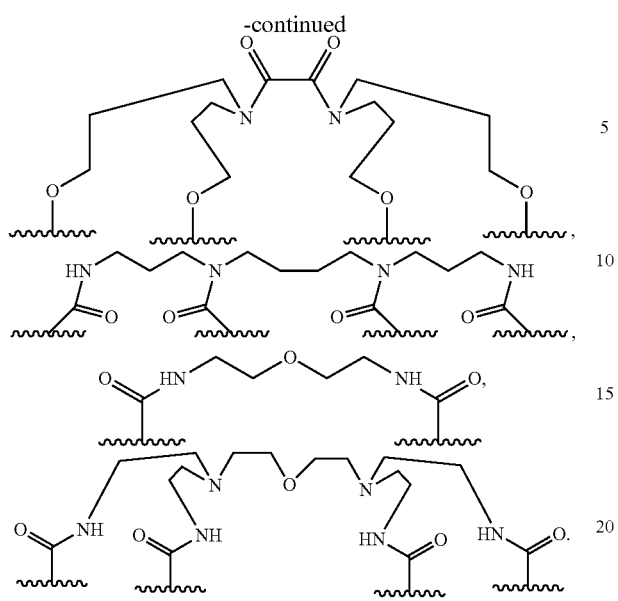

In any of these structures, one or more methyl, ethyl, propyl or butyl moieties can be substituted with one or more linkers. In some embodiments, two of these scaffold moieties, in which one or more methyl, ethyl, propyl or butyl moieties are optionally substituted with one or more linkers, are used to form a macrocycle.

In some embodiments, $L^1$, $L^2$, or both comprise a solubilizing group.

In some embodiments, $L^1$, $L^2$, or both comprise a linker. In some embodiments, the linker is attached to a targeting moiety. In some embodiments, $L^1$, $L^2$, or both comprise a targeting moiety.

In some embodiments, $L^1$, $L^2$, or both have the structure:

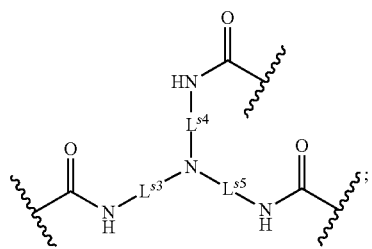

wherein $L^{s3}$ is selected from unsubstituted alkanediyl and alkanediyl substituted with a linker; and $L^{s4}$ and $L^{s5}$ are unsubstituted alkanediyl.

In some embodiments, the linker is attached to a targeting moiety.

In some embodiments, $L^1$, $L^2$, or both have a structure selected from:

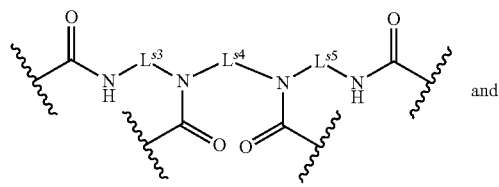

and

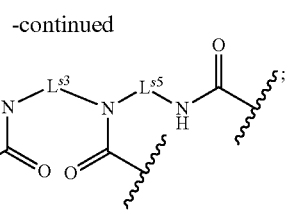

wherein $L^{s3}$ is selected from unsubstituted alkanediyl and alkanediyl substituted with a linker; and $L^{s4}$ and $L^{s5}$ are unsubstituted alkanediyl.

In some embodiments, the linker is attached to a targeting moiety.

In some embodiments, $L^1$ is a scaffold moiety selected from:

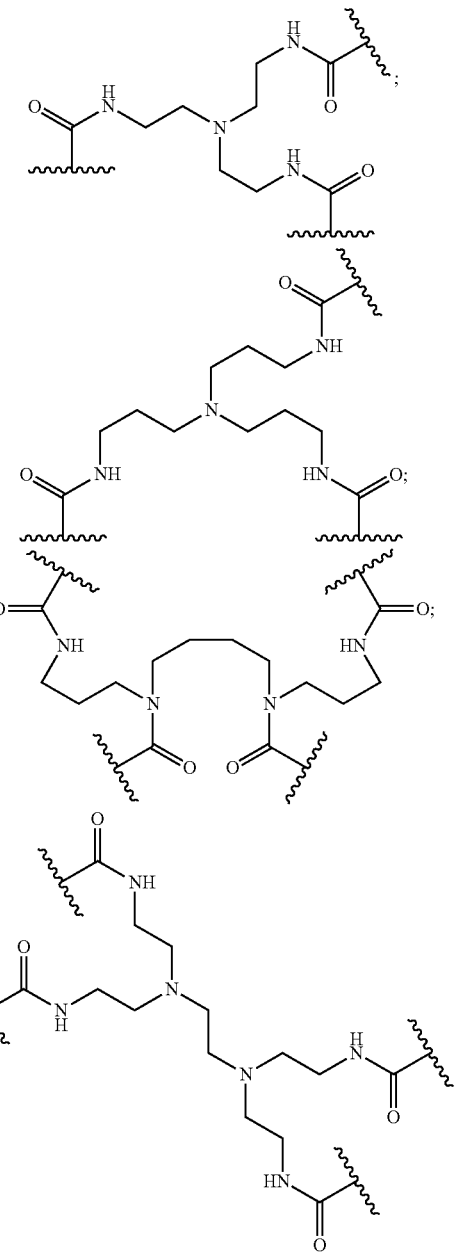

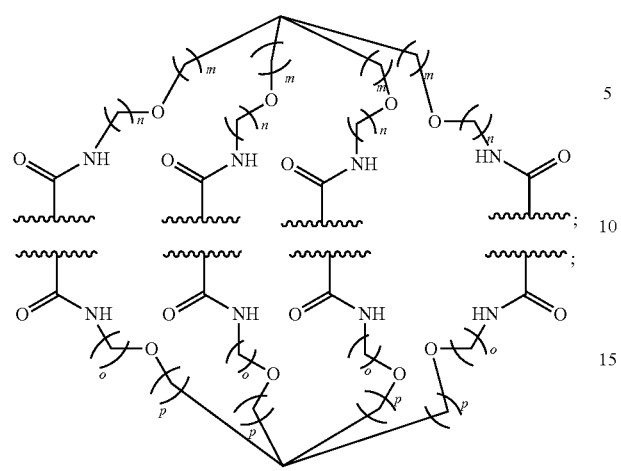

wherein m and p are integers independently selected from 1 and 2; and n and o are integers independently selected from 2 and 3.

In some embodiments, $L^2$ is a scaffold moiety selected from:

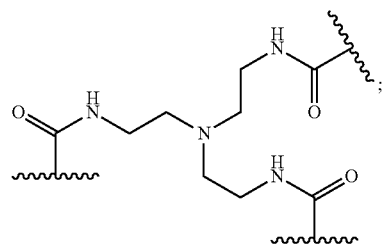

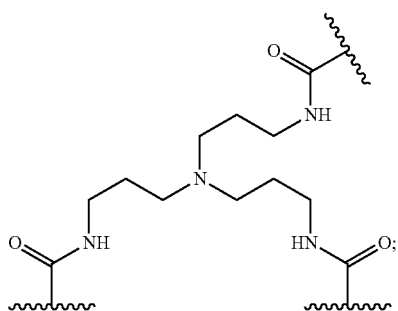

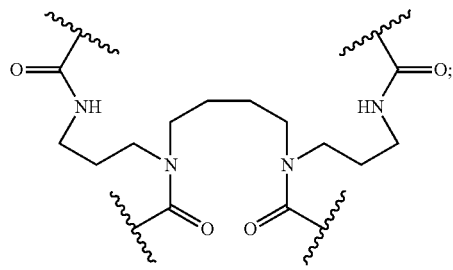

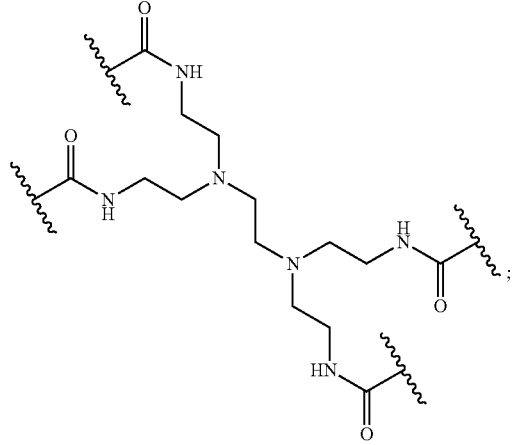

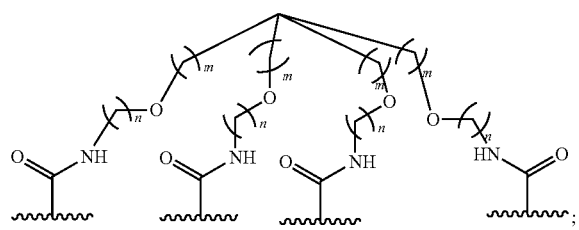

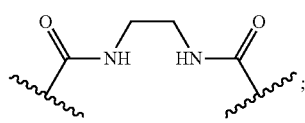

wherein m is an integer selected from 1 and 2; n is an integer selected from 2 and 3; p is an integer selected from 1 and 2; and o is an integer selected from 2 and 3.

Exemplary Macrocycles

In some embodiments, the invention provides a macrocycle of formula (M1):

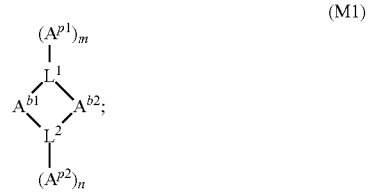

wherein $L^1$ and $L^2$ are independently selected scaffold moieties;

$A^{b1}$ and $A^{b2}$ are each

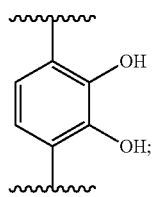 [SMILES: *c1ccc(*)c(O)c1O]

each $A^{p1}$ and $A^{p2}$ is an independently selected pendant chelating moiety;
m is an integer selected from 1, 2, 3, and 4; and
n is an integer selected from 0, 1, 2, and 3.
Scaffold moieties and pendant chelating moiety are as defined herein.

In some embodiments, the invention provides a macrocycle of formula (M1):

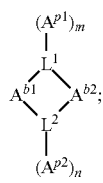

(M1)

wherein $L^1$ and $L^2$ are independently selected scaffold moieties;
$A^{b1}$ and $A^{b2}$ are each

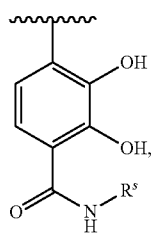

$A^{p1}$ and $A^{p2}$ are each

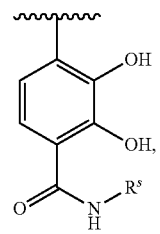

wherein $R^s$ comprises a solubilizing group;
m is 1; and n is 1.
Scaffold moieties are as defined herein.

In some embodiments, $R^s$ is substituted alkyl. In some embodiments, $R^s$ is substituted $C_2$, $C_3$, or $C_4$ alkyl. In some embodiments, $R^s$ is $C_2$, $C_3$, or $C_4$ alkyl substituted with a member selected from $OR^{s1}$, $SO_3R^{s1}$, and $NR^{s1}R^{s2}$; wherein $R^{s1}$ and $R^{s2}$ are independently selected from H and substituted or unsubstituted alkyl. In some embodiments, $R^{s1}$ is methyl. In some embodiments $R^{s1}$ is H. In some embodiments $R^{s2}$ is methyl. In some embodiments, $R^s$ is a member selected from $-CH_2CH_2OR^{s1}$, $-CH_2CH_2SO_3R^{s1}$, and $-CH_2CH_2NR^{s1}R^{s2}$. In some embodiments, $R^s$ is a member selected from $-CH_2CH_2OCH_3$, $-CH_2CH_2OH$, $-CH_2CH_2SO_3H$, and $-CH_2CH_2N(CH_3)_2$.

In some embodiments, the invention provides a macrocycle of formula (M1):

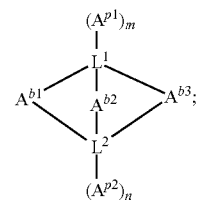

(M2)

wherein $L^1$ and $L^2$ are independently selected scaffold moieties;
$A^{b1}$, $A^{b2}$, and $A^{b3}$ are each

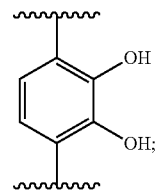

$A^{p1}$ and $A^{p2}$ are each

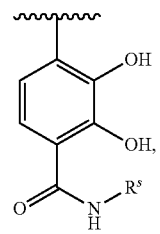

wherein $R^s$ comprises a solubilizing group;
m is 1; and n is 0 or 1.
Scaffold moieties are as defined herein.

In some embodiments, $R^s$ is substituted alkyl. In some embodiments, $R^s$ is substituted $C_2$, $C_3$, or $C_4$ alkyl. In some embodiments, $R^s$ is $C_2$, $C_3$, or $C_4$ alkyl substituted with a member selected from $OR^{s1}$, $SO_3R^{s1}$, and $NR^{s1}R^{s2}$; wherein $R^{s1}$ and $R^{s2}$ are independently selected from H and substituted or unsubstituted alkyl. In some embodiments, $R^{s1}$ is methyl. In some embodiments $R^{s1}$ is H. In some embodiments $R^{s2}$ is methyl. In some embodiments, $R^s$ is a member selected from $-CH_2CH_2OR^{s1}$, $-CH_2CH_2SO_3R^{s1}$, and $-CH_2CH_2NR^{s1}R^{s2}$. In some embodiments, $R^s$ is a member selected from $-CH_2CH_2OCH_3$, $-CH_2CH_2OH$, $-CH_2CH_2SO_3H$, and $-CH_2CH_2N(CH_3)_2$.

In some embodiments, the invention provides a macrocycle of formula (M1):

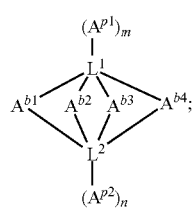
(M3)

wherein L¹ and L² are independently selected scaffold moieties;
$A^{b1}, A^{b2}, A^{b3},$ and $A^{b4}$ are each

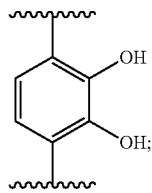 [SMILES: *c1ccc(*)c(O)c1O]

$A^{p1}$ and $A^{p2}$ are each

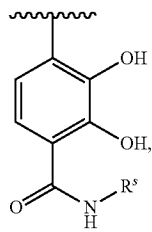

wherein R$^s$ comprises a solubilizing group;
m is 1; and n is 0 or 1.
Scaffold moieties are as defined herein.
In some embodiments, R$^s$ is substituted alkyl. In some embodiments, R$^s$ is substituted $C_2$, $C_3$, or $C_4$ alkyl. In some embodiments, R$^s$ is $C_2$, $C_3$, or $C_4$ alkyl substituted with a member selected from OR$^{s1}$, SO$_3$R$^{s1}$, and NR$^{s1}$R$^{s2}$; wherein R$^{s1}$ and R$^{s2}$ are independently selected from H and substituted or unsubstituted alkyl. In some embodiments, R$^{s1}$ is methyl. In some embodiments R$^{s1}$ is H. In some embodiments R$^{s2}$ is methyl. In some embodiments, R$^s$ is a member selected from —CH$_2$CH$_2$OR$^{s1}$, —CH$_2$CH$_2$SO$_3$R$^{s1}$, and —CH$_2$CH$_2$NR$^{s1}$R$^{s2}$. In some embodiments, R$^s$ is a member selected from —CH$_2$CH$_2$OCH$_3$, —CH$_2$CH$_2$OH, —CH$_2$CH$_2$SO$_3$H, and —CH$_2$CH$_2$N(CH$_3$)$_2$.

In some embodiments, the invention provides a macrocycle having the structure:

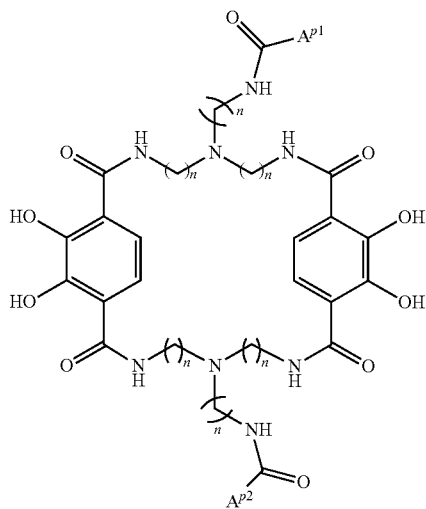

wherein $A^{p1}$ and $A^{p2}$ are independently selected from

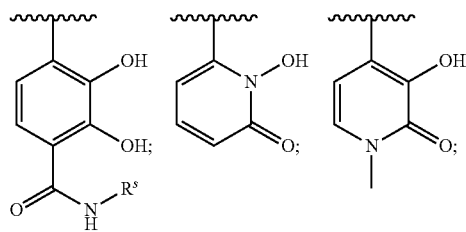

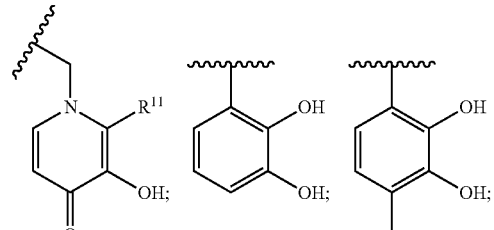

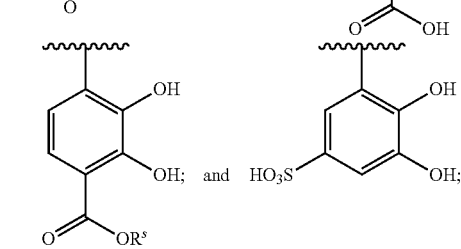

wherein R$^s$ comprises a solubilizing group; and
R$^{11}$ is unsubstituted $C_1$, $C_2$, $C_3$, $C_4$, $C_5$ or $C_6$ alkyl; and
each n is an integer independently selected from 1, 2, 3, 4, 5, and 6.

In some embodiments, each n is an integer independently selected from 1, 2, 3 and 4. In some embodiments, each n is an integer independently selected from 2 and 3.

In some embodiments, $A^{p1}$ and $A^{p2}$ are independently selected from

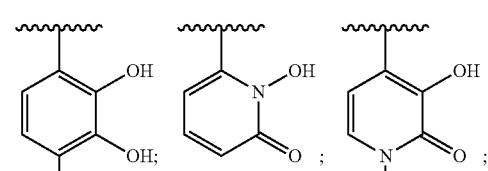

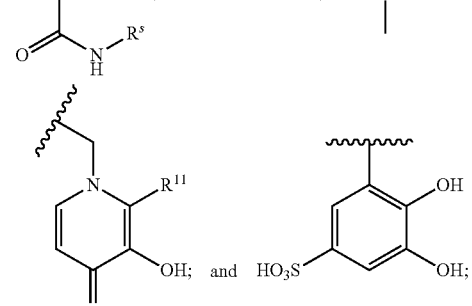

wherein R$^s$ comprises a solubilizing group; and
R$^{11}$ is methyl or ethyl.

In an exemplary embodiment, the invention provides a macrocycle having the structure:

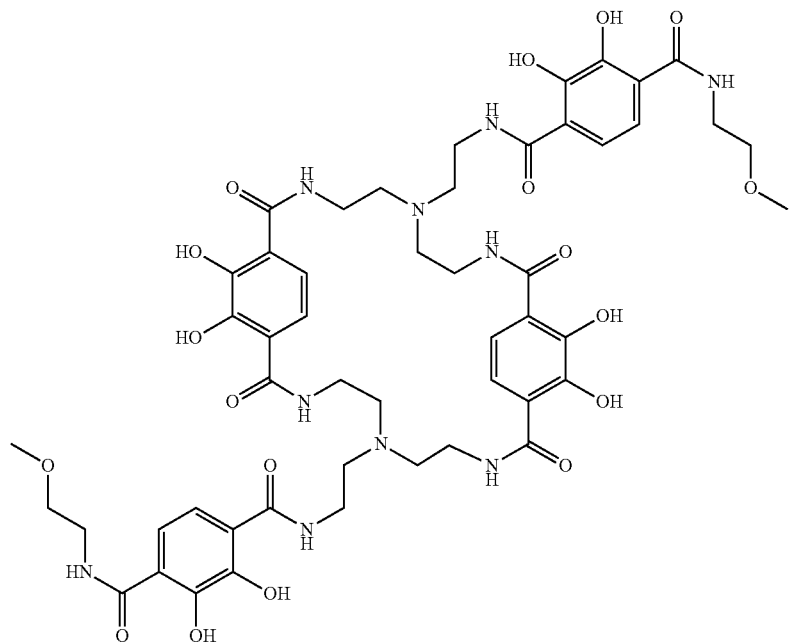
phi(2,2)-moeTAM.
In an exemplary embodiment, the invention provides a macrocycle having the structure:
In an exemplary embodiment, the invention provides a macrocycle having the structure:
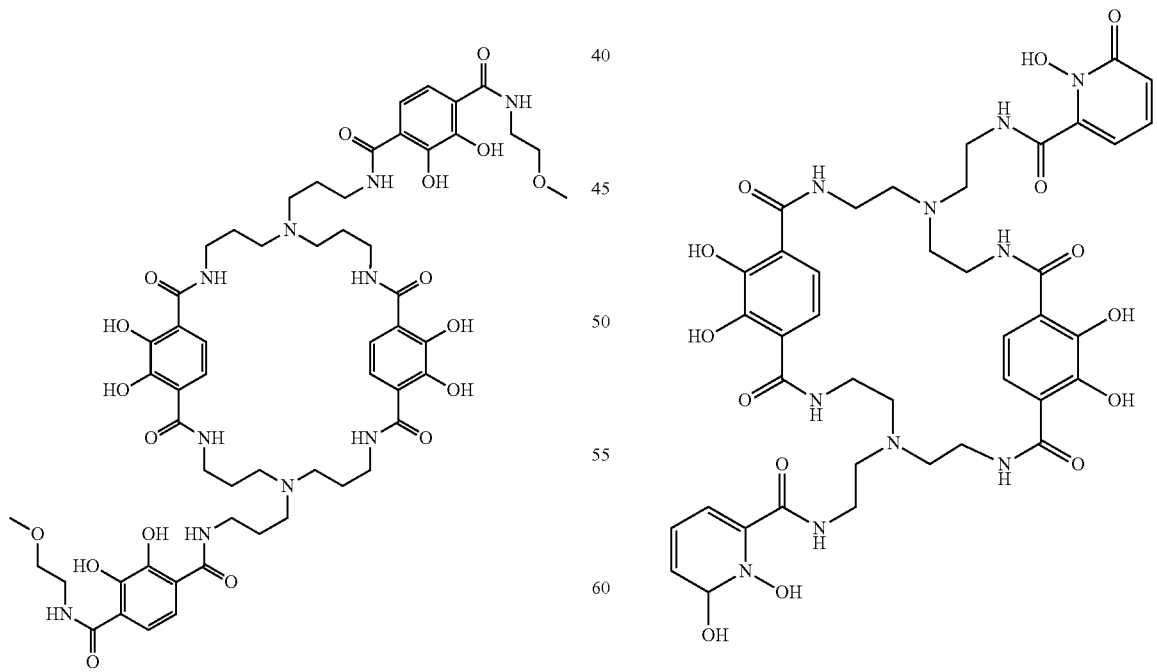
phi(3,3)moeTAM.
phi(2,2)1,2-HOPO.

In some embodiments, the invention provides a macrocycle having the structure:

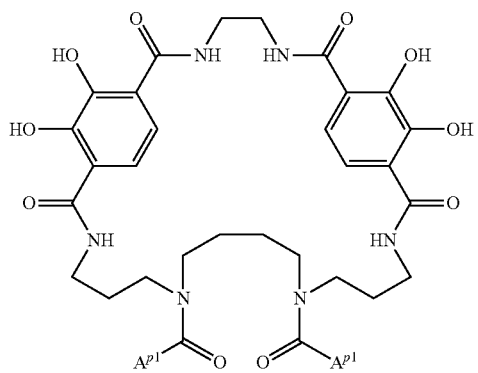

wherein each $A^{p1}$ is independently selected from

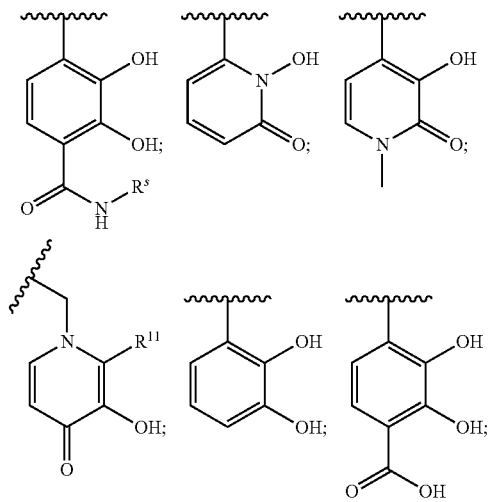

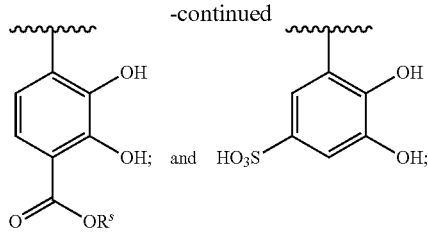

wherein $R^s$ comprises a solubilizing group; and
$R^{11}$ is unsubstituted $C_1$, $C_2$, $C_3$, $C_4$, $C_5$ or $C_6$ alkyl.

In some In some embodiments, each $A^{p1}$ is independently selected from

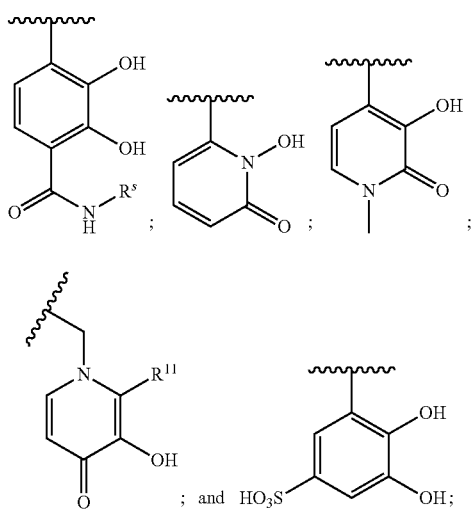

wherein $R^s$ comprises a solubilizing group; and
$R^{11}$ is methyl or ethyl.

In an exemplary embodiment, the invention provides a macrocycle having the structure:

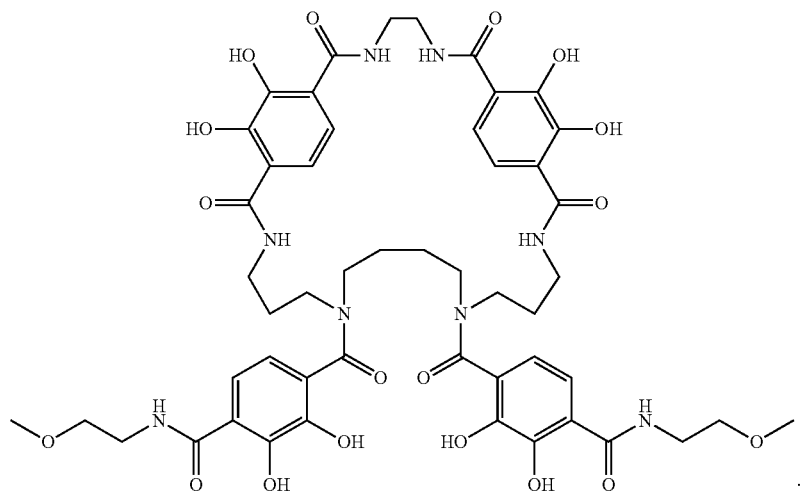

Complexes

In one aspect, the invention provides a complex of a macrocycle disclosed herein with a metal ion.

Any of the combinations of macrocycles disclosed herein and a metal ion disclosed herein are encompassed by this disclosure and specifically provided by the invention.

Metals

In some embodiments, the metal is an actinide. In some embodiments the metal is a lanthanide. In some embodiments, the metal is Th(IV). In some embodiments, the metal is $^{227}$Th. In some embodiments, the metal is $^{177}$Lu. In some embodiments, the metal is $^{225}$Ac. In some embodiments, the metal is $^{90}$Y. In some embodiments, the metal is $^{153}$Sm. In some embodiments, the metal is $^{166}$Ho. In some embodiments, the metal is Zr(IV). In some embodiments, the metal is Ln(III). In some embodiments, the metal is Ca(II). In some embodiments, the metal is Pr(III). In some embodiments, the metal is Ce(IV). In some embodiments, the metal is Am(IV). In some embodiments, the metal is Pu.

Radionuclides

The chelating moieties disclosed herein can be used to bind metal ions, in particular, a radionuclide. The term "radionuclide" or "radioisotope" refers to a radioactive isotope or element with an unstable nucleus that tends to undergo radioactive decay. Numerous decay modes are known in the art and include alpha decay, proton emission, neutron emission, double proton emission, spontaneous fission, cluster decay, β$^-$ decay, positron emission (β$^+$ decay), electron capture, bound state beta decay, double beta decay, double electron capture, electron capture with positron emission, double positron emission, isomeric transition and internal conversion.

Exemplary radionuclides include alpha-emitters, which emit alpha particles during decay. In some embodiments, a radionuclide is an emitter of a gamma ray or a particle selected from an alpha particle, an electron and a positron.

In some embodiments, the radionuclide is an actinide. In some embodiments, the radionuclide is a lanthanide. In some embodiments, the radionuclide is a 3$^+$ ion. In some embodiments, the radionuclide is a 4$^+$ ion. In some embodiments the radionuclide is a 2$^+$ ion.

Of particular use in the complexes provided herein are radionuclides selected from isotopes of U, Pu, Fe, Cu, Ce, Nd, Eu, Sm, Gd, Tb, Dy, Ho, Er, Yb, Lu, Y, Th, Zr, In, Ga, Bi, Ra and Ac. In some embodiments, one or more of these radionuclides are excluded. In some embodiments, a radionuclide is selected form radium-223, thorium-227, bismuth-213, Lutetium-177, and actinium-225. Other useful radioisotopes include bismuth-212, iodine-123, copper-64, iridium-192, osmium-194, rhodium-105, samarium-153, and yttrium-88, yttrium-90, and yttrium-91. In exemplary embodiments, the radionuclide is thorium, particularly selected from thorium-227 and thorium-232. In some embodiments, thorium-226 is excluded. In some embodiments, U is excluded. In some embodiments, uranium-230 is excluded. That is, in some embodiments, a radionuclide is not U, or a radionuclide is not uranium-230 or a radionuclide is not thorium-226. In exemplary embodiments, the radionuclide is cerium, particularly cerium-142 ($^{142}$Ce).

$^{232}$Th exists in nature as an α-emitter with a half life of 1.4×10$^{10}$ yr. In aqueous solution, Th(IV) is the only oxidation state. Thorium(IV) ion is bigger than Pu(IV) and usually forms complexes with 9 or higher coordination number. For example, the crystal structure of both Th(IV) complexes of simple bidentate 1,2-HOPO and Me-3,2-HOPO have been determined as nine coordinated species.

Similar to other actinide ions, thorium(IV) prefers forming complexes with oxygen, especially negative oxygen donor ligands. Thorium(IV) also prefers octadentate or higher multidentate ligands:

| Ligand | Acac | NTA | HEDTA* | EDTA** | DTPA | TTHA |
|---|---|---|---|---|---|---|
| Ligand Type | Bi-dentate | Tetra- | Hexa- | Hexa- | Octa- | Deca- |
| Log K$_1$ | 7.85 | 16.9 | 18.5 | 25.3 | 30.34 | 31.9 |

*with one alcoholic oxygen and three carboxyl groups;
**with four carboxyl groups.

Other radionuclides with diagnostic and therapeutic value that can be used with the compounds disclosed herein can be found, for example, in U.S. Pat. Nos. 5,482,698 and 5,601,800; and Boswell and Brechbiel, Nuclear Medicine and Biology, 2007 October, 34(7): 757-778 and the manuscript thereof made available in PMC 2008 October 1.

Exemplary Complexes

In an exemplary embodiment, the invention provides a complex comprising any of the exemplary macrocycles described above and Th(IV). In an exemplary embodiment, the invention provides a complex comprising any of the exemplary macrocycles described above and Ce(IV).

Linker to Functional/Targeting Moiety

A "linker", "linking member", or "linking moiety" as used herein is a moiety that joins or potentially joins, covalently or noncovalently, a first moiety to a second moiety. In particular, a linker attaches or could potentially attach a chelator described herein to another molecule, such as a targeting moiety. In some embodiments, a linker attaches or could potentially attach a chelator described herein to a solid support. A linker comprising a reactive functional group that can be further reacted with a reactive functional group on a structure of interest in order to attach the structure of interest to the linker is referred to as a "functionalized linker". In exemplary embodiments, a linker is a functionalized linker. In exemplary embodiments, a chelator comprises one or more functionalized linkers. In some embodiments, a linker comprises a targeting moiety. In some embodiments, a linker to a targeting moiety comprises a bond to the targeting moiety.

A linker can be any useful structure for that joins a chelator to a reactive functional group or a targeting moiety, such as an antibody. Examples of a linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary linkers include substituted or unsubstituted ($C_1$, $C_2$, $C_3$, $C_4$, $C_5$, $C_6$, $C_7$, $C_8$, $C_9$ or $C_{10}$) alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a linker includes at least one heteroatom. Exemplary linkers also include —C(O)NH—, —C(O), —NH—, —S—, —O—, and the like. In an exemplary embodiment, a linker is a heteroalkyl substituted with a reactive functional group.

Reactive Functional Groups

In one embodiment, a linker comprises a reactive functional group (or a "reactive functional moiety", used synonymously). The reactive functional group can be further reacted to covalently attach the linker to another structure, such as a targeting moiety or a solid support, for example. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in March, Advanced Organic Chemistry (3rd Ed., John Wiley & Sons, New York, 1985); Hermanson, Bioconjugate Techniques (Academic Press, San Diego, 1996); and Feeney et al., Modification of Proteins, Advances in Chemistry Series, Vol. 198 (American Chemical Society, Washington, D.C., 1982).

In some embodiments, a reactive functional group refers to a group selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds., Organic Functional Group Preparations, (Academic Press, San Diego, 1989)).

A reactive functional group can be chosen according to a selected reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Amines and Amino-Reactive Groups

In one embodiment, a reactive functional group is selected from an amine, (such as a primary or secondary amine), hydrazine, hydrazide and sulfonylhydrazide. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfur-NHS esters react preferentially with a primary (including aromatic) amino groups of a reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with amine groups of a molecule such as a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry*, 1981, 20: 4836-4842, e.g., teach how to modify a protein with carbodiimides.

Sulfhydryl and Sulfhydryl-Reactive Groups

In another embodiment, a reactive functional group is selected from a sulfhydryl group (which can be converted to disulfides) and sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

Other Reactive Functional Groups

Other exemplary reactive functional groups include:
(i) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(ii) hydroxyl groups, which can be converted to esters, ethers, aldehydes, etc.;
(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(iv) dienophile groups, which are capable of participating in Diels-Alder reactions such as, for example, maleimido groups;
(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(vi) alkenes, which can undergo, for example, cycloadditions, acylation, Michael addition, etc;
(vii) epoxides, which can react with, for example, amines and hydroxyl groups;
(ix) phosphoramidites and other standard functional groups useful in nucleic acid synthesis and
(x) any other functional group useful to form a covalent bond between the functionalized ligand and a molecular entity or a surface.

Functional Groups with Non-specific Reactivities

In addition to the use of site-specific reactive moieties, the present invention contemplates the use of non-specific reactive groups to link a chelator to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

Targeting Moiety

In exemplary embodiments, a linker joins a chelator to a targeting moiety. That is, in exemplary embodiments, a linker comprises a targeting moiety. In some embodiments, a chelator comprises a linker to a targeting moiety. Any linker described herein may be a linker comprising a reactive functional group that could react with a reactive functional group on a targeting moiety to join the linker to the targeting moiety. Any linker described herein may be a linker comprising a bond to a targeting moiety. The term "targeting moiety" refers to a moiety serves to target or direct the molecule to which it is attached (e.g. a chelator or a chelator complexed to a radionuclide) to a particular location or molecule. Thus, for example, a targeting moiety may be used to target a molecule to a specific target protein or enzyme, or to a particular cellular location, to a particular cell type or to a diseased tissue. As will be appreciated by those in the art, the localization of proteins within a cell is a simple method for increasing effective concentration. For example, shuttling an imaging agent and/or therapeutic into the nucleus confines them to a smaller space thereby increasing concentration. Finally, the physiological target may simply be localized to a specific compartment, and the agents must be localized appropriately.

The targeting moiety can be a small molecule (e.g., MW<500D), which includes both non-peptides and peptides. Examples of a targeting moiety also include peptides, polypeptides (including proteins, and in particular antibodies, which includes antibody fragments), nucleic acids, oligonucleotides, carbohydrates, lipids, hormones (including proteinaceous and steroid hormones), growth factors, lectins, receptors, receptor ligands, cofactors and the like. Targets of a targeting moiety can include a complementary nucleic acid, a receptor, an antibody, an antigen or a lectin, for example.

In exemplary embodiments, a targeting moiety can bind to a target with high binding affinity. In other words, a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant $K_d$ of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less. A compound may have a high binding affinity for a target if the compound comprises a portion, such as a targeting moiety, that has a high binding affinity for the target.

In exemplary embodiments, a targeting moiety is an antibody. An "antibody" refers to a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

While a targeting moiety may be appended to a chelator in order to localize the compound to a specific region in an animal, certain chelators have a natural affinity for cells, tissue, organs or some other part of the animal. For example, a chelator disclosed herein might have a natural or intrinsic affinity for bone. Thus, in some embodiments, a chelator, such as an open chelator or a macrocycle, does not comprise a targeting moiety or a linker to a targeting moiety. A chelator lacking a targeting moiety can be used in any method that does not require specific targeting.

In some embodiments, a chelator comprises a linker to a solid support. That is, any linker described herein may be a linker comprising a reactive functional group that could react with a reactive functional group on a solid support to join the linker to the solid support. Any linker described herein may be a linker comprising a bond to a solid support. A "solid support" is any material that can be modified to contain discrete individual sites suitable for the attachment or association of a chelator. Suitable substrates include biodegradable beads, non-biodegradable beads, silica beads, magnetic beads, latex beads, glass beads, quartz beads, metal beads, gold beads, mica beads, plastic beads, ceramic beads, or combinations thereof. Of particular use are biocompatible polymers, including biodegradable polymers that are slowly removed from the system by enzymatic degradation. Example biodegradable materials include starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. Other suitable substances for forming the particles exist and can be used. In some embodiments, a solid support is a bead comprising a cross-linked starch, for example, cross-linked potato starch. Beads made from starch are completely biodegradable in the body, typically by serum amylase, a naturally occurring enzyme found in the body. In these embodiments, the chelator optionally further comprises a targeting moiety or a linker to a targeting moeity. In cases where a chelator that is attached to a solid support does not comprise a targeting moiety, the cheaitor can be localized directly by the practitioner, for example, by direct surgical implantation.

In some embodiments, a linker has the structure -L$^{11}$-X, wherein L$^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a reactive functional group or a targeting moiety.

In some embodiments, L$^{11}$ is selected from substituted or unsubstituted alkyl and substituted or unsubstituted heteroalkyl. In some embodiments, L$^{11}$ is heteroalkyl. In some embodiments, L$^{11}$ is (C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$ or C$_{20}$) alkyl in which 1, 2 or 3 atoms are replaced with a heteroatom, such as nitrogen or oxygen.

In some embodiments, X is selected from —NH$_2$ and —CO(O)H.

In some embodiments, -L$^{11}$-X is selected from

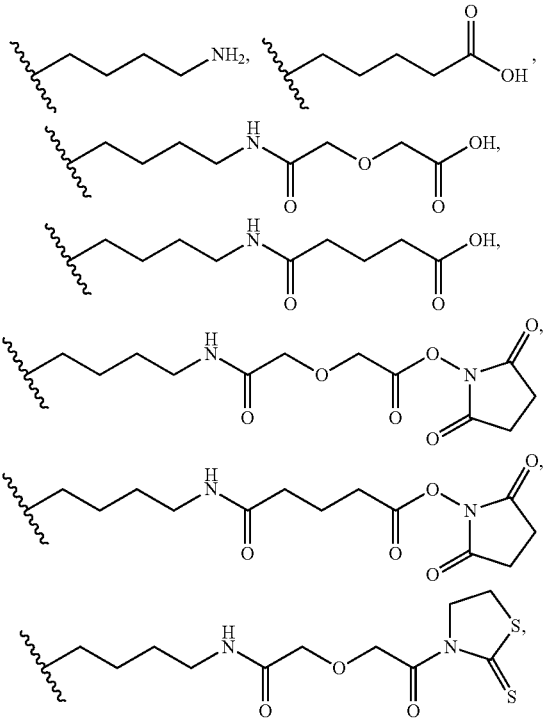

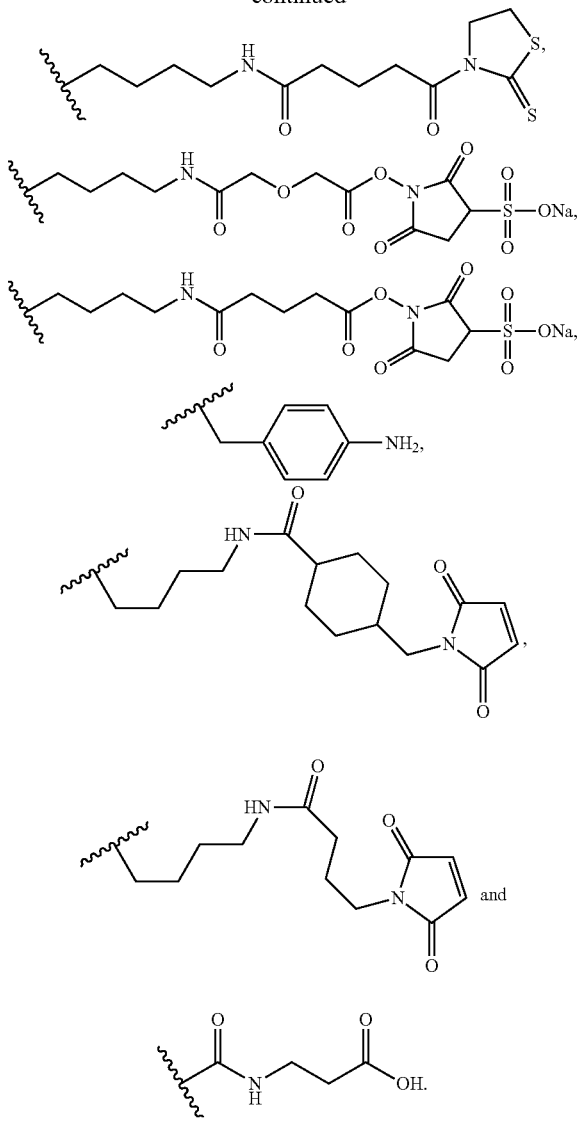

In exemplary embodiments, X is a targeting moiety.

In exemplary embodiments, a linker is a linker to a targeting moiety. In some embodiments, the targeting moiety is selected from a polypeptide, a nucleic acid, a lipid, a polysaccharide, a small molecule, a cofactor and a hormone. In exemplary embodiments, the targeting moiety is an antibody or antibody fragment.

In some embodiments, a linker includes an aliphatic carbon chain or a poly-ethyleneglycol (PEG) chain. Thus, a linker can comprise a structure selected from:

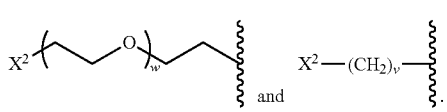

The integer v is selected from 1 to 20, and w is an integer from 1 to 1,000 or 1 to 500 or 1 to 100 or 1 to 50 or 1 to 10.

Exemplary $X^2$ groups include OH, alkoxy, and one of the following structures:

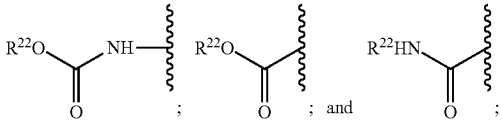

wherein $R^{22}$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The integer v is selected from 1 to 20, and w is an integer from 1 to 1,000 or 1 to 500 or 1 to 100 or 1 to 50 or 1 to 10.

In some embodiments, a linker has the structure:

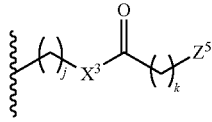

wherein $Z^5$ is selected from H, $OR^{23}$, $SR^{23}$, $NHR^{23}$, $OCOR^{24}$, $OC(O)NHR^{24}$, $NHC(O)OR^{23}$, $OS(O)_2OR^{23}$, and $C(O)R^{24}$. $R^{23}$ is selected from H, substituted or unsubstituted alkyl, and substituted or unsubstituted heteroalkyl. $R^{24}$ is selected from H, $OR^{25}$, $NR^{25}NH_2$, SH, $C(O)R^{25}$, $NR^{25}H$, substituted or unsubstituted alkyl and substituted or unsubstituted heteroalkyl. $R^{25}$ is selected from H, substituted or unsubstituted alkyl and substituted or unsubstituted alkyl. $X^3$ is selected from 0, S and $NR^{26}$, wherein $R^{26}$ is a member selected from H, substituted or unsubstituted alkyl and substituted or unsubstituted heteroalkyl. The integers j and k are members independently selected from 1, 2, 3, 4, 5, 6, 7, 8, 9, 10, 11, 12, 13, 14, 15, 16, 17, 18, 19 and 20. In some embodiments, the integers j and k are members independently selected from 1, 2, 3, 4, 5, 6.

In a linker with multiple reactive functional groups, a particular functional group can be chosen such that it does not participate in, or interfere with, the reaction controlling the attachment of the functionalized spacer component to another ligand component. Alternatively, the reactive functional group can be protected from participating in the reaction by the presence of a protecting group. Those of skill in the art understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Synthesis

Methods for synthesizing the chelating moieties disclosed herein are known in the art. See, for example, WO/2008/008797; U.S. Pat. No. 6,846,915; U.S. Pat. No. 7,404,912; and U.S. Pat. No. 5,010,191.

Any scaffold moiety can be derivatized with at least one linker, such as a functionalized linker. Thus, in one exemplary embodiment, a linker, such as a functionalized linker, can be attached to the scaffold moiety. In another exemplary embodiment, a linker, such as a functionalized linker, is attached to a chelating moiety. A functionalized linker can reacted to form a bond with a targeting moiety. The linker can also be attached to any other linker within a compound.

Scaffold moieties that include a linker can be prepared by the following exemplary methods.

Scheme 1.1. Reverse synthetic scheme for carboxyl functionalized H22 cap-amine.

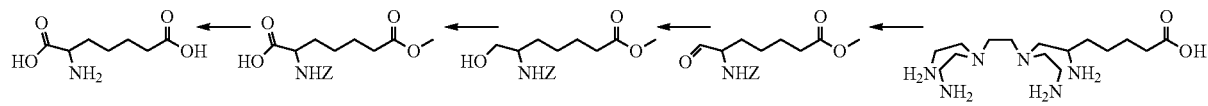

Other functionalized scaffolds include those in which the chiral carbon is placed on the central ethylene bridge of H22-amine. An exemplary route to such a scaffold initiates with 2,3-Diaminopropionic acid, as its carboxyl group is connected directly to the amine backbone to give a very rigid geometry, extended carboxyl chain is needed to provide flexibility for eventual protein conjugating. A synthetic scheme to the scaffold is shown in scheme 1.2.

Scheme 1.2

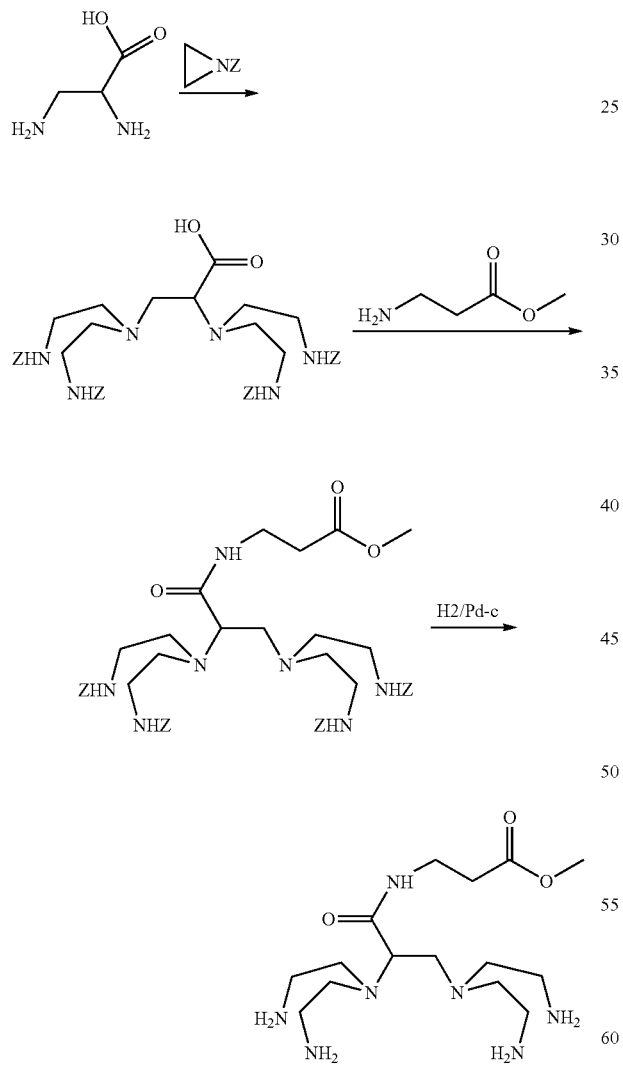

Scheme 1.3

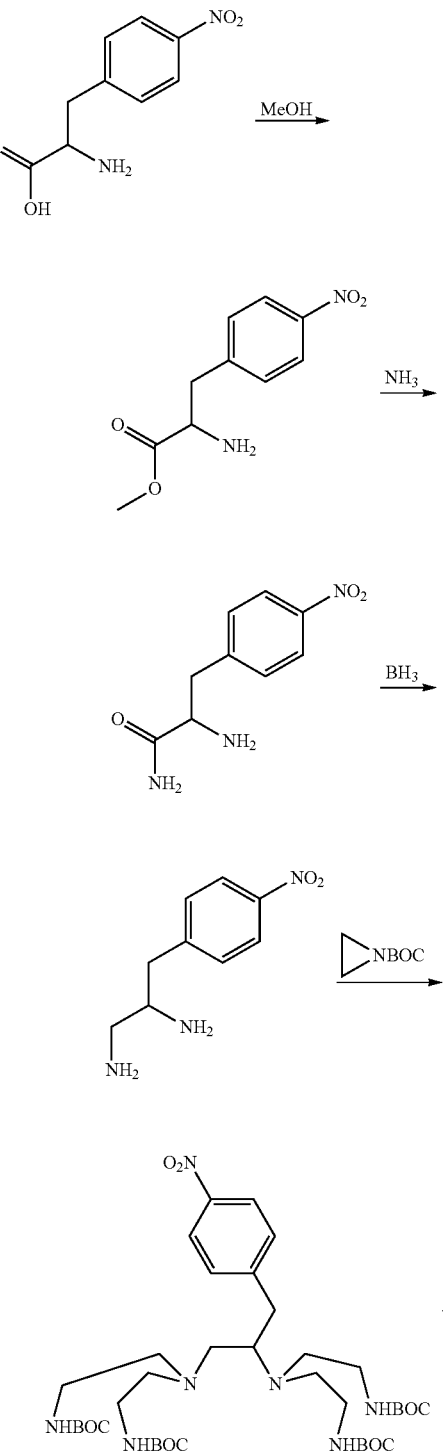

Variations on this synthesis include the use of a nitrophenylalanine or a BOC-amino group, which are optionally converted to carboxyl groups. Synthetic routes to these scaffolds are shown in Schemes 1.3 and 1.4.

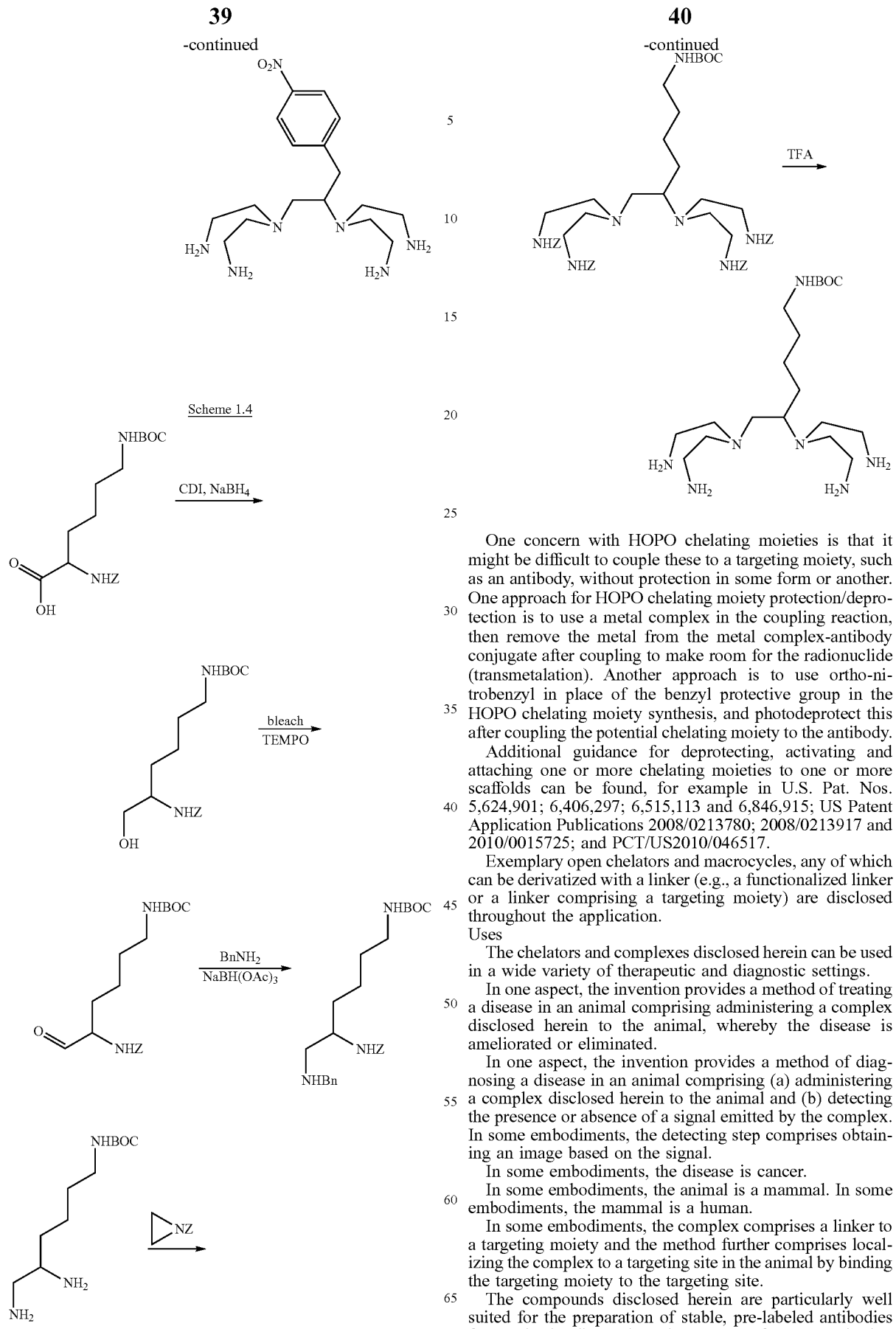

One concern with HOPO chelating moieties is that it might be difficult to couple these to a targeting moiety, such as an antibody, without protection in some form or another. One approach for HOPO chelating moiety protection/deprotection is to use a metal complex in the coupling reaction, then remove the metal from the metal complex-antibody conjugate after coupling to make room for the radionuclide (transmetalation). Another approach is to use ortho-nitrobenzyl in place of the benzyl protective group in the HOPO chelating moiety synthesis, and photodeprotect this after coupling the potential chelating moiety to the antibody.

Additional guidance for deprotecting, activating and attaching one or more chelating moieties to one or more scaffolds can be found, for example in U.S. Pat. Nos. 5,624,901; 6,406,297; 6,515,113 and 6,846,915; US Patent Application Publications 2008/0213780; 2008/0213917 and 2010/0015725; and PCT/US2010/046517.

Exemplary open chelators and macrocycles, any of which can be derivatized with a linker (e.g., a functionalized linker or a linker comprising a targeting moiety) are disclosed throughout the application.

Uses

The chelators and complexes disclosed herein can be used in a wide variety of therapeutic and diagnostic settings.

In one aspect, the invention provides a method of treating a disease in an animal comprising administering a complex disclosed herein to the animal, whereby the disease is ameliorated or eliminated.

In one aspect, the invention provides a method of diagnosing a disease in an animal comprising (a) administering a complex disclosed herein to the animal and (b) detecting the presence or absence of a signal emitted by the complex. In some embodiments, the detecting step comprises obtaining an image based on the signal.

In some embodiments, the disease is cancer.

In some embodiments, the animal is a mammal. In some embodiments, the mammal is a human.

In some embodiments, the complex comprises a linker to a targeting moiety and the method further comprises localizing the complex to a targeting site in the animal by binding the targeting moiety to the targeting site.

The compounds disclosed herein are particularly well suited for the preparation of stable, pre-labeled antibodies for use in the diagnosis and treatment of cancer and other diseases. For example, antibodies expressing affinity for specific tumors or tumor-associated antigens are labeled with a diagnostic radionuclide-complexed chelate, and the labeled antibodies can be further stabilized through lyophilization. Where a chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. A stable, lyophilized, radiolabeled antibody can be reconstituted with suitable diluent at the time of intended use, thus greatly simplifying the on site preparation process. The methods of the invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available.

Exemplary embodiments are summarized herein below.

In an exemplary embodiment, the invention provides a macrocycle having the structure:

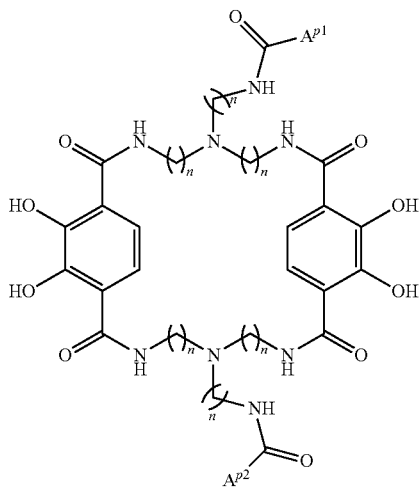

wherein $A^{p1}$ and $A^{p2}$ are independently selected from

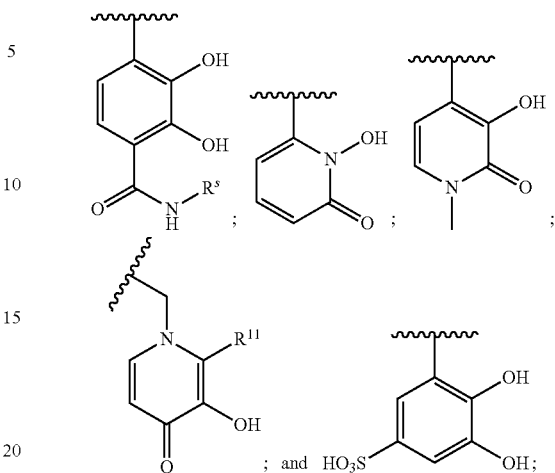

wherein $R^s$ comprises a solubilizing group; and $R^{11}$ is methyl or ethyl; and each n is an integer independently selected from 2 and 3.

In an exemplary embodiment, according to the above paragraph, $A^{p1}$ and $A^{p2}$ are each

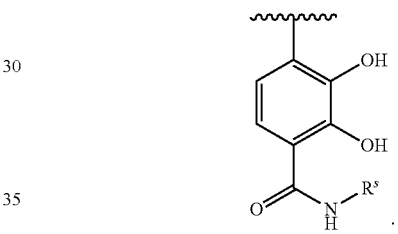

In an exemplary embodiment, according to any of the above paragraphs, the macrocycle has a structure selected from

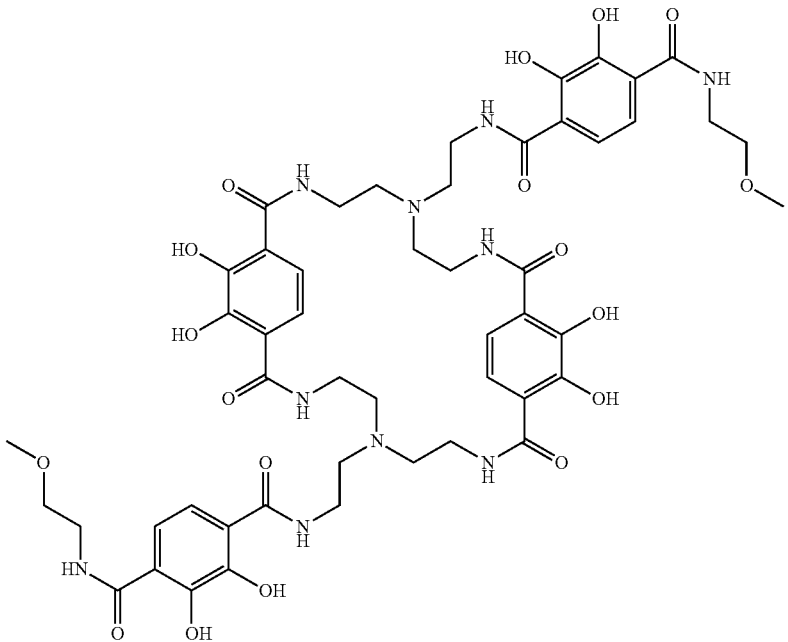

and

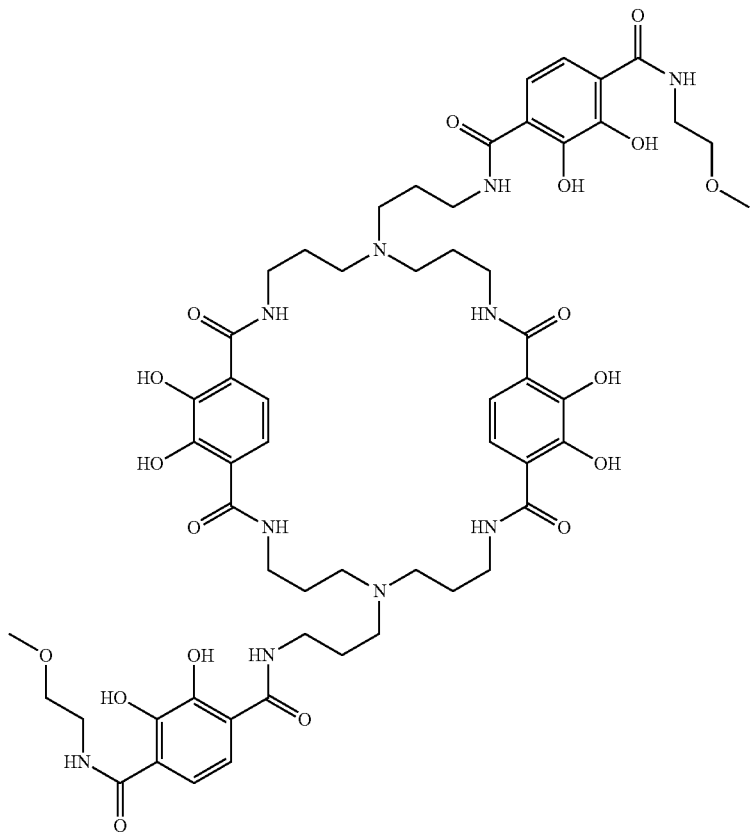

In an exemplary embodiment, the invention provides a complex comprising a macrocycle according to any of the above paragraphs and a metal ion.

In an exemplary embodiment, according to the above paragraph, the metal is a radionuclide.

In an exemplary embodiment, according to any of the above paragraphs, the radionuclide is Thorium (Th).

In an exemplary embodiment, according to any of the above paragraphs, the radionuclide is Cerium (Ce).

The following examples are provided to illustrate selected embodiments of the invention and are not to be construed as limiting its scope.

EXAMPLES

Synthesis

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention; it is not intended to limit the scope of reactions or reaction sequences that are useful in preparing the compounds of the present invention.

General.

All chemicals were used as obtained without further purification, unless otherwise noted. Characterization data was obtained at facilities at the University of California, Berkeley. NMR spectra were obtained at room temperature on Bruker AVB-400, AV-500, or AV-600 spectrometers in the NMR Facility in the College of Chemistry. Chemical shifts are referenced to solvent residual peaks. Elemental analyses were performed by the Microanalytical Laboratory in the College of Chemistry, and mass spectra (by high resolution electrospray ionization) were obtained by the QB3/Chemistry Mass Spectrometry Facility. Silica gel (230-400 mesh) was used for column chromatography purifications.

Example 1

Synthesis of phi(2,2)moeTAM

Scheme. Synthesis of TAM-dithiaz.

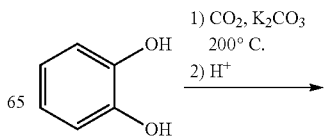

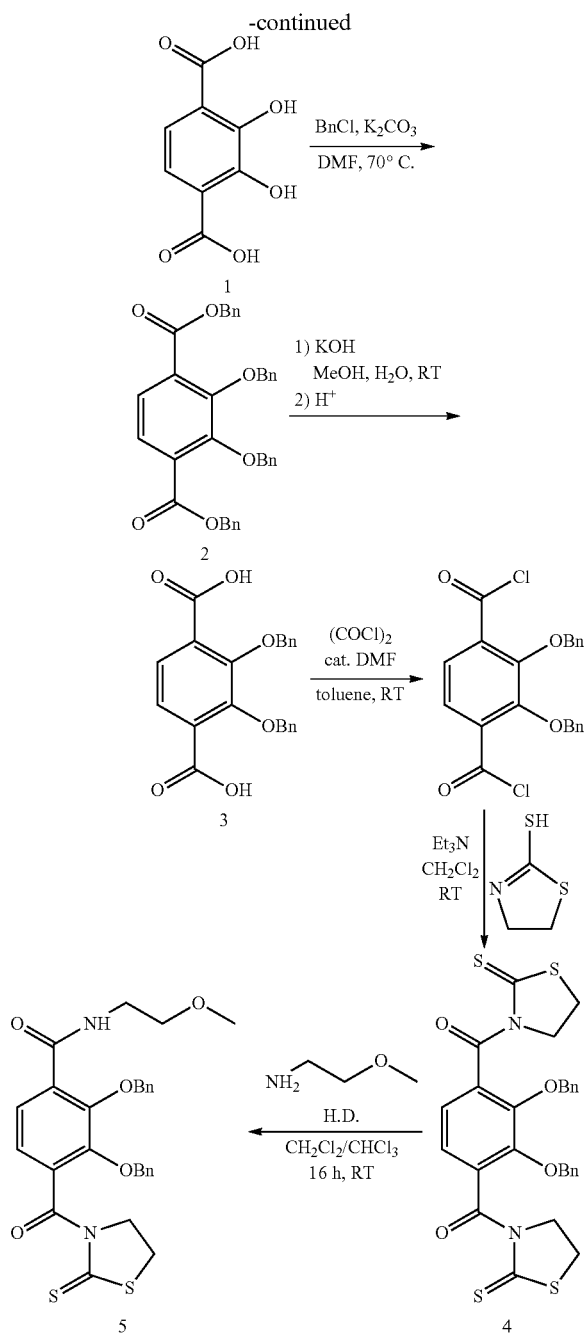

2,3-dihydroxyterephthalic acid (1).

On a warm, sunny day (28° C., 18% humidity), catechol (TCI, 120.033 g, 1.09 mol) and $K_2CO_3$ (316 g, 2.29 mol) were ground together, and the homogeneous mixture was poured into a 500-mL beaker, which was placed in a par-bomb. The bomb was purged three times with 600 psi $CO_2$ before being filled to 860 psi $CO_2$ and placed in an oil bath. The oil bath gradually increased in temperature to 225° C. in 3 h, with an accompanying increase in bomb pressure to 1170 psi. Within 1.25 h, the pressure decreased to 380 psi (250° C.), and the temperature was maintained at 230° C. for 15 hours. The bomb, at 160 psi, was let cool to RT (and placed in the freezer to facilitate opening) and opened. The reaction mixture, a hard gray rock with turquoise and white specks, was combined with 1.5 L water and 1 L conc. HCl. The mixture slowly bubbled and produced beige foam, and after 3 h, the solid chunks were broken apart with a stick and stirred with a magnetic stir bar for 2 h. The beige slurry was then filtered and left to dry on the house vacuum for 14 h. The solid light gray solid was washed with 4 L Millipore water, and left on the house vacuum for 9 days. The dried gray solid was ground to a powder and further dried on the vacuum line for 26 h (95%).

$^1$H NMR (400 MHz, MeOD, δ): 7.34 (s, Ar H, 2H).

$^{13}$C NMR (101 MHz, MeOD, δ): 117.8, 120.1, 152.6, 173.2.

HRMS-ESI (m/z): [M−H]$^-$ calcd for $C_8H_5O_6$, 197.0092. found, 197.0094.

Dibenzyl 2,3-bis(benzyloxy)terephthalate (2).

1 (101.798 g, 0.514 mol), benzyl chloride (258 mL, 2.242 mol), KI (25.304 g, 0.140 mol), $K_2CO_3$ (664.270 g, 4.806 mol), and 1.3 L DMF were combined in a 5-L 3-neck round-bottom flask, yielding a mixture of dark brown solution and undissolved solid. The flask was fitted with a reflux condenser and mechanical stirrer, and placed in a heating mantle. The reaction mixture was heated at 67° C. for 3 d and filtered. The dark brown, clear filtrate was rotovapped to ~400 mL of opaque, brown, viscous oil, which was dissolved in ~600 mL DCM. The opaque, brown solution was filtered and extracted with water (5×500 mL). A small amount of brine was used to break up emulsions. The organic layer was dried with $MgSO_4$ and rotovapped to ~250 mL of dark brown oil. This oil was purified by silica column chromatography (0-5% MeOH in DCM) to yield a hardened brown oil (48%).

$^1$H NMR (500 MHz, CDCl$_2$, δ): 5.10 (s, Bn CH$_2$, 4H), 5.33 (s, COOBn H, 4H), 7.25-7.44 (m, Ph H, 20H), 7.58 (s, Ar H, 2H).

$^{13}$C NMR (151 MHz, CDCl$_2$, δ): 67.8, 70.1, 76.9, 126.1, 128.6, 128.8, 128.9, 129.0, 129.1, 131.0, 136.4, 137.5, 153.4, 165.6.

HRMS-ESI (m/z): [M+H]$^+$ calcd for $C_{36}H_{31}O_6$, 559.2115. found, 559.2116.

2,3-bis(benzyloxy)terephthalic acid (3).

2 (56.970 g, 0.102 mol) was dissolved in 200 mL 1:1: EtOH:dioxane in a 1-L round-bottom flask, resulting in a dark orange, clear solution, to which a suspension of LiOH (7.315 g, 0.305 mol) in 75 mL water was added. The flask was fitted with a reflux condenser and magnetically stirred. The emulsion (containing undissolved LiOH) was heated to 60° C. for 12 h, and became a translucent, orange solution. The reaction mixture was filtered through a M glass frit, dissolved in 500 mL basic water, and washed with DCM (3×250 mL). The aqueous layer was acidifed with ~80 mL conc. HCl, and the resulting white precipitate was filtered and washed with water. The solid was dried using house vacuum overnight, ground into a white powder, and dried on the vacuum line for 12 h (100%).

$^1$H NMR (600 MHz, DMSO-d$_6$, δ): 5.03 (s, Bn CH$_2$, 4H), 7.33-7.41 (m, Ph H, 10H), 7.49 (s, Ar H, 2H), 13.31 (s, COOH, 2H).

$^{13}$C NMR (151 MHz, DMSO-d$_6$, δ): 75.6, 124.9, 128.0, 128.2, 128.2, 131.0, 136.9, 151.4, 166.7.

HRMS-ESI (m/z): [M−H]$^-$ calcd for $C_{22}H_{17}O_6$, 377.1031. found, 377.1030.

(2,3-bis(benzyloxy)-1,4-phenylene)bis((2-thioxothiazolidin-3-yl)methanone) (4).

An opaque, beige suspension of 3 (10.435 g, 27.58 mmol) in 80 mL dry toluene was stirred an degassed with $N_2$. Oxalyl chloride (8.00 mL, 94.5 mmol) was added via syringe, and the reaction mixture bubbled. The addition of 3 drops of DMF resulted in more vigorous bubbling. The next day, the reaction mixture was a still an opaque slurry, with no bubbling. 20 mL toluene was added to dilute the mixture, and as a few drops DMF did not result in bubbling, 3.0 mL (16 mmol) oxalyl chloride was added, and the reaction bubbled. The following day, 4.5 mL (24 mmol) oxalyl chloride was added to the reaction mixture, which became a translucent, yellow solution. The addition of another 2.0 mL (11 mmol) oxalyl chloride did not result in additional bubbling, and the reaction was let stir overnight. The following day, the reaction mixture had become a clear, orange solution containing a small amount of white solid settled at the bottom of the flask. The toluene and excess oxalyl chloride were removed by rotary evaporation, and the brown cake was dissolved in 50 mL DCM. This opaque, orange solution was dripped via teflon cannula into a stirring, 0° C. (ice-water bath) solution of 2-mercaptothiazoline (7.2682 g, 60.97 mmol) in 50 mL DCM and 14 ml triethylamine. Following the addition and the melting of the ice bath, the reaction was let stir at RT overnight. The dark orange, clear solution was filtered, washed with water (3×330 mL), and washed with aqueous 2M HCl (4×250 mL). The organic layer was dried with $MgSO_4$ and rotovapped to a brown oil, which was purified by silica column chromatography (DCM). The product, as a 20 mL yellow DCM solution, was precipitated from 1 L isopropanol at 4° C. Filtration afforded a yellow solid (43%).

$^1$H NMR (500 MHz, $CDCl_2$, δ): 3.04 (t, J=5.8 Hz, $NCH_2CH_2S$, 4H), 4.35 (t, J=6.0 Hz, $NCH_2CH_2S$, 4H), 5.10 (s, Bn $CH_2$, 4H), 7.18 (s, Ar H, 2H), 7.38 (m, Ph H, 10H).

$^{13}$C NMR (151 MHz, $CDCl_2$, δ): 29.4, 56.2, 76.4, 124.8, 128.8, 128.9, 129.0, 133.8, 137.4, 149.5, 167.0, 202.0.

BnTAM(thiaz)(OMeEtN) (5).

A solution of 2-methoxyethanamine (0.35 mL, 4.03 mmol) in 200 mL chloroform (with four drops of triethylamine) was added dropwise to a stirring solution of BnTAM(thiaz)$_2$ (4) (30.010 g, 51.7 mmol) in 1000 mL dichloromethane. The high-dilution slow addition was performed at room temperature over 16 hours. The reaction mixture was then directly applied onto a gradient silica column (0-10% methanol in dichloromethane), and the desired product was eluted with 8% methanol. Rotary evaporation gave a yellow, foamy solid that became an oil upon storage in the cold room.

$^1$H NMR (500 MHz, $CD_2Cl_2$): δ 3.03 (t, J=9.0 Hz, 1H, methoxyethanamide $CH_2$), 3.24 (s, 3H, $CH_3$), 3.39-3.42 (m, 2H, thiaz $CH_2$), 3.47-3.51 (m, 2H, methoxyethanamide $CH_2$), 4.40 (t, J=9.3 Hz, 2H, thiaz $CH_2$), 5.11 (s, 2H, Bn $CH_2$), 5.12 (s, 2H, Bn $CH_2$), 7.19 (d, J=10.5 Hz, 1H, ArH), 7.35-7.43 (m, 10H, Ph), 7.84 (d, J=10.5 Hz, 1H, ArH), 8.01 (br t, 1H, amide H).

$^{13}$C NMR (100 MHz, $CD_2Cl_2$): δ 28.8, 39.5, 55.7, 58.4, 70.8, 76.1, 76.7, 124.0, 126.4, 128.1, 128.4, 128.6, 128.6, 128.6, 128.9, 130.3, 133.6, 135.9, 137.1, 149.6, 150.2, 163.9, 166.7, 201.7.

(+)-HR ESIMS calcd for $C_{28}H_{29}O_5N_2S_2$(M+H): 537.1512. found: m/z 537.1518.

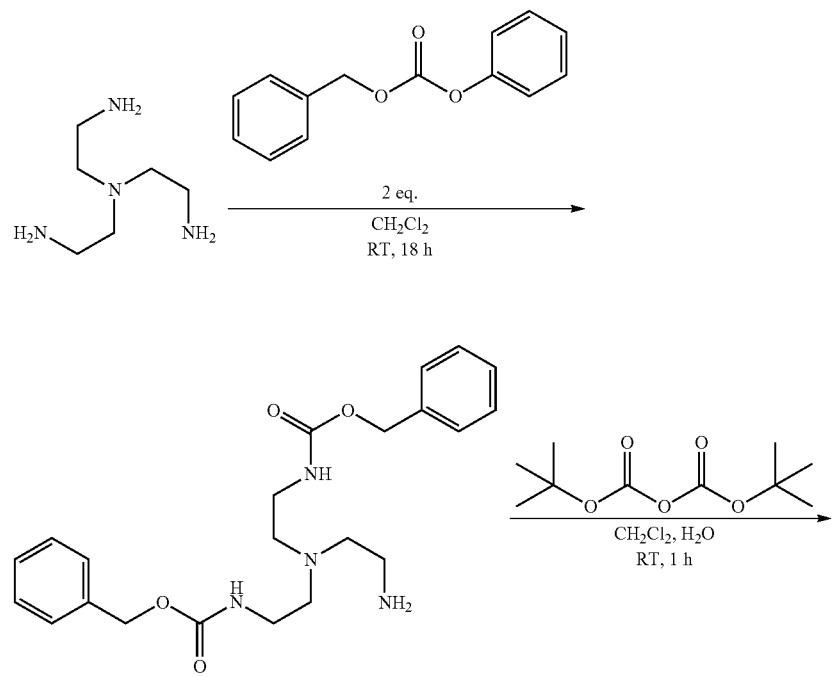

Scheme. Synthesis of Mono(Boc)tren.

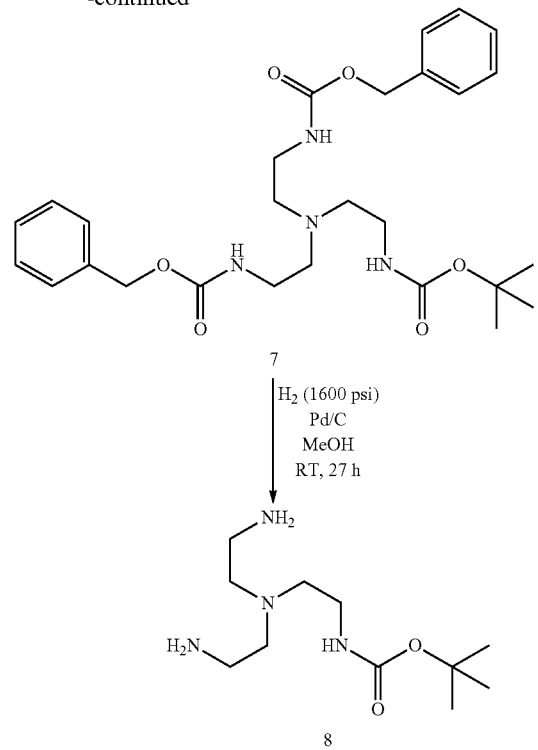

Dibenzyl(((2-aminoethyl)azanediyl)bis(ethane-2,1-diyl))dicarbamate (6).

Tren (TCI, 7.0 mL, 46.8 mmol) was added to 50 mL degassed DCM. Benzyl phenyl carbamate (20.5 mL, 103.8 mmol) was added dropwise to the cooled (ice-water bath), stirring solution of tren. Following melting of the ice bath, the reaction was let stir at RT for 12 h. The clear, light yellow reaction mixture was reduced to a yellow oil by rotary evaporation and purified by silica column chromatography (5-15% MeOH in DCM). The product fractions were rotovapped to a light yellow, translucent oil and further dried on the vacuum line for 8 h with light (50° C.) heating (72%).

$^1$H NMR (600 MHz, CDCl$_2$, δ): 2.45-2.65 (m, —NCH$_2$CH$_2$NH$_2$ and —NCH$_2$CH$_2$NHCbz, 8H), 3.24 (s, —NCH$_2$CH$_2$NHCbz, 4H), 5.11 (s, Bn CH$_2$, 4H), 5.16 (br s, amine H, 1H), 6.57 (s, amide H, 2H), 7.33-7.36 (m, Ph H, 10H).

$^{13}$C NMR (151 MHz, CDCl$_2$, δ): 39.7, 40.0, 49.5, 54.5, 57.3, 66.6, 116.2, 119.2, 128.2, 128.7, 128.8, 129.8, 137.7, 157.3, 158.4.

HRMS-ESI (m/z): [M+H]$^1$ calcd for C$_{22}$H$_{31}$O$_4$N$_4$, 415.2340. found, 415.2333.

Dibenzyl tert-butyl(nitrilotris(ethane-2,1-diyl))tricarbamate (7).

A solution of NaCl (4.789 g, 81.95 mmol) and NaHCO$_3$ (2.997 g, 35.67 mmol) in 60 mL water was added to a solution of 6 (10.2754 g, 24.05 mmol) in 50 mL DCM. Boc anhydride (5.7373 g, 26.29 mmol) dissolved in 10 mL DCM was added to the biphasic mixture, resulting in immediate bubbling. The reaction was let stir at RT overnight, filtered, and extracted with DCM (3×40 mL). The combined organic extracts were rotovapped to a viscous, clear, light yellow oil that was purified by silica column chromatography (0-10% MeOH in DCM). The product fractions were rotovapped to a clear, yellow, viscous oil (84%).

$^1$H NMR (500 MHz, CDCl$_2$, δ): 1.36 (s, t-Bu, 9H), 2.51 (br t, —NCH$_2$CH$_2$NHBoc, 2H), 2.54 (br t, —NCH$_2$CH$_2$NHCbz, 4H), 3.10 (br t, —NCH$_2$CH$_2$NHBoc, 2H), 3.19 (br t, —NCH$_2$CH$_2$NHCbz, 4H), 5.05 (s, Bn H, 4H), 5.10 (br s, RNHBoc, 1H), 5.55 (br s, RNHCbz, 2H), 7.28-7.32 (m, Ph H, 10H).

$^{13}$C NMR (151 MHz, CDCl$_2$, δ): 28.7, 39.2, 39.6, 54.6, 54.9, 66.9, 79.5, 128.4, 128.5, 128.9, 139.7, 157.2.

HRMS-ESI (m/z): [M+H]$^+$ calcd for C$_{27}$H$_{39}$O$_6$N$_4$, 515.2864. found, 515.2847.

Tert-butyl(2-(bis(2-aminoethyl)amino)ethyl)carbamate (8).

7 (11.220 g, 20.20 mmol) was dissolved in 120 mL MeOH in a glass vessel containing a magnetic stir bar. A 5 mL MeOH solution of Pd/C (Aldrich, 10 wt %, 1.1318 g) was added to the solution of 7 and the glass vessel was placed in a par-bomb. The bomb was purged 3 times with 750 psi H$_2$ before being filled to 1250 psi H$_2$. The reaction was stirred at room temperature for 24 h with a sustained pressure of 1000 psi (the bomb leaked a bit). The reaction mixture was then filtered through a F glass frit and rotovapped to a light yellow, viscous oil. The oil was coevaporated with MeOH on the vacuum line and dried for 24 h. NMR showed the presence of carbonate in the product, which was then dissolved in water and purified by elution through an ion-exchange column (Dowex 21K XLT resin). Rotary evaporation afforded a clear, yellow oil (90%), which was stored at 4° C. as a DCM solution containing 1 mol equivalent triethylamine.

$^1$H NMR (500 MHz, CDCl$_2$, δ): 1.38 (s, t-Bu, 9H), 2.44-2.49 (m, —NCH$_2$CH$_2$NH$_2$ and —NCH$_2$CH$_2$NHBoc, 6H), 2.66 (t, J=6.0 Hz, 4H), 3.10 (br q, —NCH$_2$CH$_2$NHBoc, 2H), 5.78 (br t, amine H, 1H).

$^{13}$C NMR (151 MHz, CDCl$_2$, δ): 28.7, 39.3, 40.0, 51.6, 57.8, 79.1, 156.8.

HRMS-ESI (m/z): [M+H]$^+$ calcd for C$_{11}$H$_{27}$O$_2$N$_4$, 247.2129. found, 247.2127.

Scheme. Synthesis of phi(2,2)moeTAM.
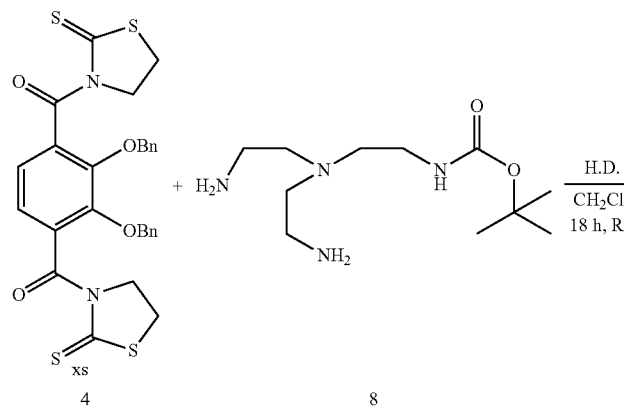
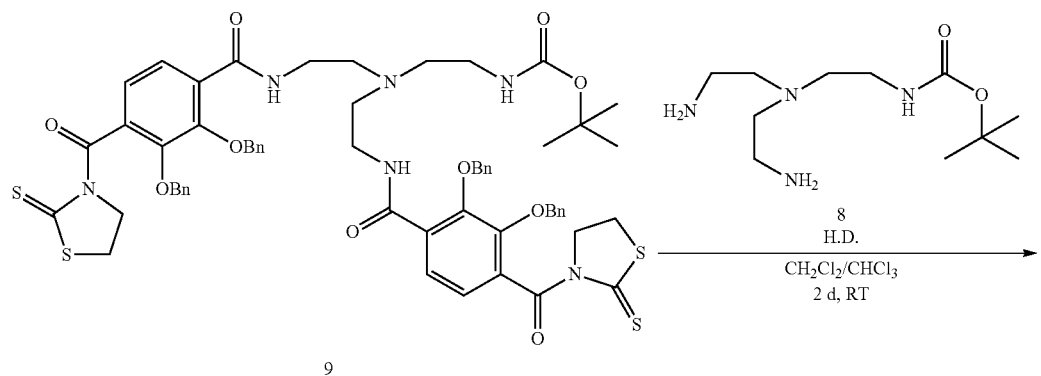
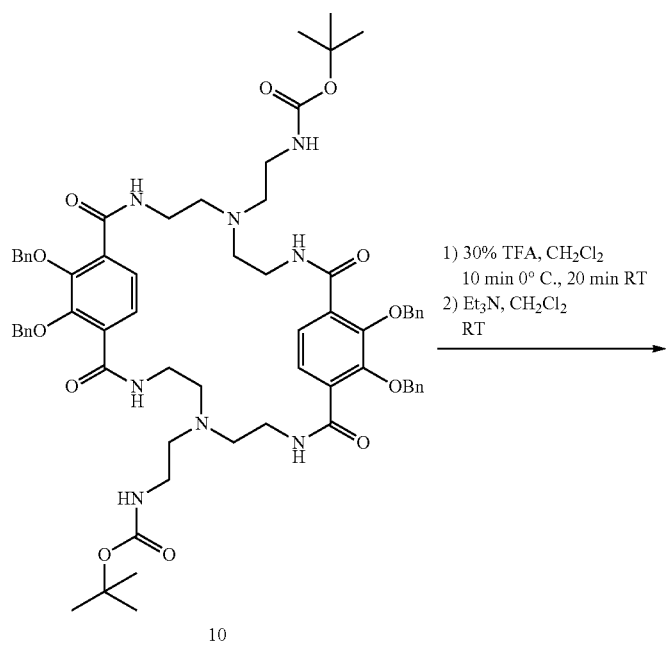

-continued
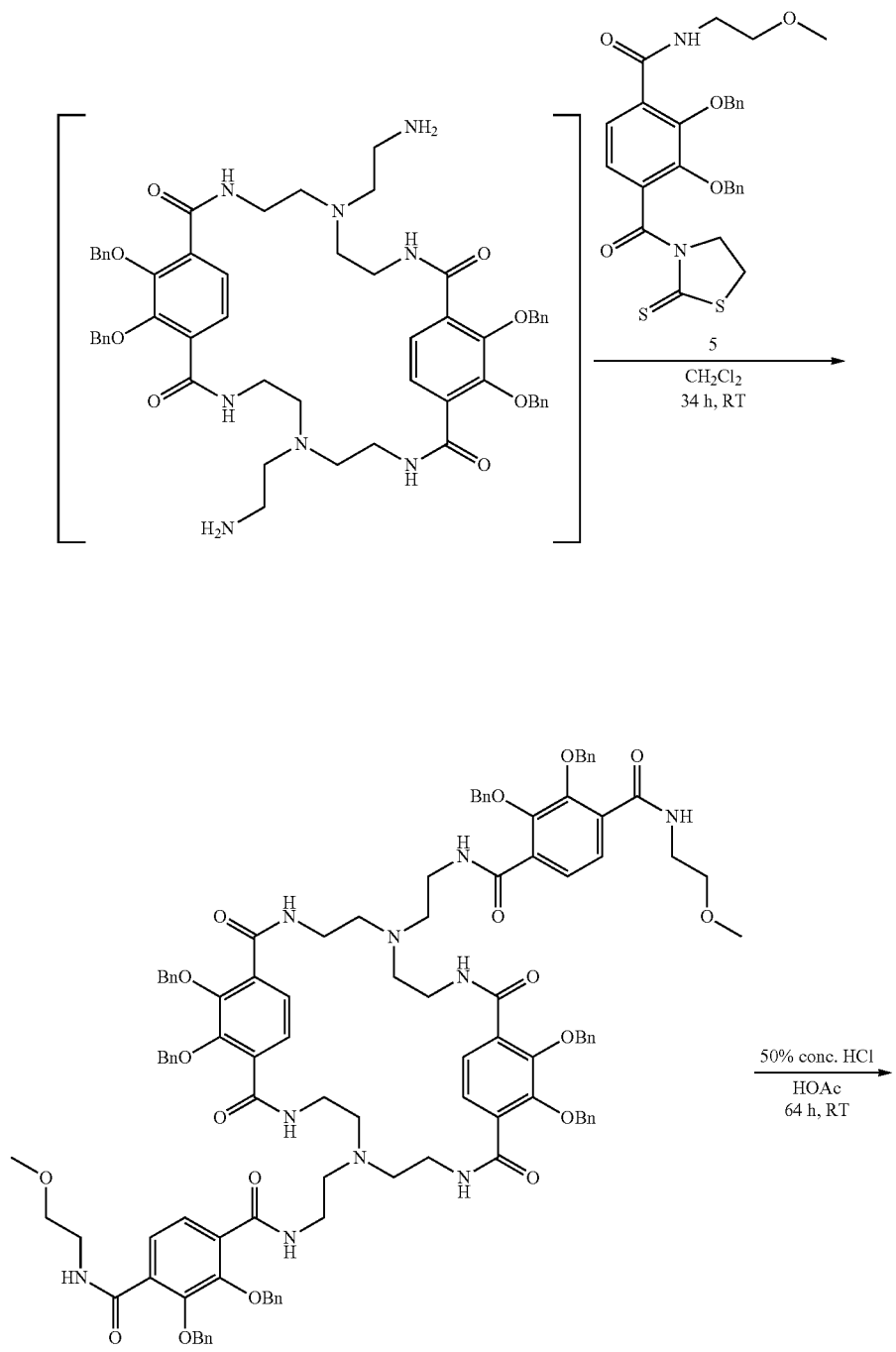

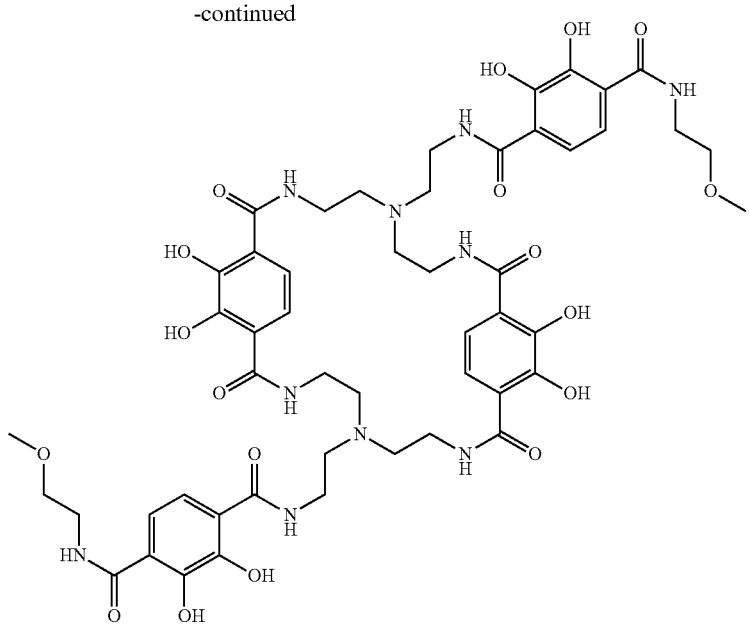

12

TrenBoc(BnTAMthiaz)$_2$ (9).

A solution of tren(Boc) 8 (0.2792 g, 1.13 mmol) in 200 mL dichloromethane (with three drops of triethylamine) was added dropwise to a stirring solution of 4 (<27.7 g, <47.7 mmol) in 500 mL dichloromethane (with 5 drops triethylamine). The high-dilution slow addition was performed at room temperature over 18 hours. The reaction mixture was reduced in volume by rotary evaporation and separated by gradient silica column chromatography (2-5% methanol in dichloromethane). 9 was eluted with 4% methanol, and was a yellow foamy solid after removal of solvent in vacuo (0.8765 g, 66%).

$^1$H NMR (500 MHz, CD$_2$Cl$_2$): δ 1.36 (s, 9H, CH$_3$), 2.39 (t, J=6.5 Hz, 4H, tren CH$_2$), 2.46 (t, J=6.0 Hz, 2H, tren CH$_2$), 2.99 (d, J=6.0 Hz, 2H, tren CH$_2$), 3.03 (t, J=7.3, 4H, tren CH$_2$), 3.23 (q, J=6.2 Hz, 4H, thiaz CH$_2$), 4.40 (t, J=7.5 Hz, 4H, thiaz CH$_2$), 5.031 (br t, 1H, amide H), 5.10 (s, 4H, Bn CH$_2$), 5.12 (s, 4H, Bn CH$_2$), 7.17 (d, J=8.0 Hz, 2H, ArH), 7.35-7.39 (m, 20H, Ph), 7.70 (d, J=8.0 Hz, 2H, ArH), 7.76 (br t, 2H, amide H).

$^{13}$C NMR (100 Hz, CD$_2$Cl$_2$): δ 28.2, 28.9, 37.6, 55.7, 76.2, 76.8, 124.1, 126.2, 128.1, 128.4, 128.6, 128.7, 128.8, 128.9, 130.7, 133.4, 136.0, 137.1, 149.5, 150.1, 164.2, 166.7, 201.7.

(+)-HR ESIMS calcd for C$_{61}$H$_{65}$O$_{10}$N$_6$S$_4$ (M+H): 1169.3640. found m/z 1169.3617.

(TrenBoc)$_2$(BnTAM)$_2$ (10).

Two 450 mL chloroform solutions, one of 9 (0.8503 g, 0.727 mmol) with 5 drops triethylamine and one of 8 (0.19981 g, 0.811 mmol) d with 15 drops triethylamine, were combined by dropwise addition into a flask containing 1000 mL dichloromethane. The high-dilution addition took place over two days at room temperature. The reaction mixture became progressively less yellow, as the BnTAMthiaz is yellow, but the thiazolidine and TAM are colorless in solution. Since the reaction was still yellow once the addition was complete, an excess of diethylenetriamine (1 mL, 9 mmol) was added to the reaction mixture to facilitate separation from remaining 9, as the addition of a primary amine renders its R$_f$ on silica much lower. After 1.5 hours, the reaction mixture had become colorless. It was directly applied on a flash gradient silica column (0-3% methanol in dichloromethane). The desired fractions were eluted with 3% methanol, rotary evaporated, and dried in vacuo to afford a white solid (0.7468 g, 87%).

$^1$H NMR (500 MHz, CD$_2$Cl$_2$): δ 1.33 (s, 18H, CH$_3$), 2.45 (br t, 4H, tren CH$_2$), 2.54 (t, J=5.3 Hz, 8H, tren CH$_2$), 2.99 (br q, 4H, tren CH$_2$), 3.38 (q, J=5.2 Hz, 8H, tren CH$_2$), 4.92 (br s, 2H, amide H), 5.03 (s, 8H, Bn CH$_2$), 7.10 (s, 4H, ArH), 7.36 (m, 20H, Ph), 7.67 (br s, 4H, amide H).

$^{13}$C NMR (100 MHz, CD$_2$Cl$_2$): δ 28.1, 37.1, 37.7, 52.6, 76.7, 78.7, 125.1, 128.4, 128.5, 128.6, 131.8, 136.6, 150.4, 155.8, 165.7.

(+)-HR ESIMS calcd for C$_{66}$H$_{81}$O$_{12}$N$_{18}$ (M+H)=1177.5968. found m/z 1177.5962.

Tren$_2$(BnTAM)$_2$[BnTAM(OMeEtN)]$_2$ (11).

A solution of 10 (0.26435 g, 0.225 mmol) in 7 mL dichloromethane was placed in an ice-water bath and stirred. 3 mL trifluoroacetic acid was added dropwise over ~5 min., and the reaction progress was monitored by TLC. The reaction mixture was left at 0° C. for 10 min and at room temperature for 20 min. While still stirring, the reaction mixture was dried in vacuo, affording a pink-orange oil that was redissolved in 2 mL dichloromethane and subsequently dried in vacuo (this was performed twice). 1 mL triethylamine and 1 mL dichloromethane were added to the foamy oil at 0° C., and the mixture was stirred at room temperature for 45 min. before the addition of a solution of 5 (0.56 g, 1.05 mmol) in 8 mL dichloromethane. The reaction mixture was stirred at room temperature for 34 h. Separation of the desired product from triethylamine was achieved by extraction with 10 mL water. The aqueous layer was acidified to pH 8 (from pH 10) with HCl and extracted with three 5 mL portions of dichloromethane. The combined organic layers were rotary evaporated and applied onto a gradient silica column (1-5% methanol in dichloromethane). The product was eluted with 5% methanol and further purified on a silica chromatron plate. The by-products were eluted with 2.5% methanol in dichloromethane, and a slow gradient to 6% was used to collect the desired product. Rotary evaporation resulted in a light yellow foamy solid (0.32466 g, 80%).

$^1$H NMR (500 MHz, CD$_2$Cl$_2$): δ 2.45 (t, J=8.0 Hz, 4H, tren CH$_2$), 2.58 (t, J=6.0 Hz, 8H, tren CH$_2$), 3.21 (s, 6H, CH$_3$), 3.23-3.28 (m, 4H, methoxyethanamine CH$_2$), 3.37-3.41 (m, 12H, methoxyethanamine CH$_2$, tren CH$_2$), 3.49 (q, J=6.7 Hz, tren CH$_2$), 4.89 (s, 8H, Bn CH$_2$), 5.06 (s, 4H, Bn CH$_2$), 5.07 (s, 4H, Bn CH$_2$), 6.90 (s, 4H, ArH), 7.31-7.42 (m, 40H, Ph), 7.43 (d, J=10.5 Hz, 2H, ArH), 7.49 (d, J=10.5 Hz, 2H, ArH), 7.62 (t, J=6.5 Hz, 2H, amide H), 7.69 (t, J=6.5 Hz, 4H, amide H), 8.07 (t, J=5.5 Hz, 2H, amide H).

$^{13}$C NMR (100 MHz, CD$_2$Cl$_2$): δ 36.7, 37.0, 39.6, 51.8, 52.4, 58.3, 70.6, 76.3, 76.8, 76.9, 124.7, 125.4, 125.8, 128.3, 128.3, 128.5, 128.5, 128.5, 128.6, 130.2, 132.0, 136.1, 136.3, 136.7, 150.3, 150.5, 150.5, 164.3, 164.7, 164.7.

(+)-HR ESIMS calcd for C$_{106}$H$_{110}$O$_{18}$N$_{10}$Na (M+Na)=1833.7892. found m/z 1833.7866.

Tren$_2$TAM$_2$[TAM(OMeEtN)]$_2$ (12).

5 mL conc. HCl (12.1 N) was added to a solution of 11 (0.32466 g, 0.179 mmol) dissolved in 5 mL glacial acetic acid. The solution was stirred at room temperature for 64 hours and dried in vacuo. The resulting light yellow cake was suspended and dried with 10 mL portions of methanol several times, resulting in a light yellow solid. Further drying of this solid under vacuum overnight yielded a light gray solid (0.19037 g, 89%).

$^1$H NMR (500 MHz, D$_2$O+NaOD): δ 2.883 (t, J=7.3 Hz, 4H, tren CH$_2$), 2.93 (t, J=6.0 Hz, 8H, tren CH$_2$), 3.34 (s, 6H, CH$_3$), 3.41 (t, 6.3 Hz, 8H), 3.49-3.53 (m, 8H, tren CH$_2$, methoxyethanamine CH$_2$), 3.60 (t, J=5.5 Hz, 4H, methoxyethanamine CH$_2$), 6.54 (s, 4H, ArH), 6.87 (s, 2H, ArH), 6.87 (s, 2H, ArH).

$^{13}$C NMR (125 Hz, DMSO-d$_6$): δ 34.3, 34.4, 49.0, 50.4, 51.6, 51.9, 58.4, 70.5, 116.6, 116.7, 116.9, 117.0, 117.3, 118.4, 119.6, 149.5, 150.5, 150.6, 150.9, 169.0, 169.1, 170.8.

(+)-HR ESIMS calcd for C$_{50}$H$_{62}$O$_{18}$N$_{10}$Na (M+Na): 1113.4136. found m/z 1113.4126.

Anal. calcd for C$_{50}$H$_{62}$O$_{18}$N$_{10}$·3HCl: C, 50.03; H, 5.46; N, 11.67. Found: C, 50.38; H, 5.58; N, 11.51.

[Th(phi(2,2)moeTAM)]4K.

12 (13.65 mg, 0.0114 mmol) was suspended in 7 mL methanol at 45° C. A stoichiometric amount of 1M KOH in methanol (0.09 mL, 0.0910 mmol) was added to the ligand suspension dropwise, to a pH of 8, bringing the ligand into solution. A solution of Th(NO$_3$)$_4$·4H$_2$O in 1 mL methanol was added dropwise to the ligand solution while stirring, and white precipitate formed immediately. (The thorium solution can be added before the addition of base.) The reaction mixture was refluxed under nitrogen flow overnight, and once cooled to room temperature, was placed at 4° C. The product was further precipitated by addition of diethyl ether and concentration of the reaction mixture. The tan precipitate was filtered and dried overnight under vacuum, resulting in a light brown solid (15.11 mg, 93%).

(−)-HR ESIMS calcd for C$_{50}$H$_{54}$O$_{18}$N$_{10}$Th (M+H): 438.1338. found m/z 438.1355.

Example 2

Synthesis of phi(3,3)moeTAM

The syntheses for a phi(2,2)moeTAM and phi(3,3)moeTAM are identical, with the exception of the amine starting material for the scaffold moiety.

Scheme. Synthesis of phi(3,3)mocTAM.
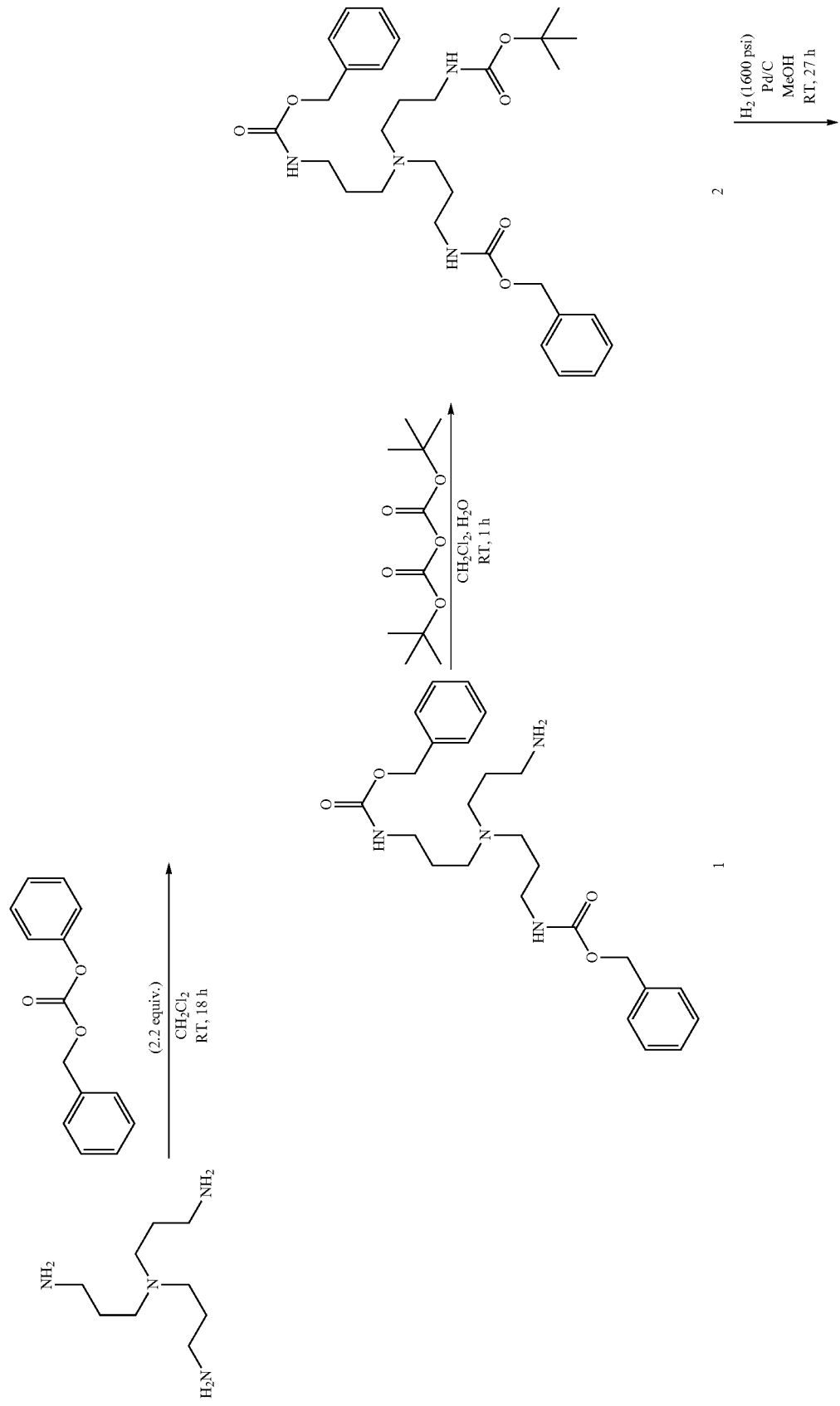

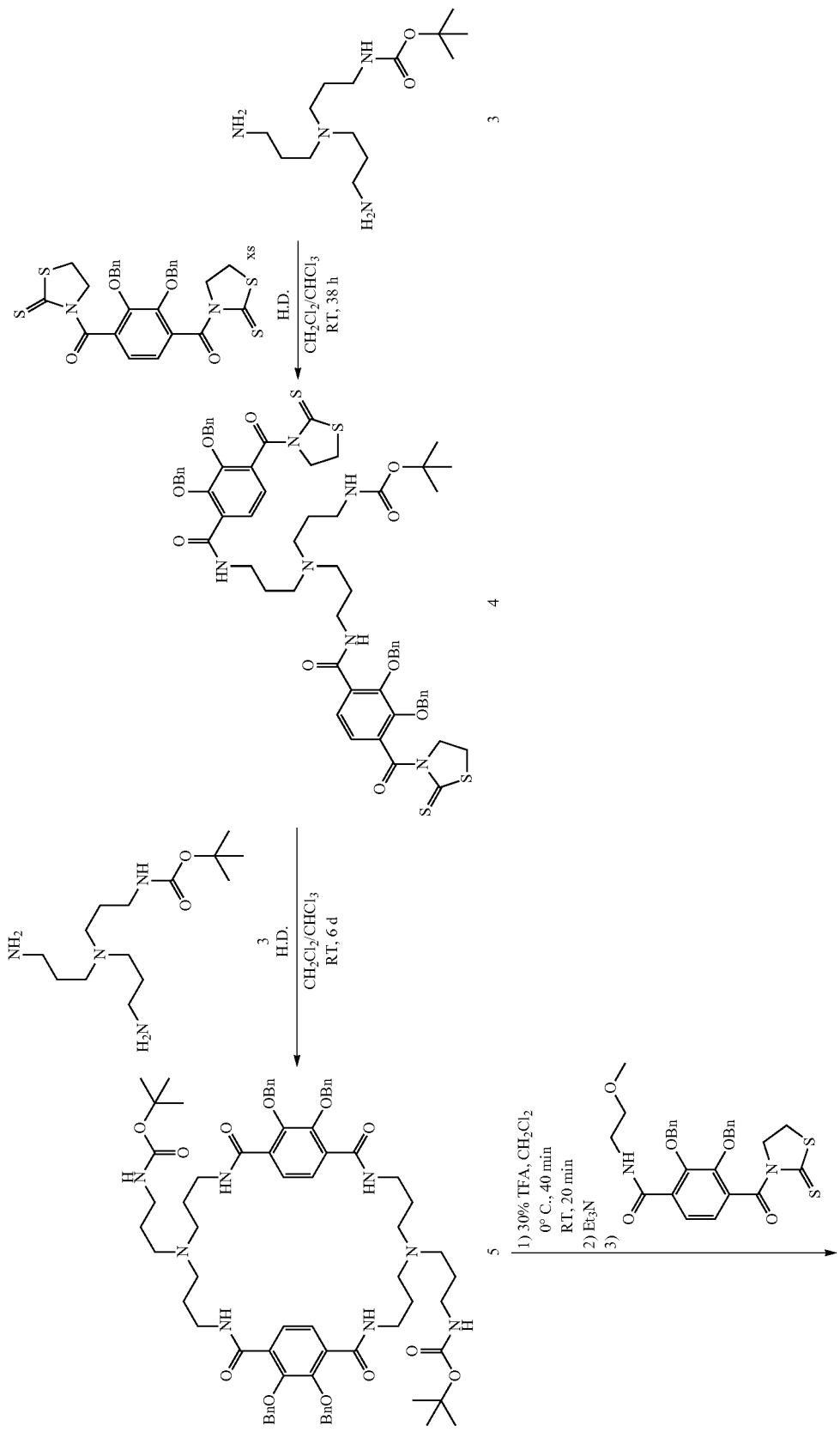

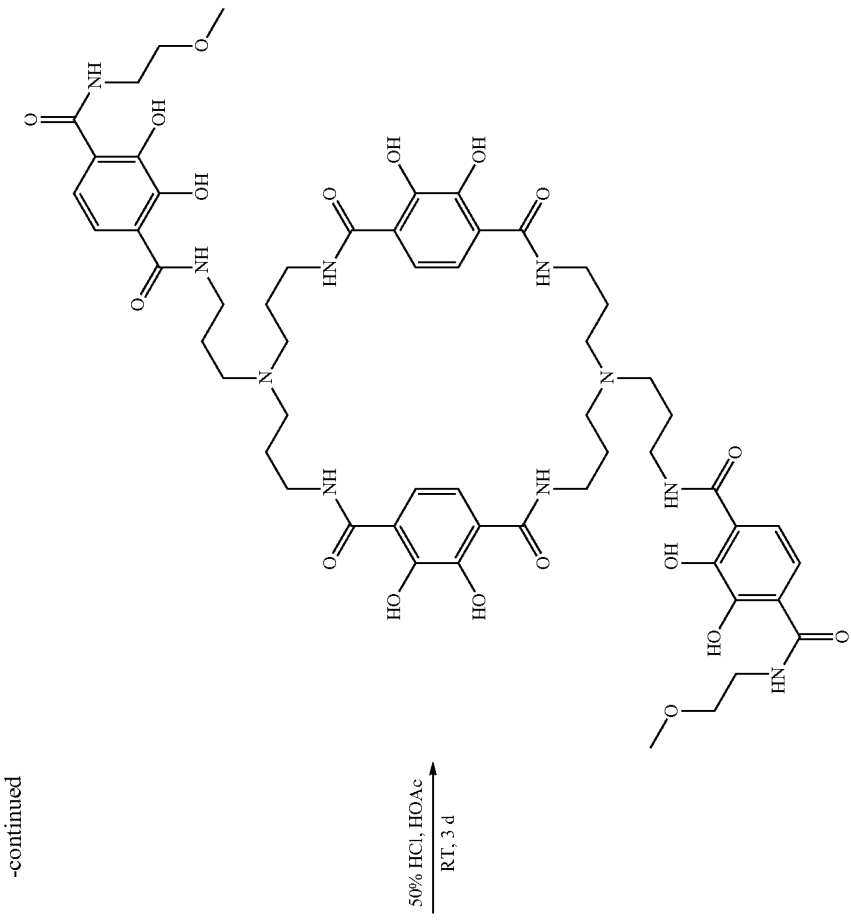
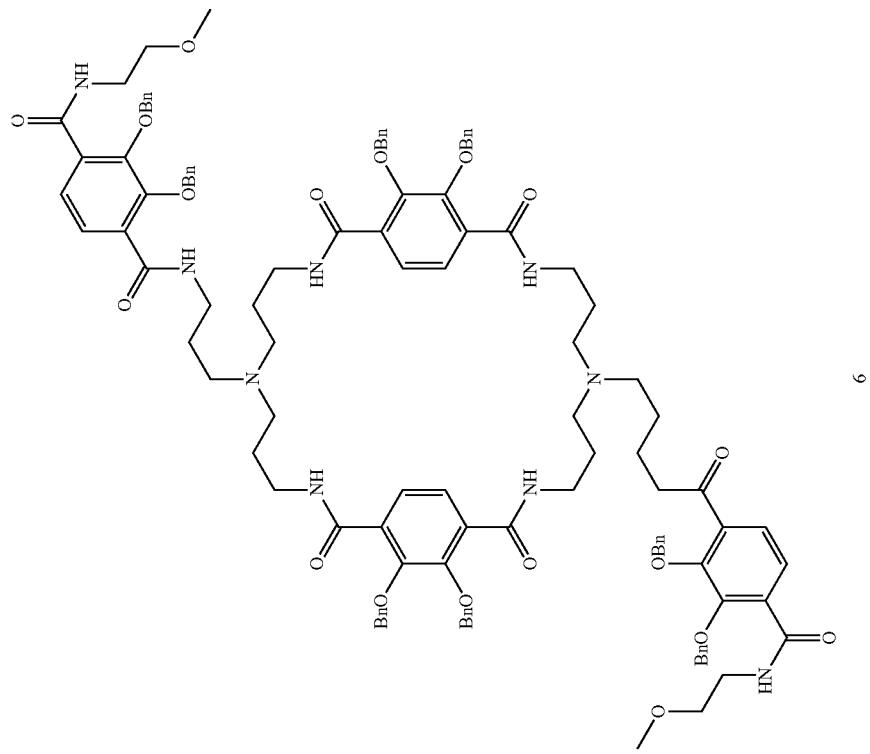

DiCbz-TRPN (1).

Benzyl phenyl carbonate (7.68 mL, 38.9 mmol; a gift from Dr. Jide Xu) was added dropwise to a stirring and cold solution (on an ice-water bath) of TRPN (3.50 mL, 17.7 mmol) in 20 mL degassed $CH_2Cl_2$. The ice-water bath was removed after 1.5 hr, and the capped solution was left to stir overnight. The resulting peach-colored solution was purified by column chromatography (5-15% MeOH in $CH_2Cl_2$ with 1% triethylamine). The fractions containing pure product were combined and evaporated on the vacuum line with light heating to obtain a clear, yellow oil (45%).

$^1$H NMR (500 MHz, $CD_2Cl_2$, δ): 1.54 (quin, J=7.0 Hz, —$CH_2CH_2CH_2NH_2$, 2H), 1.63 (quin, J=6.6 Hz, —$CH_2CH_2CH_2NHCbz$, 4H), 2.39-2.43 (m, —$CH_2CH_2CH_2NH_2$ and —$CH_2CH_2CH_2NHCbz$, 6H), 2.67 (t, J=6.8 Hz, —$CH_2CH_2CH_2NH_2$, 2H), 3.21 (q, J=6.2 Hz, —$CH_2CH_2CH_2NHCbz$, 4H), 5.07 (s, Bn $CH_2$, 4H), 6.05 (br s, amide NH), 7.29-7.35 (m, Ar H, 10H).

$^{13}$C NMR (151 MHz, $CD_2Cl_2$, δ): 11.3, 27.0, 39.7, 40.3, 46.2, 66.1, 127.77, 127.8, 128.2, 128.4, 137.3, 156.5.

HRMS-ESI (m/z): [M+H]$^+$ calcd for $C_{25}H_{37}O_4N_4$, 457.2809. found, 457.2809.

DiCbz-monoBoc-TRPN (2).

A 50-mL round-bottom flask was charged with 1 (2.0544 g 1.0.20Et$_3$N.0.22MeOH, 4.23 mmol), 9 mL $CH_2Cl_2$ to dissolve the oil, an aqueous solution of $NaHCO_3$ (0.3843 g, 4.57 mmol), NaCl (0.980 g, 15.2 mmol), and a solution of di-tert-butyl carbonate (0.9859 g, 4.52 mmol) dissolved in 3 mL $CH_2Cl_2$. The reaction mixture bubbled for 20 min, and was left to stir overnight. It was then filtered, and the organic layer was separated from the filtrate. The aqueous layer was extracted with 10 and 5 mL $CH_2Cl_2$. The combined organic layers were purified by column chromatography (0-10% MeOH in $CH_2Cl_2$). The fractions containing pure product were rotary evaporated to yield a clear, colorless oil (92%).

$^1$H NMR (500 MHz, $CD_2Cl_2$, δ): 1.41 (s, t-Bu $CH_3$, 9H), 1.55-1.59 (m, —$CH_2CH_2CH_2NHBoc$, 2H), 1.62 (quin, J=6.6 Hz, —$CH_2CH_2CH_2NHCbz$, 4H), 2.37-2.41 (m, —$CH_2CH_2CH_2NHBoc$ and —$CH_2CH_2CH_2NHCbz$, 6H), 3.10 (br q, J=6.0 Hz, —$CH_2CH_2CH_2NHBoc$, 2H), 3.20 (q, J=6.2 Hz, —$CH_2CH_2CH_2NHCbz$, 4H), 5.06 (s, Bn $CH_2$, 4H), 5.74 (br s, amide NH, 2H), 7.28-7.34 (m, Ar H, 10H).

$^{13}$C NMR (151 MHz, $CD_2Cl_2$, δ): 27.0, 27.2, 28.1, 39.1, 39.6, 50.1, 51.7, 66.2, 78.6, 127.8, 127.8, 128.3, 137.2, 155.9, 156.4.

HRMS-ESI (m/z): [M+H]$^+$ calcd for $C_{30}H_{45}O_6N_4$, 557.3334. found, 557.3345.

MonoBoc-TRPN (3).

2 (2.30 g of 2.1.89MeOH, 3.73 mmol) was dissolved in 30 mL MeOH in a glass vessel and mixed with a suspension of 0.400 g Pd/C (Pd 10% wt.) in 5 mL MeOH. A stir bar was added to the vessel, which was then placed in a pressure bomb. The bomb was pressurized with 1650 psi H$_2$ and placed on a stirring plate to stir the reaction for 27 h. The reaction mixture was filtered through a fine glass frit, and the filtrate was rotary evaporated and further dried on the vacuum line to afford a clear, colorless oil (100%).

$^1$H NMR (500 MHz, $CD_2Cl_2$, δ): 1.41 (s, t-Bu $CH_3$, 9H), 1.59 (quin, J=6.8 Hz, —$CH_2CH_2CH_2NHBoc$, 2H), 1.77 (br quin, J=6.3 Hz, —$CH_2CH_2CH_2NH_2$, 4H), 2.42 (t, J=6.8 Hz, —$CH_2CH_2CH_2NHBoc$, 2H), 2.50 (t, J=6.2 Hz, —$CH_2CH_2CH_2NH_2$, 4H), 2.93 (t, J=6.8 Hz, —$CH_2CH_2CH_2NH_2$, 4H), 3.05 (br q, J=5.5 Hz, —$CH_2CH_2CH_2NHBoc$, 2H), 6.01 (br s, amide NH, 1H), 8.53 (s, $NH_2$, 2H).

$^{13}$C NMR (151 MHz, $CD_2Cl_2$, δ): 24.9, 26.7, 27.4, 38.1, 38.4, 48.4, 50.8, 50.9, 78.6, 157.2.

HRMS-ESI (m/z): [M+H]$^+$ calcd for $C_{14}H_{33}O_2N_4$, 289.2598. found, 289.2596.

MonoBoc-diTAMBndithiaz-TRPN (4).

A solution of TAMBndithiaz (50.603 g, 87.1 mmol) and 10 drops triethylamine in 1.2 L $CH_2Cl_2$ was degassed in a 2-L round-bottom flask. A degassed solution of 3 (0.9457 g 3.2.59MeOH, 2.34 mmol) and 7 drops triethylamine in 400 mL $CH_3Cl$ in a 500-mL round bottom flask was degassed and slowly dripped (through a capillary) into the stirring solution of TAMBndithiaz. The dripping (of about 2 drops/sec) was started by briefly flowing nitrogen into the 500-mL flask and took 38 h to complete. The reaction was left to stir for an additional 8 h, concentrated by rotary evaporation, and purified by column chromatography (0-10% MeOH in $CH_2Cl_2$). The fractions containing pure product were combined and rotary evaporated to yield a yellow foamy solid (74%).

$^1$H NMR (600 MHz, $CD_2Cl_2$, δ): 1.39 (s, t-Bu $CH_3$, 9H), 1.58-1.64 (m, —$CH_2CH_2CH_2TAM$ and —$CH_2CH_2CH_2NHBoc$, 6H), 2.49 (t, J=5.5 Hz, —$CH_2CH_2CH_2TAM$, 4H), 2.54 (t, J=5.5 Hz, —$CH_2CH_2CH_2NHBoc$, 2H), 3.03 (t, J=6.0 Hz, —$CH_2CH_2CH_2TAM$, 4H), 3.10 (br q, J=4.5 Hz, —$CH_2CH_2CH_2NHBoc$, 2H), 3.24 (q, J=5.5 Hz, —$NCH_2CH_2S$—, 4H), 4.40 (t, J=6.3 Hz, —$NCH_2CH_2S$—, 4H), 5.10 (s, Bn $CH_2$, 4H), 5.12 (s, Bn $CH_2$, 4H), 7.17 (d, J=6.5 Hz, TAM Ar H, 2H), 7.34-7.40 (m, Bn Ar H), 7.74 (d, J=7.0, TAM Ar H, 2H), 7.84 (t, J=4.8, TAM amide NH, 2H), 8.25 (s, NBoc amide NH, 1H).

$^{13}$C NMR (151 MHz, $CD_2Cl_2$, δ): 28.1, 28.8, 37.67, 50.9, 55.6, 76.1, 76.8, 124.0, 126.1, 128.0, 128.3, 128.5, 128.7, 128.8, 128.9, 130.6, 133.5, 135.9, 137.0, 149.4, 150.1, 164.2, 166.6, 201.6.

HRMS-ESI (m/z): [M+H]$^+$ calcd for $C_{64}H_{71}O_{10}N_6S_4$, 1211.4109. found 1211.4119.

Φ(3,3)-TAMBn-NBoc (5).

4 (1.6669 g, 1.38 mmol) was dissolved in 900 mL $CH_3Cl$ with 10 drops triethylamine in a 1-L round bottom flask, and 3 (0.5535 g 3.2.59MeOH, 1.37 mmol) was dissolved in 900 mL $CH_3Cl$ with 25 drops triethylamine in a separate 1-L round bottom flask. The contents of the two flasks were simultaneously dripped, through capillaries, into 2 L of stirring $CH_2Cl_2$ in a 3-necked round bottom flask. The dripping required approximately 6 d, after which the solution was left to stir for an additional day. 3 mL diisopropylethylamine was added to the reaction mixture to trap unreacted 4, and the reaction mixture was again left to stir for a day before concentration by rotary evaporation and purification by column chromatography (1-4% MeOH in $CH_2Cl_2$). Pure product (71%), as a yellow foamy solid, could only be obtained after elution from three silica columns due to the excess of triethylamine and diisopropylethylamine present in the reaction mixture.

$^1$H NMR (500 MHz, $CD_2Cl_2$, δ): 1.38 (s, t-Bu $CH_3$, 18H), 1.57 (t, J=6.0 Hz, —$CH_2CH_2CH_2TAM$ and —$CH_2CH_2CH_2NHBoc$, 12H), 2.28 (br s, —$CH_2CH_2CH_2TAM$, 8H), 2.34 (br s, —$CH_2CH_2CH_2NHBoc$, 4H), 3.08 (br q, J=6.0 Hz, —$CH_2CH_2CH_2NHBoc$, 4H), 3.32 (q, J=6.2 Hz, —$CH_2CH_2CH_2TAM$, 8H), 4.94 (s, Bn $CH_2$, 8H), 7.29-7.36 (m, Bn Ar H and TAM Ar H, 24H), 8.02 (t, J=5.8 Hz, TAM amide NH, 4H).

$^{13}$C NMR (151 MHz, $CD_2Cl_2$, δ): 27.2, 28.7, 38.1, 39.83, 42.2, 50.5, 51.2, 52.3, 54.4, 77.3, 79.0, 125.7, 129.0, 129.0, 129.2, 132.5, 137.0, 150.7, 156.4, 156.6.

HRMS-ESI (m/z): [M+H]$^+$ calcd for $C_{72}H_{93}O_{12}N_8$, 1261.6907. found 1261.6908.

Φ(3,3)-TAMBn-moeTAMBn (6).

A 50-mL round bottom flask was charged with 5 (0.5081 g, 0.403 mmol), 9 mL CH$_2$Cl$_2$, and a stir bar, and placed in an ice-water bath. Trifluoroacetic acid (4 mL, 52 mmol) was added dropwise to the stirring, cooled solution dropwise over 6 min. The reaction progress was monitored by TLC every 10-15 min. The water bath was removed 30 min following the addition, and the reaction mixture was left at room temperature for 25 min. It was then placed on the vacuum line to evaporate the solvent, side products, and excess acid (by coevaporation with CH$_2$Cl$_2$). The thick oil was placed on an ice-water bath, dissolved in approximately 8 mL CH$_2$Cl$_2$, and neutralized with 1.5 mL triethylamine. The reaction mixture was left to stir for 15 min, removed from the bath, and combined with a solution of TAMBnthiaz-moe (0.880 g, 1.64 mmol) in 10 mL CH$_2$Cl$_2$. The solution was stirred for 18 h at room temperature, and transferred to a reparatory funnel, to which 20 mL H$_2$O was added. The aqueous layer was acidified with 1M HCl$_{(aq)}$ to pH 7, and extracted with 4 times with 5-10 mL CH$_2$Cl$_2$. The combined organic layers were combined, concentrated by rotary evaporation, and purified by column chromatography (1-10% MeOH in CH$_2$Cl$_2$). Purification with two columns and drying (by rotary evaporation and vacuum line) afforded an off-white solid (72%).

$^1$H NMR (600 MHz, CD$_2$Cl$_2$, δ): 1.78 (br s, —CH$_2$CH$_2$CH$_2$TAM, 8H), 2.21-2.42 (m, —CH$_2$CH$_2$CH$_2$TAM and —CH$_2$CH$_2$CH$_2$TAMmoe and —CH$_2$CH$_2$CH$_2$TAMmoe, 14H), 3.22 (s, moe CH$_3$, 6H), 3.23-3.28 (m, —CH$_2$CH$_2$CH$_2$TAMmoe and —CH$_2$CH$_2$CH$_2$TAM, 12H), 3.40 (t, J=4.2 Hz, —CH$_2$CH$_2$OCH$_3$, 6H), 3.50 (q, J=4.5 Hz, —CH$_2$CH$_2$OCH$_3$, 4H), 4.93 (s, TAM Bn CH$_2$, 8H), 5.12 (s, TAMmoe Bn CH$_2$, 8H), 7.23 (br s, TAM Ar H, 4H), 7.28-7.44 (m, Bn Ar H), 7.77 (d, J=6.5 Hz, TAMmoe Ar H, 2H), 7.85 (d, J=7.0 Hz, TAMmoe Ar H, 2H), 7.94 (TAMmoe amide NH, 4H), 7.97 (t, J=4.2 Hz, TAM amide NH, 4H).

$^{13}$C NMR (151 MHz, CD$_2$Cl$_2$, δ): 27.1, 27.3, 38.1, 38.8, 40.2, 51.1, 51.9, 59.0, 71.4, 77.3, 77.6, 77.7, 125.8, 126.6, 126.8, 129.1, 129.1, 129.2, 129.2, 129.2, 129.2, 129.3, 129.3, 129.3, 129.4, 131.3, 136.6, 136.6, 137.0, 150.8, 151.1, 151.1, 164.5, 165.6.

HRMS-ESI (m/z): [M+2H]$^{2+}$ calcd for C$_{112}$H$_{124}$O$_{18}$N$_{10}$, 948.4542. found, 948.4546.

φ(3,3)-TAM-moeTAM (7).

A 25-mL round-bottom flask (previously soaked in an EDTA bath) was charged with 6 (0.1981 g, 0.105 mmol), 5 mL glacial acetic acid, and a stir bar. After a few minutes and with stirring, the solid dissolved, and 5 mL concentrated HCl was added to the solution. The reaction mixture was left to stir at room temperature for 3 d, and put on the vacuum line with gentle heating, using a 50° C. water bath. The solution was coevaporated with several portions of H$_2$O and MeOH, and left on the vacuum line at room temperature overnight. An off-white solid (85%) was obtained as the HCl salt of 7.

$^1$H NMR (600 MHz, DMSO-d$_6$, δ): 1.91 (br m, —CH$_2$CH$_2$CH$_2$TAM, 8H), 1.99 (br m, —CH$_2$CH$_2$CH$_2$TAMmoe), 3.15 (br m, —CH$_2$CH$_2$CH$_2$TAM and —CH$_2$CH$_2$CH$_2$TAMmoe, 12H), 3.27 (s, moe CH$_3$, 6H), 3.39-3.41 (m, —CH$_2$CH$_2$CH$_2$TAM and —CH$_2$CH$_2$OCH$_3$, 10H), 3.46-3.50 (m, —CH$_2$CH$_2$OCH$_3$ and —CH$_2$CH$_2$OCH$_3$ and —CH$_2$CH$_2$CH$_2$TAMmoe, 10H), 7.24 (s, TAM Ar H, 4H), 7.36 (d, J=7.5 Hz, TAMmoe Ar H, 2H), 7.40 (d, J=7.5 Hz, TAMmoe Ar H, 2H), 8.97-8.99 (m, TAM amide NH and TAMmoe amide NH, 6H), 9.04 (t, J=4.5 Hz, TAMmoe amide NH, 2H), 12.54 (s, TAM OH, 2H), 12.55 (s, TAM OH, 2H), 12.58 (s, TAMmoe OH, 2H), 12.69 (s, TAMmoe OH, 2H).

$^{13}$C NMR (151 MHz, DMSO-d$_6$, δ): 22.8, 23.1, 36.0, 36.4, 49.1, 19.5, 57.9, 70.0, 115.8, 115.9, 116.0, 117.2, 117.3, 117.5, 149.9, 149.9, 150.0, 168.5, 168.8, 168.9.

HRMS-ESI (m/z): [M−2H]$^-$ calcd for C$_{56}$H$_{73}$O$_{18}$N$_{10}$, 1173.5110. found, 1173.5105.

Anal. calcd for 7.4HCl (C$_{56}$H$_{78}$C$_{14}$N$_{10}$O$_{18}$): C, 50.91; H, 5.95; N, 10.60. Found: C, 50.82; H, 5.28; N, 10.05.

[Th(phi(3,3)moeTAM)]4PyH.

7 (0.0102 g, 0.0077 mmol) was dissolved in 4 mL MeOH in a 10-mL round-bottom flask (previously soaked in an EDTA bath) containing a stir bar. Th(NO$_3$)$_4$.4H$_2$O (0.0042, 0.0076 mmol) dissolved in 1 mL MeOH was added dropwise to the ligand solution, resulting in the immediate color change of the reaction mixture from colorless to yellow as well as the formation of fine, white precipitate. 2 drops of pyridine (~0.01 mL, 0.1 mmol) were added to the reaction mixture, producing more precipitation. The flask was attached to a condenser and the reaction mixture was refluxed, while stirring, in an oil bath for 4.5 h. It was then cooled to room temperature and filtered to isolate a light brown solid, which was dried in vacuo overnight (76%).

HRMS-ESI (m/z): [M+3H]$^-$ calcd for C$_{56}$H$_{69}$O$_{18}$N$_{10}$Th$_1$, 1401.5177. found, 1401.5191.

Example 3

Synthesis of Macrocycles with Pendant 1,2-HOPO, 1-Me-3,2-HOPO, 3,4-HOPO or CAMS) Chelating Moieties

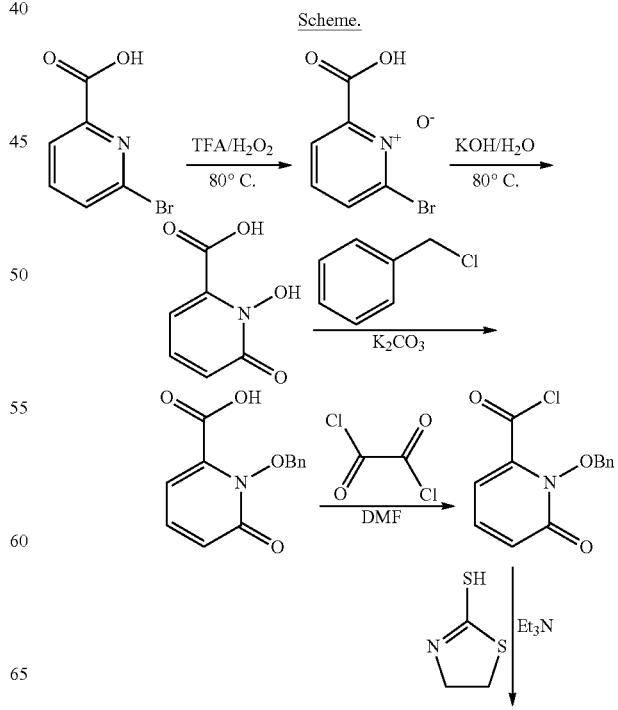

Scheme.

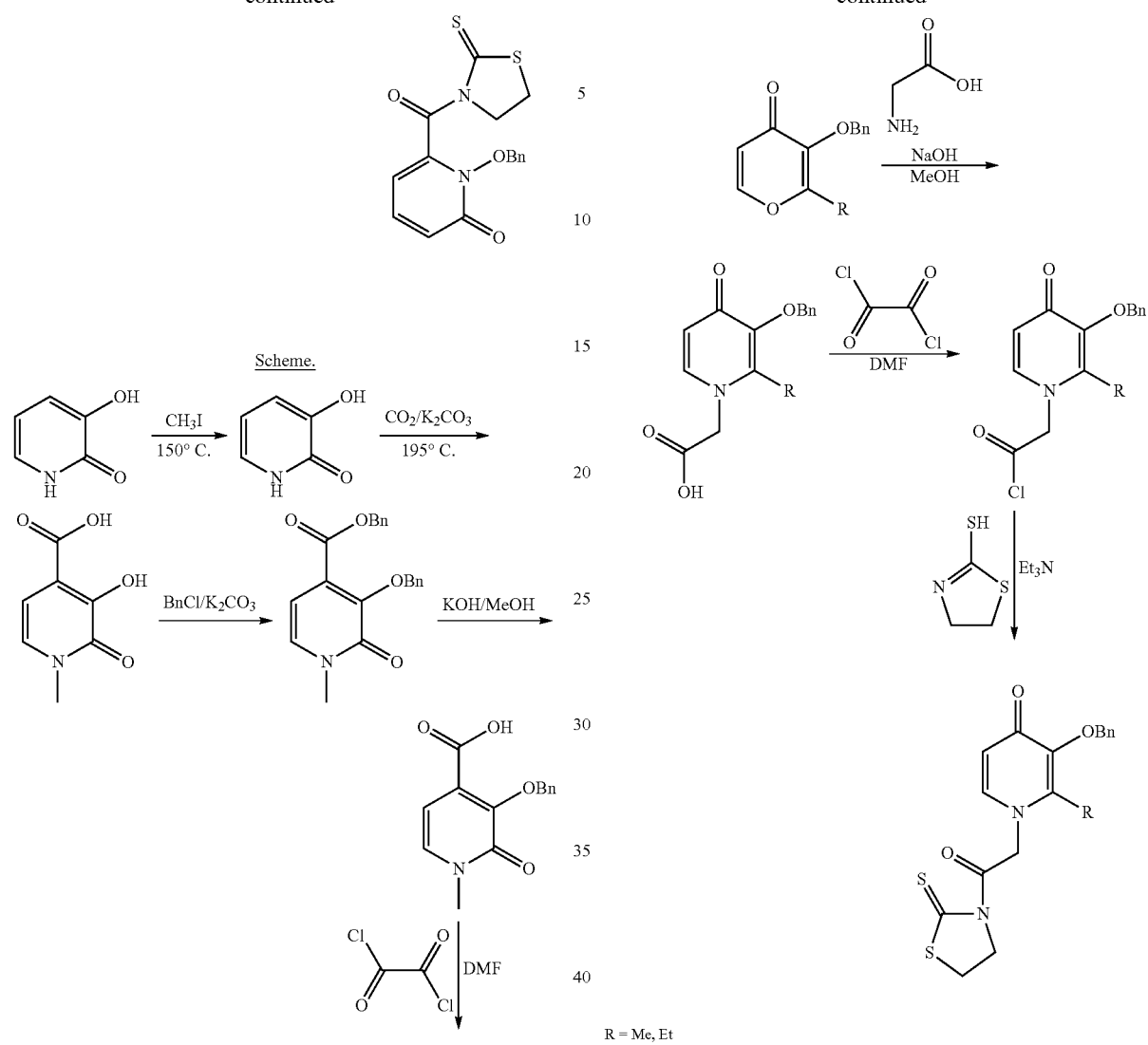
R = Me, Et

71
-continued
72
-continued
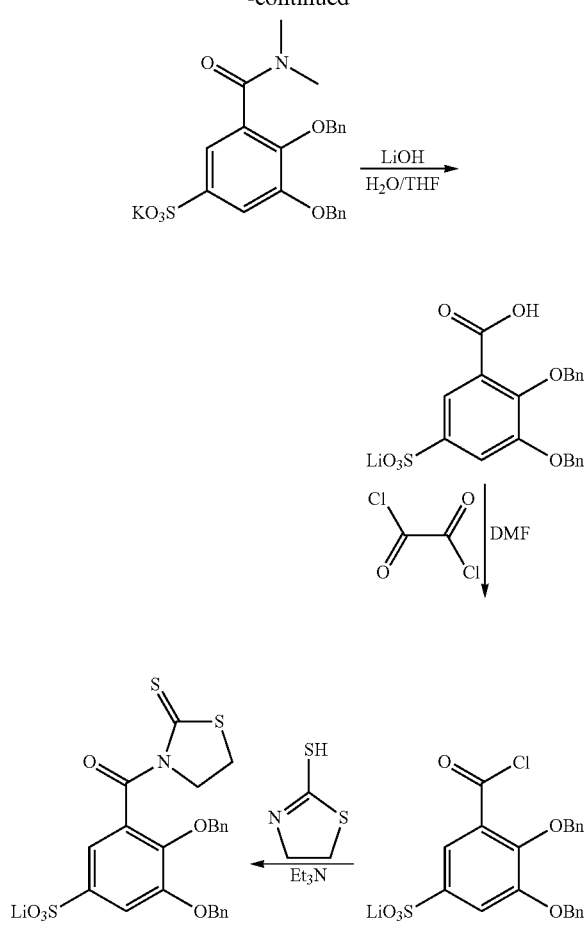
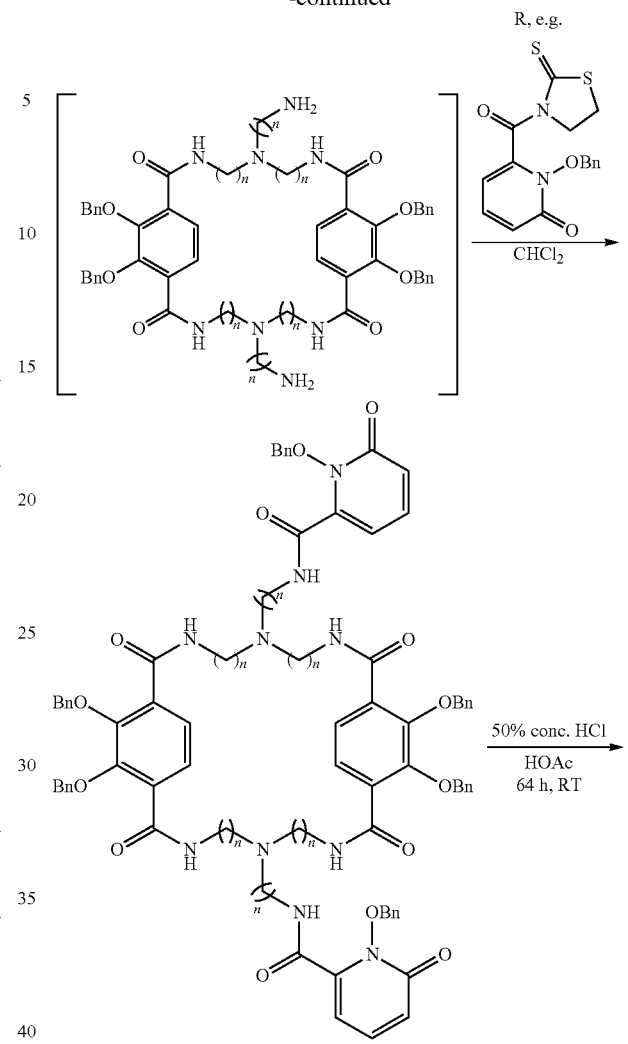
Scheme.
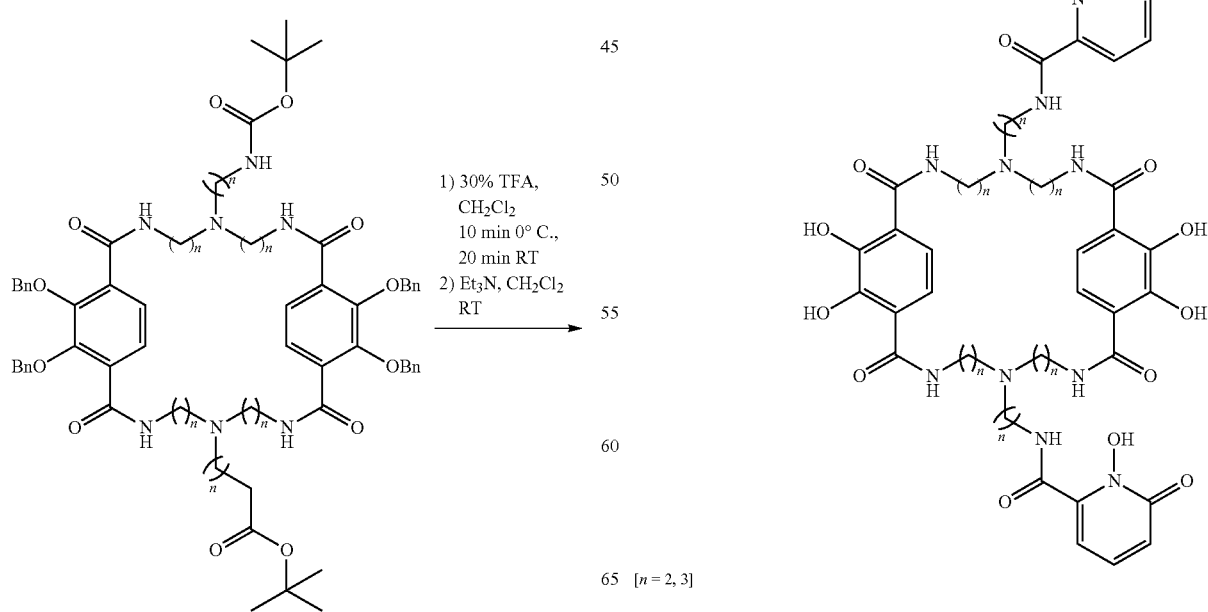
[n = 2, 3]

73
Example 4
Synthesis of a 3,4,3-LI Macrocycle
Scheme. Synthesis of a 3,4,3-LI macrocycle.
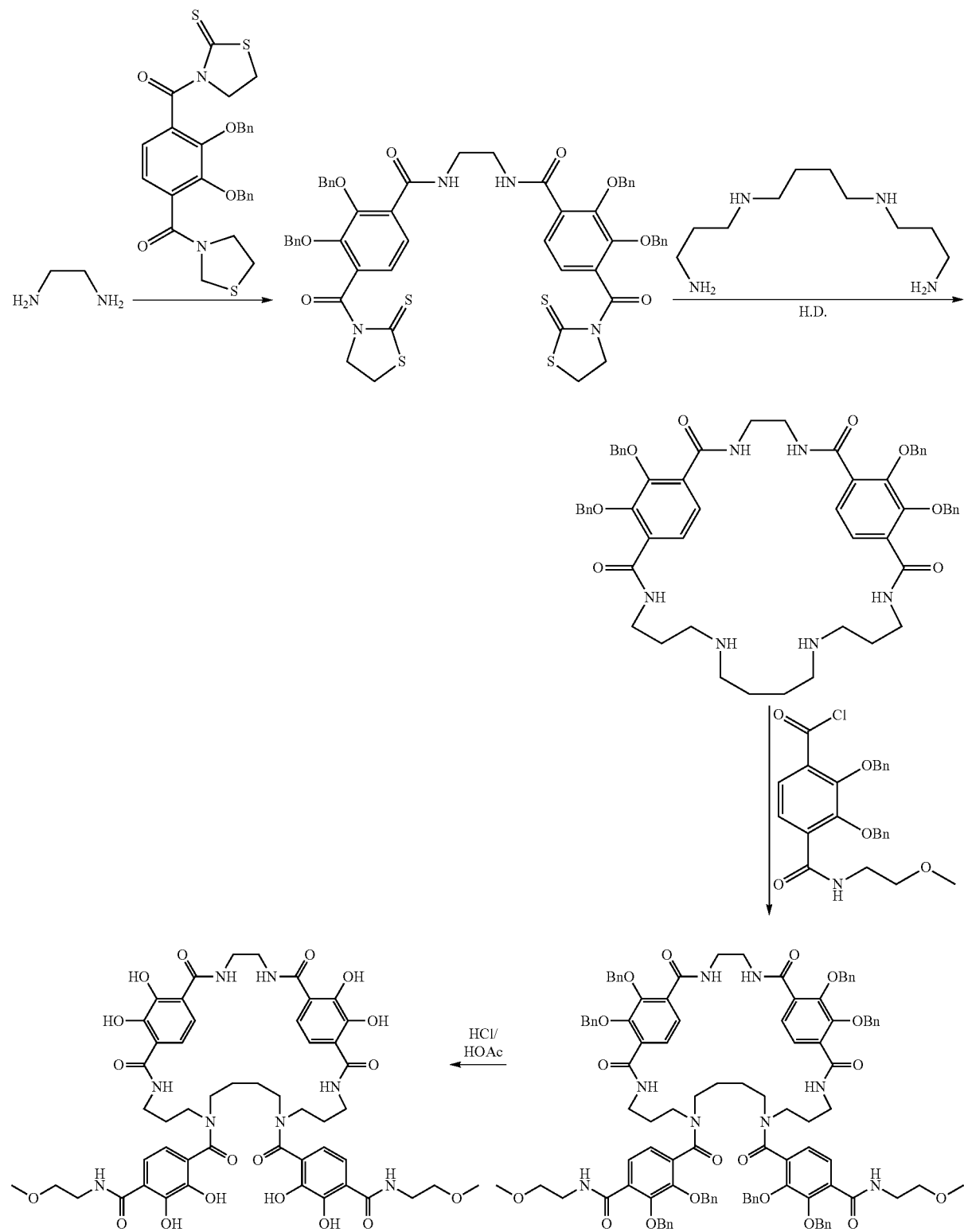

Example 5

Solution Thermodynamics

All spectrophotometric titrations were carried out with constant stirring and a blanket of argon flow in a jacketed cell connected to a recirculating water bath to maintain the temperature at 25° C. All solutions contained 0.1 M KCl with 5% DMSO (v/v), for consistency with titrations where DMSO was used to ensure solubility. The ligand was added as a 50 mM DMSO stock solution, and Th(IV) as a standardized 10 mM stock solution in nitric acid (79 mM). The HCl and KOH solutions were prepared by dilution of Dilut-It (J. T. Baker) concentrated solutions with degassed Millipore water containing 5% DMSO, to maintain the DMSO concentration constant throughout the titration. The 0.1 M HCl solution was standardized by titration of Tris using bromocresol green as an indicator, and the 0.1 M KOH solution was standardized by titration of KHP using phenolphthalein as an indicator. The glass electrode (Nova Analytics Pinnacle) used for the pH measurements was calibrated by adding 2.000 mL 0.1 M HCl (5% DMSO) to 50.0 mL 0.1 M KCl (5% DMSO), and titrating the solution to pH 11.6 with 0.1 M KOH (5% DMSO). The titration was analyzed using the program GLEE to refine for $\mathcal{E}^\circ$ and the slope. For low pH titrations, a strong acid calibration was performed by titrating 50.0 mL 0.1 M KCl with 5% (v/v) DMSO with 0.1 M HCl to pH 1.8. The data were analyzed in an Excel spreadsheet using the SOLVER function to refine for $\mathcal{E}^\circ$ and the slope. Metrohm Brinkmann 665 Dosimat instruments were the automated burettes used to dispense the titrant, the pH meter was a Fisher Accumet AR 15, and the UV-Vis spectrometer a Hewlett-Packard 8452A. The computer program Labview was the interface from which all these components were orchestrated to run the titrations. A value of $-14.20$ was used as the $pK_w$ to account for the DMSO content.

Ligand Titrations.

50 mL solutions (5% DMSO) of 50 µM ligand and 20 equivalents (1 mM) each of MES, HEPES, and CHES, were titrated forward and backward between pH 1.9 and 12.7 with standardized 0.1 M KOH and 0.1 M HCl. The data points were collected at constant increments of 0.05 pH units at pH 1.9-11.5, with an equilibration time of 90-500 sec following titrant additions and a 10 min. delay between successive pH readings. Titration data above pH 11.5 was collected at constant increments of 0.10 pH units, to minimize the time at which the electrode is exposed to strongly basic conditions. All absorbance measurements used in the refinement were no more than 1.0 absorbance units. Spectra from 300-450 nm were analyzed (simultaneously) in the program pHAb. Titrations for constants reported with a standard deviation were performed in triplicate (the standard deviation is between individually refined values for each titration).

Th(IV) Competition Titrations.

50 mL solutions of 50 µM ligand, 50 µM Th(IV), and 500 µM EDTA (Sigma Aldrich) or DTPA (Pharm-Eco) were titrated forward and backward with standardized 0.1 M KOH and 0.1 M HCl. The data points were collected at constant increments of 0.05 pH units, with an equilibration time of 90-500 sec following titrant additions and a 20-30 min delay between successive pH readings. All absorbance measurements used in the refinement were no more than 1.1 absorbance units. Spectra from 300-450 nm were analyzed (simultaneously) in the program pHAb. The following values for the log β for the formation of Th hydroxides were included in the refinement: $[ThOH]^{3+}$, $-2.5$; $[Th(OH)_2]^{2+}$, $-6.2$; $Th(OH)_4$, $-17.4$; $[Th_2(OH)_2]^{6+}$, $-5.9$; $[Th_2(OH)_3]^{5+}$, $-6.8$; $[Th_4(OH)_8]^{8+}$, $-20.4$; $[Th_4(OH)_{12}]^{4+}$, $-26.6$; $[Th_4(OH)_{14}]^{2+}$, $-36.8$; $[Th_4(OH)_{15}]^{+}$, $-36.8$. The following stability constants for Th with EDTA (DTPA) were also included: log $\beta_{011}$, 10.17 (10.45); log $\beta_{012}$, 16.28 (18.98); log $\beta_{013}$, 18.96 (23.26); log $\beta_{014}$, 22.46 (25.91); log $\beta_{015}$, 22.46 (27.73); log $\beta_{110}$, 23.2 (28.78); log $\beta_{111}$, 25.18 (30.94). Spectra of the free ligand, refined from the ligand titrations, were set constant in the refinement as well.

Figure 1B:
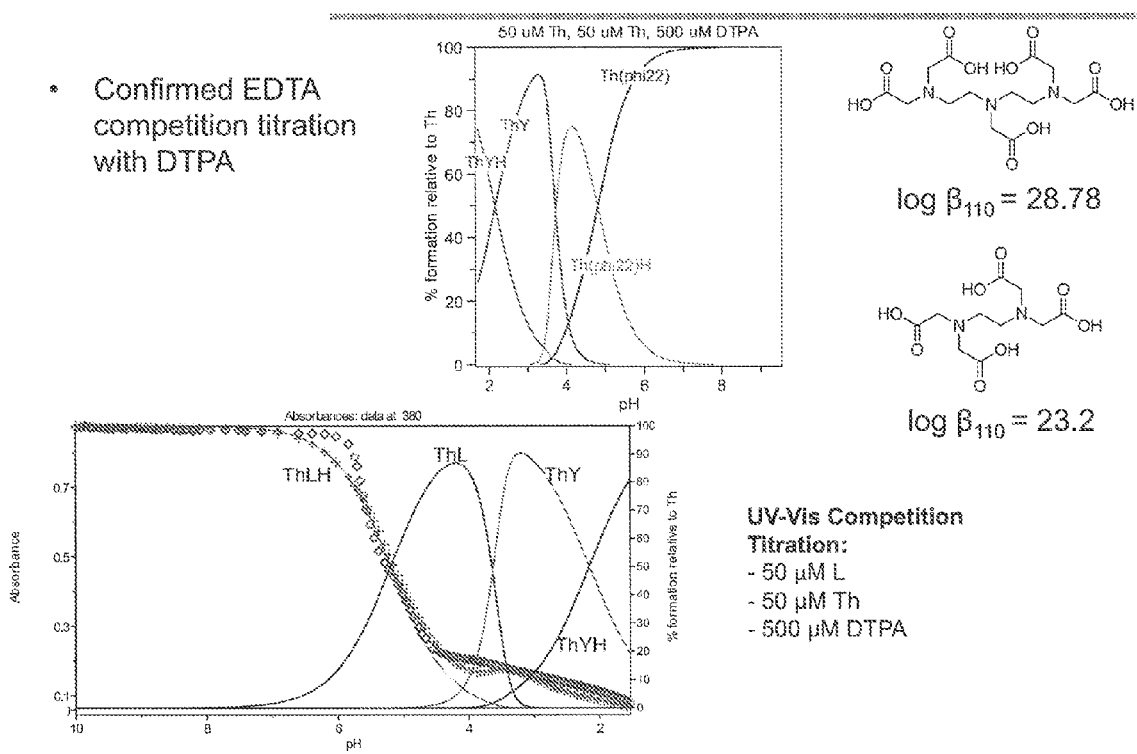

FIGS. 1A and 1B show solution thermodynamics data for the Th(IV)-phi(2,2)moeTAM complex. "L" in FIGS. 1A and 1B refers to phi(2,2)moeTAM.

The protonation constants of phi(2,2)moeTAM were determined by potentiometric and spectrophotometric titration, and its binding affinity for Th(IV) was subsequently determined by spectrophotometric EDTA competition titration. The log $\beta_{110}$ (where $\beta_{mlh}$ is the cumulative stability constant for the equilibrium mM+lL+hH $\leftrightarrows$ $M_m L_l H_h$) was found to be 53.7(5), over 24 orders of magnitude greater than that of DTPA (28.78).[15] Furthermore, its greater log $\beta_{110}$ value relative to the log $\beta_{140}$ for ethyl-TAM, 45.54,[13] suggests that the macrocyclic topology and the all secondary amide linkers and their hydrogen bonding confer additional thermodynamic stability to the Th(IV)-phi(2,2)moeTAM complex. This conclusion is supported by studies with a linear analog, 3,4,3-LiMeTAM (structure shown below), which features the same TAM binding moieties tethered to a linear backbone. The log $\beta_{110}$ of this ligand with Th(IV) is 56.1. Although this binding constant is larger than that of the macrocycle, the greater stability at the physiologically relevant pH of 7.4 is reflected in the differences in pM values.

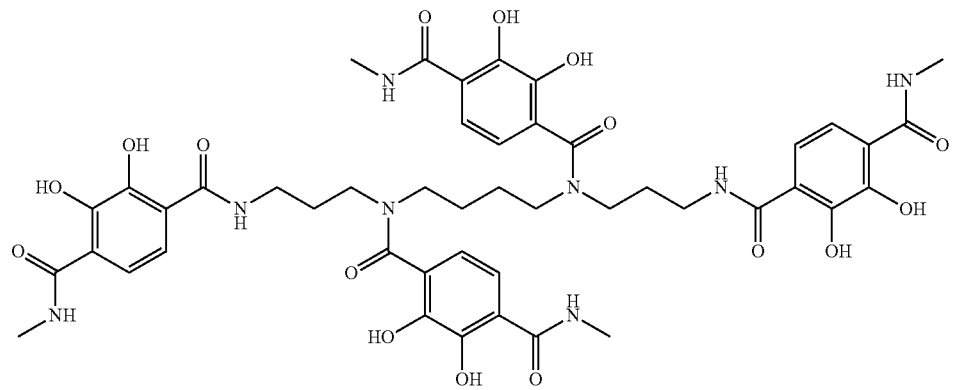 [SMILES: CNC(=O)c1ccc(C(=O)NCCCN(CCCCN(CCCNC(=O)c2ccc(C(=O)NC)c(O)c2O)C(=O)c2ccc(C(=O)NC)c(O)c2O)C(=O)c2ccc(C(=O)NC)c(O)c2O)c(O)c1O]

3,4,3-LiMeTAM

The binding affinities can also be evaluated with the pM value, the negative logarithm of the free metal concentration, at standard conditions of 1 μM metal, 10 μM ligand, and pH 7.4. This pM value for phi(2,2)moeTAM is 40.2, which is larger than the pM of 39.2 for 3,4,3-LiMeTAM, as well as 14 and 21 orders of magnitude greater than the pM values for DTPA and ethyl-TAM, respectively. These data demonstrate the unprecedented stability of the Th(IV)-phi(2,2)moeTAM complex.

Example 6

Kinetic Studies

Th Stock Solution.

A standardized stock solution of $Th^{4+}$ was prepared by dissolving $Th(NO_3)_4 \cdot 4H_2O$ (Alfa Products) in Millipore water with 0.5% (77.9 mM) $HNO_3$ (0.01 M, 2 L). This solution was titrated with $Na_2H_2EDTA$ (standard solution, Sigma Aldrich) to the yellow endpoint, using pyrocatechol violet as the indicator. This complexometric titration was performed until a standard deviation of 0.0001 M was obtained.

Ligand Stock Solutions.

5.00 mM DMSO solutions of the ligands were made by dissolving the appropriate amount of the solid ligand (as determined by elemental analysis) into DMSO, and kept at 4° C., in the dark, when not in use.

Dye purification.

100 mg of arsenazo III (Sigma) was dissolved in Millipore water, filtered through a 0.22 um nylon syringe filter, and separated on a super-preparatory Varian Dynamax 250× 41.1 mm C18 column. A solvent gradient that began with 100:0:$H_2O$:MeCN (and 0.1% TFA) was used to collect three fractions with intense UV absorbances. The peak with the most intense absorbance (rt 15-16 min) was collected as the main product, without the front or back tailing compound. The fraction was rotary evaporated, and the dark purple-green solid was resuspended in methanol before drying under vacuum overnight.

(−)-HR ESIMS calcd for $C_{22}H_{13}As_2O_{14}N_4S_2Na_2$ (M−5H+3Na): 419.8998. found m/z 419.9173.

Anal. calcd for $C_{22}H_{18}As_2O_{14}N_4S_2 \cdot 2H_2O$: C, 32.53; H, 2.73; N, 6.90. Found: C, 32.34; H, 2.73; N, 6.71.

UV-Vis Displacement Kinetic Experiments.

Spectra were acquired on an Hewlett-Packard 8453 spectrometer at 25° C. The temperature was controlled by a recirculating water bath connected to a jacketed cell holder. Samples were measured in small volume (50 μL) quartz cuvettes with 1 cm path lengths. Solutions were buffered with 100 mM HEPES at pH 7.4 (at 25° C.) and 100 mM KCl. Complexation of the thorium and dye was performed by combining aqueous stock solutions of standardized $Th^{4+}$ in nitric acid (77.9 mM $HNO_3$, pH 1.4, 1 mM) and purified dye (1 mM). The solution was let sit on the bench at room temperature for 30 min, diluted in buffer, and let sit at room temperature for an hour. The absorbance was monitored starting from the addition of ligand, as a solution of DMSO ligand stock solution (5 mM) and buffer (equilibrated for 15 min. beforehand). The A vs. t plots were fit with a first-order decay equation in Origin at wavelengths corresponding to the appearance of free dye (550, 560 nm) and the disappearance of thorium-dye complex (614, 669, 700 nm). The reaction with DOTA was refluxed (and stirred with a magnetic stir bar) and performed on a 3 mL scale (instead of 100 μL) in a 10 mL round-bottom flask, placed in an oil bath, and fitted with a reflux condenser. Aliquots were taken periodically and transferred to a cuvette for UV-Vis spectra acquisition.

Figure 2:
FIG. 2 shows comparative kinetic data for the complexation of Th(IV) to various ligands.
Figure 2:
Figure 2:
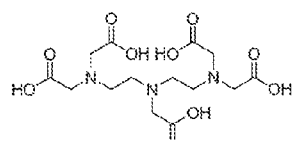
Figure 2:
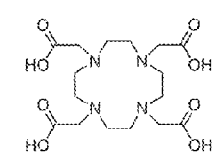

FIG. 2 shows comparative kinetic data for the complexation of Th(IV) to various ligands.

The kinetics of complexation were studied indirectly by UV-Vis spectroscopy in water at physiological pH. In order to monitor a change in the visible region, a dye was used in competition experiments in which the ligand displaced the dye from the thorium ion. The rate of appearance of free dye or disappearance of Th-dye complex provided qualitative data useful in the comparison of the kinetic behavior of different ligands. phi(2,2)moeTAM was found to complex Th(IV) with a rate 1-2 orders of magnitudes greater than those of DOTA and DTPA, both commercially available aminocarboxylic acids used in current radiotherapeutic agents.

Example 7 phi(2,2)-moeTAM-Th UV-Vis Kinetics

The stopped-flow kinetic experiments were performed using a stopped-flow apparatus equipped with an OLis rapid-scanning monochromator 1000 and a 75 W Xe lamp. Upon electronic activation, the apparatus (powered with a gas source, in this case, Ar) mixes 100 μL of each solution in the two syringes into a mixing chamber. This mixture is flowed into a separate chamber, where the flow is stopped and UV spectra are taken. One syringe contained 10 μM Th(IV) in 77.9 mM $HNO_3$ (pH 1.4), while the other held a solution of 50-300 μM ligand, in 200 mM HEPES (pH 8.3) and 10% DMSO. The 1:1 mixture of these solutions was 5 μM Th, 25-150 μM ligand, 100 mM HEPES (pH 7.4). UV spectra in the 305-454 nm range were collected for 1.5-10 s, depending on the concentrations of the starting materials, at rates of 31-1000 scans/s. The data were analyzed using the program SpecFit to simultaneously use the absorbance at all of the wavelengths to obtain a second-order rate constant.

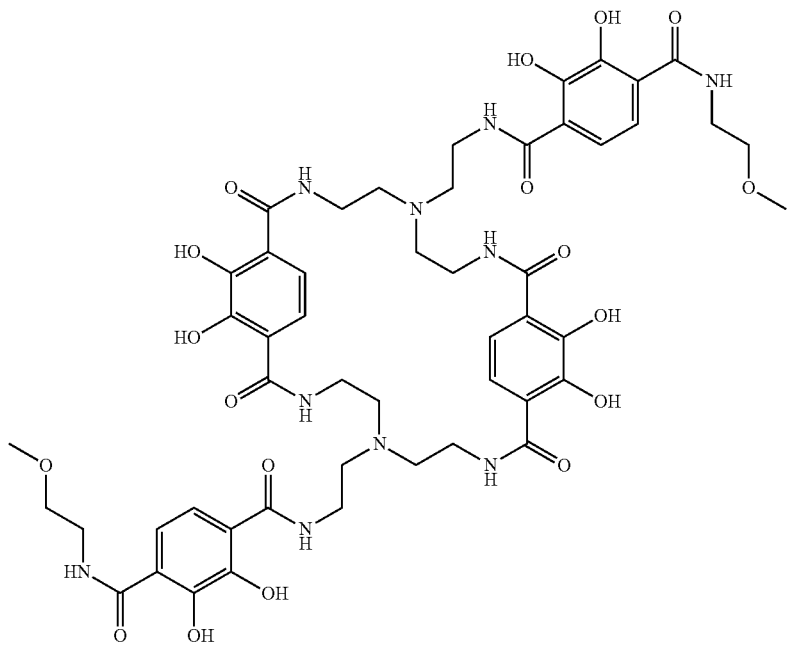

phi(2,2)-moeTAM ligand (L).

Figure 5:
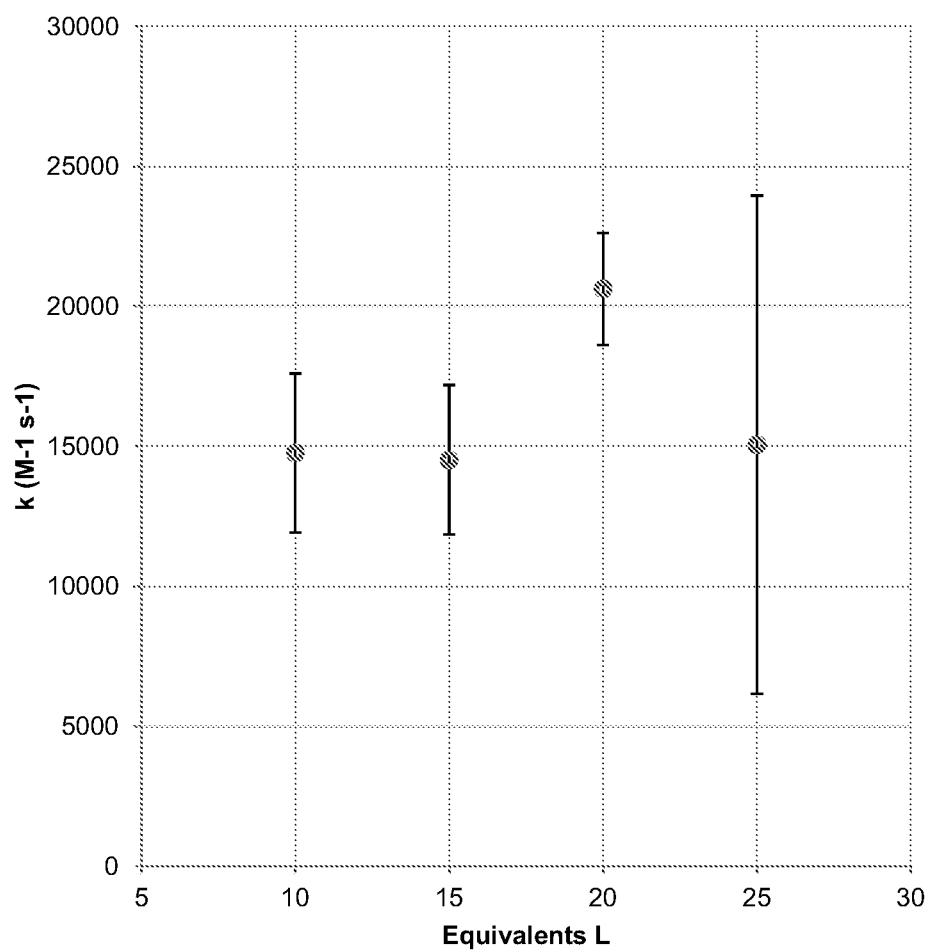
FIG. 5 shows a graph of second-order rate constants obtained from stopped-flow kinetics experiments with 5 μM Th, 10-25 equivalents of phi(2,2)moeTAM (L), 100 mM HEPES (pH 7.4), 5% DMSO. The black bars denote the standard deviation; each point is an average of at least 20 runs.

The kinetics of the direct association of L with Th(IV) have been elusive thus far due to the presence of various species in solution (as the metal ion can hydrolyze to form various species such as $Th(OH)^{3+}$, $Th(OH)_2^{2+}$, $Th_4(OH)_{12}^{4+}$, and $Th(OH)_4$, and L has many protonation states) and the small spectral change upon complexation. Thus far, the rate of complex formation has only been characterized by indirect kinetic experiments using a dye. However, UV-Vis kinetics experiments using a stopped-flow apparatus and more intense light source enabled a direct and quantitative assessment of the complexation. The experiment was designed such that Th(IV) hydrolysis would be kept to a minimum, while allowing the reaction to proceed at pH 7.4, where the ligand would be partially deprotonated and able to complex Th(IV). Using the stopped-flow apparatus, it was possible to reproducibly and quickly mix a solution of Th(IV) at pH 1.4 and a solution L at pH 8.2; the 1:1 mixture of the two gave a pH of 7.4. The complexation was performed with a 5-30 fold excess of L for pseudo-first order conditions from which a second-order rate constant could be extrapolated. The spectral change upon complexation was rather small (FIG. 3), especially at higher concentrations of L, a problem which was circumvented by increasing the amount of light through the sample (a smaller range of wavelengths could then be analyzed, since some parts of the spectrum were saturated). Ideal second-order behavior was not observed, as the $k_2$ vs. equiv. L plot in FIG. 5 shows: the second-order rate constant increases significantly at 30 equivalents of ligand, and is significantly lower at 5. The data at 30 equivalents is not as reliable, as indicated by the much larger standard deviation, and can reasonably be omitted.

Figure 3A:
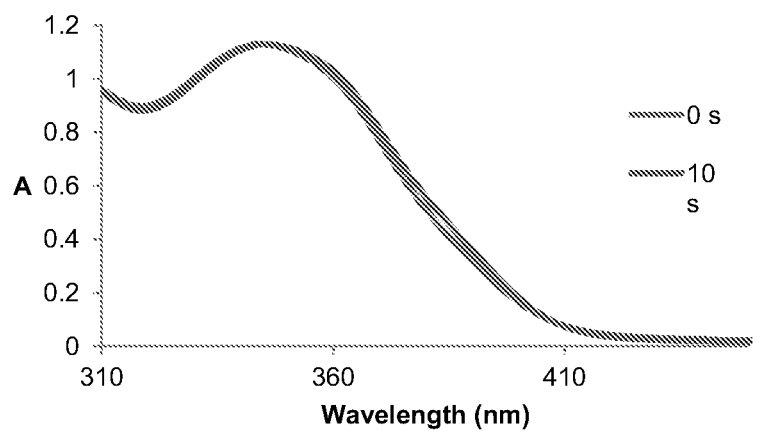
FIGS. 3A and 3B show UV-Vis data obtained from stopped-flow kinetics experiments with 10 equivalents phi (2,2)moeTAM (L). A) Full spectrum analyzed. B) Trace at 380 nm.
Figure 3B:
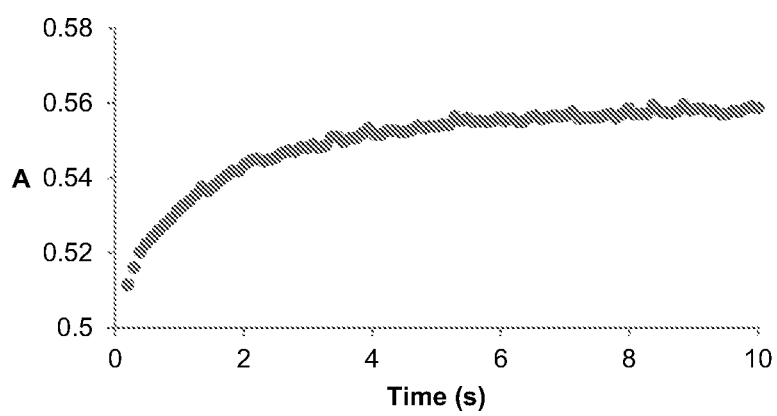

FIGS. 3A and 3B show UV-Vis data obtained from stopped-flow kinetics experiments with 10 equivalents phi(2,2)moeTAM (L). A) Full spectrum analyzed. B) Trace at 380 nm.

Figure 4:
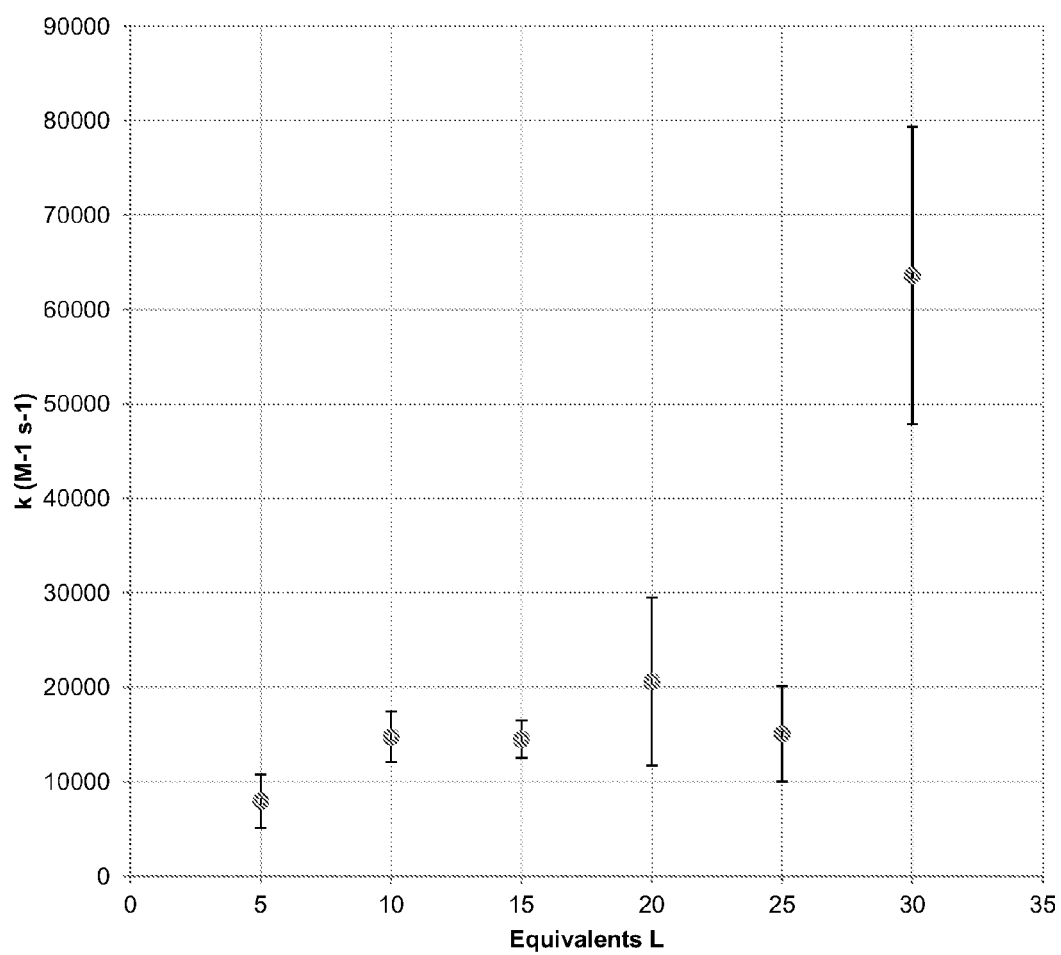
FIG. 4 shows a graph of second-order rate constants obtained from stopped-flow kinetics experiments with 5 μM Th, 5-30 equivalents of phi(2,2)moeTAM (L), 100 mM HEPES (pH 7.4), 5% DMSO. The black bars denote the standard deviation; each point is an average of at least 20 runs.

FIG. 4 shows a graph of second-order rate constants obtained from stopped-flow kinetics experiments with 5 µM Th, 5-30 equivalents of phi(2,2)moeTAM (L), 100 mM HEPES (pH 7.4), 5% DMSO. The black bars denote the standard deviation; each point is an average of at least 20 runs.

The data at 5 equivalents was also omitted for that same plot in FIG. 5, since at ligand concentrations below pseudo-first order, the mechanism can conceivably be different. Taking the average of the four remaining experiments, a value of $1.6(3) \times 10^4$ $M^{-1}$ $s^{-1}$ is obtained for the second-order rate constant. This rate constant is very high; at concentrations of 10 µM Th(IV) and 10 µM L, the reaction half-life is 3 seconds.

FIG. 5 shows a graph of second-order rate constants obtained from stopped-flow kinetics experiments with 5 µM Th, 10-25 equivalents of phi(2,2)moeTAM (L), 100 mM HEPES (pH 7.4), 5% DMSO. The black bars denote the standard deviation; each point is an average of at least 20 runs.

Example 8

Ce(IV)-phi(2,2)moeTAM Complex

[CeL]4K.

phi(2,2)moeTAM (L) (29.18 mg, 0.0197 mmol) was suspended in 4 mL methanol in a 10-mL round-bottom flask (that had been soaked in an EDTA bath overnight). A solution of $CeCl_3 \cdot 7H_2O$ (7.26 mg, 0.0195 mmol) in 1 mL methanol was added dropwise to the ligand solution while stirring, resulting in a yellow suspension. A stoichiometric amount of 0.2 M KOH in water (0.985 mL, 0.197 mmol) was added to the ligand suspension dropwise, to a pH of 8, and the reaction mixture immediately became dark purple, indicating the oxidation of Ce(III) to Ce(IV). The reaction mixture was refluxed under nitrogen flow for 3 h, and once cooled to room temperature, was dropped into 30 mL diethyl ether, producing a fine precipitate. The dark purple precipitate was filtered and dried overnight under vacuum (35.90 mg, 94%).

(−)-HR ESIMS calcd for $C_{50}H_{55}O_{18}N_{10}Ce$ $(M+H)^{3-}$: 407.7589. found m/z 407.7582.

Anal. calcd for $C_{50}H_{54}O_{18}N_{10}Ce \cdot 5KCl \cdot 12H_2O$: C, 30.51; H, 3.99; N, 7.12. Found: C, 30.76; H, 3.98; N, 7.00.

A selected crystal of CeL was mounted in Paratone N oil at the end of a captan loop and frozen in place under a low-temperature nitrogen stream. The data were collected on a Bruker APEX-II CCD X-ray diffractometer with Mo Kα radiation in the X-Ray Facility in the University of California, Berkeley College of Chemistry. Intensity data with a maximum 2θ range of 51.04° were extracted from the frames with the program APEX2. The data were corrected for Lorentz and polarization effects, and an empirical absorption correction was applied using the SADABS program. The structure was solved by direct methods and refined using full-matrix least squares refinements based on F2 in SHELXL-97. Crystallographic analyses were performed using the WinGX system of programs. All non-hydrogen atoms were refined anisotropically, while hydrogen atoms were assigned to idealized positions. Disordered solvent molecules were treated with the SQUEEZE procedure included in PLATON. A void of 922 Å$^3$ containing 287 electrons was found.

TABLE 1

Crystallographic data and structure refinement.

| | |
|---|---|
| Empirical formula | $C_{50}H_{54}CeK_4N_{10}O_{18}$ |
| $M_r$ | 1379.05 |
| Temperature | 100(2)K |
| Wavelength | 0.71073 Å |
| Crystal system | Triclinic |
| Space group | P1- |
| Unit cell dimensions | a = 11.3510(7) Å  α = 79.136(2)° |
| | b = 16.4110(12) Å  β = 86.923(2)° |
| | c = 20.1170(14) Å  γ = 80.584(2)° |
| V | 3632.1(4) Å$^3$ |
| Z | 2 |
| $\rho_{calcd}$ | 1.261 mg/m$^3$ |
| $\mu_{calcd}$ | 0.919 mm$^{-1}$ |
| F (000) | 1403 |
| Crystal size | 1.00 × 0.03 × 0.01 mm |
| 2θ range for data collection | 1.49 to 25.52° |
| Index ranges | −13 <= h <= 13, −19 <= k <= 19, −23 <= l <= 24 |
| Reflections collected | 25169 |
| Independent reflections | 12747 [R(int) = 0.0316] |
| Completeness to θ = 25.00° | 95.3% |
| Absorption correction | Semi-empirical from equivalents |
| Max. and min. transmission | 0.9909 and 0.4601 |
| Refinement method | Full-matrix least-squares on F$^2$ |
| Data/restraints/parameters | 12747/29/760 |
| Goodness-of-fit on F$^2$ | 1.134 |
| Final R indices [I > 2σ(I)] | R1 = 0.0815, wR2 = 0.2353 |
| R indices (all data) | R1 = 0.1036, wR2 = 0.2614 |
| Largest diff. peak and hole | 5.405 and −0.872 e · Å$^{-3}$ |

Figure 6:
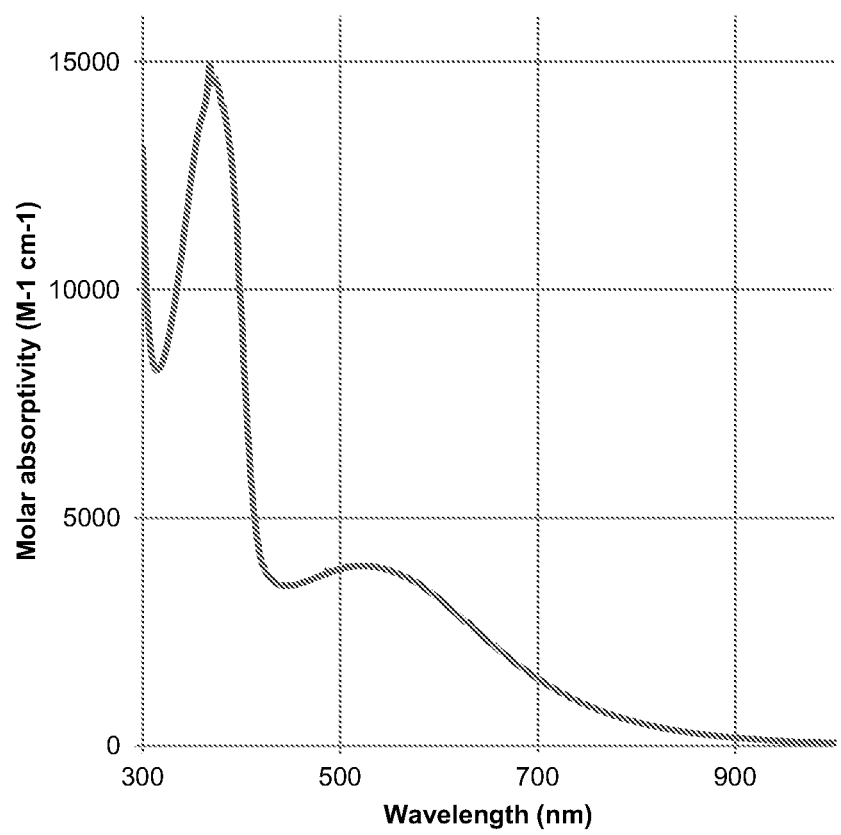
FIG. 6 shows a UV-Vis spectrum of $[CeL]^{4-}$ in aqueous solution: 100 mM HEPES (pH 7.4), 100 mM KCl. "L" in this paragraph refers to phi(2,2)moeTAM.
Figure 7:
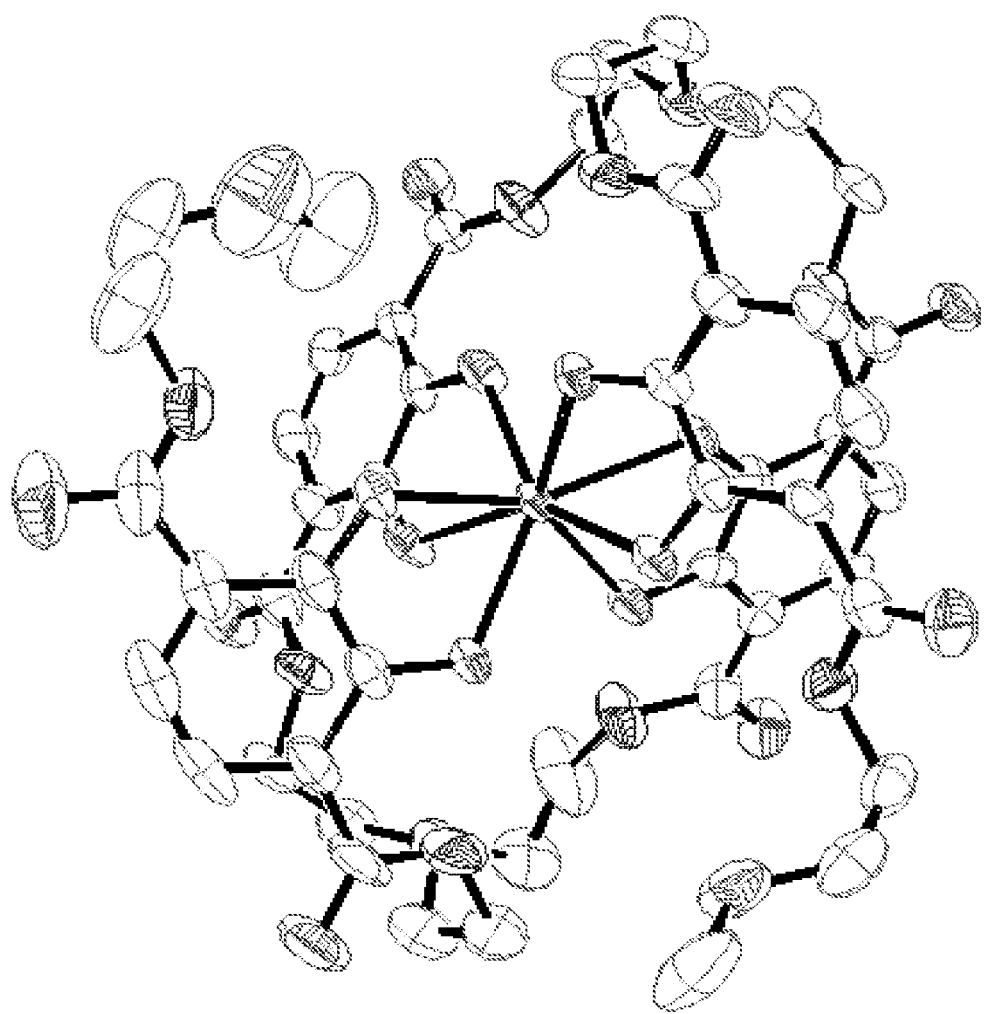
FIG. 7 shows an ORTEP diagram of the $[CeL]K_4$ complex. Ellipsoids are shown at 50% probability. Hydrogen and potassium atoms are omitted for clarity (gray C, red O, blue N, violet Ce). "L" in this paragraph refers to phi(2,2) moeTAM.

The Ce(IV) complex was successfully synthesized with the complexation of either Ce(IV) (as the sulfate solution) or Ce(III) (as the chloride solution) followed by air oxidation. The dark purple complex shows an intense and broad absorption at $\lambda_{max}$=522 nm, which is the LMCT band (FIG. 6). Single crystals suitable for X-ray diffraction were grown by the vapor diffusion of diisopropyl ether into a 1:4:DMF: MeOH solution of the isolated potassium salt of the Ce(IV) complex (FIG. 7). As with the Th(IV) complex, various other countercations were used for the crystallization (alkylammonium salts) but only the potassium salt crystallized adequately. The presence of the ordered and coordinated potassium ions suggests that they have a role in stabilizing the complex in a more rigid conformation. This is especially important given that the ligand is so large and flexible—one of the methoxyethyl substituents on the pendant arms exhibits some disorder, which was modeled over two positions (this was also seen in the Th structure). Solvent molecules were not ordered, and were accounted for with SQUEEZE to achieve a stable refinement. Other than with the shorter Ce—O bond lengths (Ce(IV) has an ionic radius of 97 pm, whereas Th(IV) is 105 pm), the crystal structure of the Ce complex is very similar to that of the Th complex in space group, unit cell, and inner coordination environment (Table 2a and 2b). The coordination geometry around the metal ion in both complexes is dodecahedral.

TABLE 2a

Selected crystallographic data of the Th and Ce complexes with phi(2,2)-moeTAM.

| [ThL]K$_4$ | | [CeL]K$_4$ | |
|---|---|---|---|
| Crystal system | Triclinic | Crystal system | Triclinic |
| Space group | P-1 | Space group | P-1 |
| Unit cell dimensions | a = 11.3472(15) Å | Unit cell dimensions | a = 11.3510(7) Å |
| | b = 16.549(2) Å | | b = 16.4110(12) Å |
| | c = 20.044(3) Å | | c = 20.1170(14) Å |
| | α = 79.129(2)° | | α = 79.136(2)° |
| | β = 87.126(2)° | | β = 86.923(2)° |
| | γ = 79.929(2)° | | γ = 80.854(2)° |
| Z | 2 | Z | 2 |
| Final R indices [I > 2σ(I)] | R1 = 0.0709, wR2 = 0.1711 | Final R indices [I > 2σ(I)] | R1 = 0.0815, wR2 = 0.2353 |
| Th—O bond lengths | 2.468(6)  2.416(7) | Ce—O bond lengths | 2.400(5)  2.344(5) |
| | 2.378(7)  2.382(6) | | 2.312(5)  2.325(5) |
| | 2.396(6)  2.399(6) | | 2.315(4)  2.363(5) |
| | 2.427(7)  2.412(7) | | 2.368(5)  2.343(5) |

TABLE 2b

Shape measure parameters for the inner coordination environments of the complexes; the shape measure is a reference to the agreement between the observed structure and the idealized polyhedra square antiprism (D$_{4d}$), bicapped trigonal prism (C$_{2v}$), and trigonal dodecahedron (D$_{2d}$).

| [ThL]K$_4$ | | | [CeL]K$_4$ | | |
|---|---|---|---|---|---|
| D$_{4d}$ | C$_{2v}$ | D$_{2d}$ | D$_{4d}$ | C$_{2v}$ | D$_{2d}$ |
| 11.1 | 8.8 | 7.8 | 10.8 | 9.2 | 7.4 |

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

We claim:
1. A macrocycle having the structure:

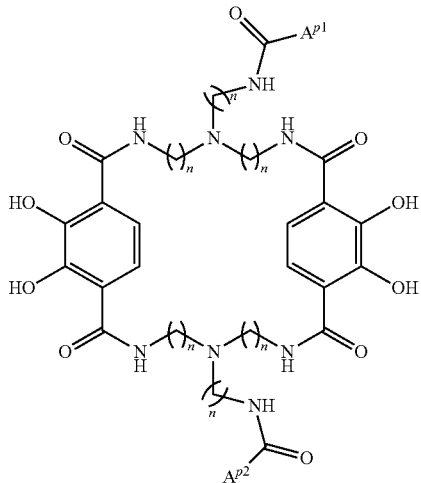

wherein $A^{p1}$ and $A^{p2}$ are independently selected from

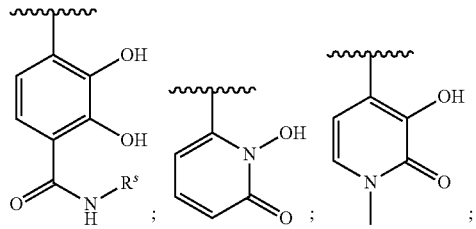

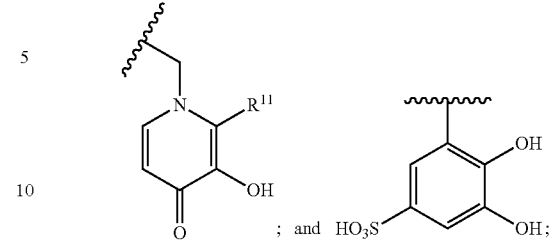

wherein $R^s$ comprises a solubilizing group; and
$R^{11}$ is methyl or ethyl; and
each n is an integer independently selected from 2 and 3.

2. The macrocycle according to claim 1, wherein $A^{p1}$ and $A^{p2}$ are each

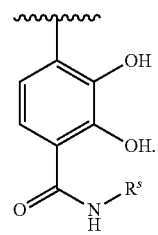

3. The macrocycle according to claim 2, having a structure selected from

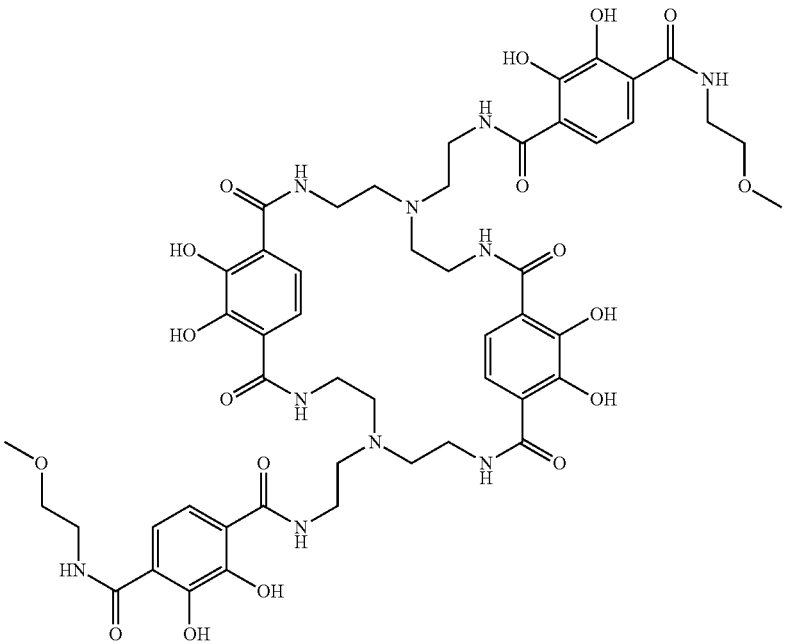

and

-continued
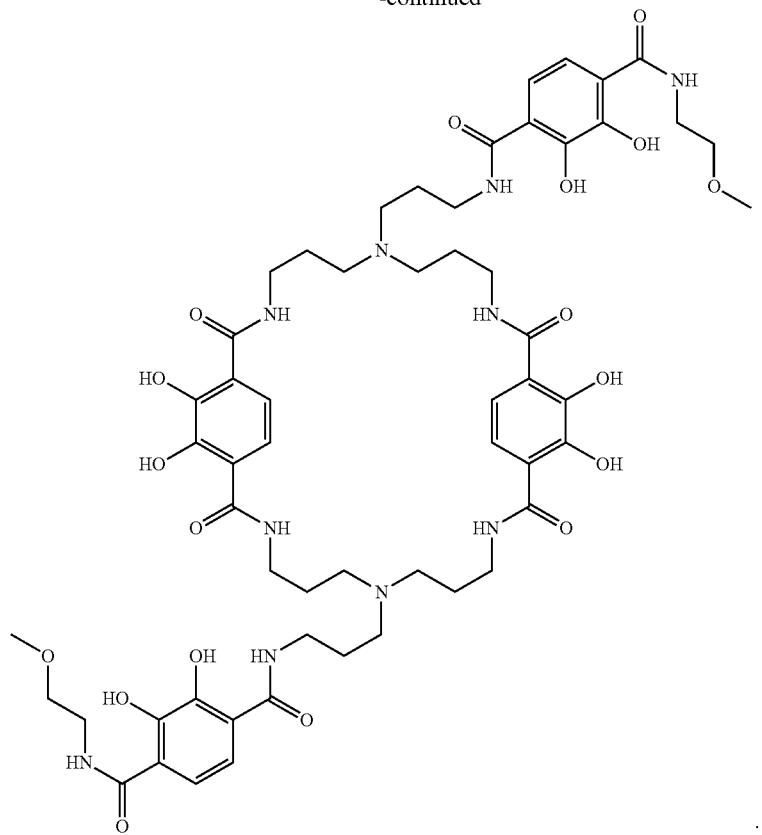
4. A complex comprising a macrocycle according to any one of the preceding claims and a metal ion.
5. The complex according to claim 4, wherein said metal is a radionuclide.
6. The complex according to claim 5, wherein said radionuclide is Thorium (Th).
7. The complex according to claim 5, wherein said radionuclide is Cerium (Ce).
* * * * *